(12) United States Patent
Falco

(10) Patent No.: US 11,028,355 B2
(45) Date of Patent: Jun. 8, 2021

(54) METHODS AND SYSTEMS FOR EFFICIENT BIOREACTOR MIXING AND LIGHT UTILIZATION EMBODYING LOW PROCESS ENERGY AND SCALABILITY

(71) Applicant: SolarClean Fuels, LLC, Fountain Hills, AZ (US)

(72) Inventor: Robert E. Falco, Fountain Hills, AZ (US)

(73) Assignee: SolarClean Fuels, LLC, Fountain Hills, AZ (US)

( * ) Notice: Subject to any disclaimer, the term of this patent is extended or adjusted under 35 U.S.C. 154(b) by 0 days.

(21) Appl. No.: 16/419,974

(22) Filed: May 22, 2019

(65) Prior Publication Data
US 2020/0369995 A1   Nov. 26, 2020

(51) Int. Cl.
*C12M 1/00*   (2006.01)
*C12M 1/107*   (2006.01)

(52) U.S. Cl.
CPC ............ *C12M 21/02* (2013.01); *C12M 23/22* (2013.01); *C12M 23/36* (2013.01); *C12M 29/00* (2013.01); *C12M 31/08* (2013.01)

(58) Field of Classification Search
CPC ...... C12M 21/02; C12M 23/22; C12M 23/36; C12M 29/00; C12M 31/08
USPC ................................ 435/289.1, 292.1, 295.2
See application file for complete search history.

(56) References Cited

U.S. PATENT DOCUMENTS

| | | |
|---|---|---|
| 2,732,663 A | 1/1956 | Dewey |
| 3,468,057 A | 9/1969 | Buisson et al. |
| 3,496,605 A | 2/1970 | Onaka |
| 3,650,068 A | 3/1972 | Meyer et al. |
| 4,217,728 A | 8/1980 | Shimamatsu et al. |
| 4,233,958 A | 11/1980 | Heden |
| 4,473,970 A | 10/1984 | Hills |
| 4,868,123 A | 9/1989 | Berson et al. |
| 5,846,816 A | 12/1998 | Forth |
| 6,827,036 B2 | 12/2004 | Connolly |
| 7,682,821 B2 | 3/2010 | Woods et al. |
| 7,824,904 B1 | 11/2010 | Dimanshteyn |
| 8,409,845 B2 | 4/2013 | Trent et al. |
| 8,507,264 B2 | 8/2013 | Lewnard et al. |
| 8,734,805 B2 | 5/2014 | Hentges et al. |

(Continued)

FOREIGN PATENT DOCUMENTS

| | | | |
|---|---|---|---|
| CN | 102134553 A | * 7/2011 | ............ C12M 27/20 |
| CN | 102134553 A | 11/2013 | |

(Continued)

OTHER PUBLICATIONS

Chi Qinglei,, English-machine translation of WO-2016054939-A1. (Year: 2016).*

(Continued)

*Primary Examiner* — Liban M Hassan
(74) *Attorney, Agent, or Firm* — Santangelo Law Offices, P.C.

(57) ABSTRACT

Embodiments of the present invention may provide fluid flow coordinators, passive flow field modifiers, or even inwardly protruding helical spines which can be used in continuous, scalable, low energy usage, bioreactor systems perhaps to provide optimal mixing of microorganisms with nutrients, gases, or the like or even to move microorganisms, such as algae, in and out of light for effective and optimal growth.

16 Claims, 44 Drawing Sheets

(56) References Cited

U.S. PATENT DOCUMENTS

| | | | |
|---|---|---|---|
| 9,102,923 | B2 | 8/2015 | Meiser et al. |
| 9,295,206 | B2 | 3/2016 | Jovine |
| 9,938,492 | B2 | 4/2018 | Gressel et al. |
| 2005/0260553 | A1 | 11/2005 | Berzin |
| 2008/0153080 | A1 | 6/2008 | Woods et al. |
| 2008/0316858 | A1* | 12/2008 | Gron ............ B01F 5/061 366/341 |
| 2009/0130706 | A1 | 5/2009 | Berzin et al. |
| 2010/0068801 | A1* | 3/2010 | Woods ............ C12M 21/02 435/292.1 |
| 2013/0109085 | A1 | 5/2013 | Woods et al. |
| 2014/0134672 | A1 | 5/2014 | Tuttman et al. |
| 2014/0186909 | A1 | 7/2014 | Calzia et al. |
| 2014/0315290 | A1 | 10/2014 | Mottahedeh |
| 2014/0329297 | A1* | 11/2014 | Longan ............ C12M 21/02 435/252.1 |
| 2016/0369216 | A1 | 12/2016 | Matsumoto |
| 2018/0223241 | A1 | 8/2018 | Zhongzhi He |

FOREIGN PATENT DOCUMENTS

| | | | | |
|---|---|---|---|---|
| ES | 2479340 | A2 * | 7/2014 | ............ F24S 23/80 |
| WO | 2004074423 | A2 | 9/2004 | |
| WO | 2016054939 | A1 | 4/2016 | |
| WO | WO-2016054939 | A1 * | 4/2016 | ............ B01F 5/06 |
| WO | 2020237103 | A1 | 11/2020 | |

OTHER PUBLICATIONS

Gomez et al., English machine translation of ES-2479340-A2. (Year: 2014).*
Perrine, et al., Optimization of photosynthetic light energy utilization by microalgae, Algal Research 1 (2012) 134-142, Accepted Jul. 4, 2012, 9 pages.
Advanced Algal Systems Technology Area, 2017 Project Peer Review, 110 pages.
Akhavan-Behabadi, et al., Pressure drop and heat transfer augmentation due to coiled wire inserts during laminar flow of oil inside a horizontal tube, International Journal of Thermal Sciences 49 (2010) 373-379, Accepted Jun. 14, 2009, 7 pages.
De Godos, et al., Evaluation of carbon dioxide mass transfer in raceway reactors for microalgae culture using flue gases, Bioresource Technology 153 (2014) 307-314, Accepted Nov. 30, 2013, 8 pages.
Xi Gao, et al., Comprehensive computational model for combining fluid hydrodynamics, light transport and biomass growth in a Taylor vortex algal photobioreactor: Eulerian approach, Algal Research 24 (2017) 1-8, Accepted Mar. 16, 2017, 8 pages.
Gunes, et al., Heat transfer enhancement in a tube with equilateral triangle cross sectioned coiled wire inserts, Experimental Thermal and Fluid Science 34 (2010) 684-691, Accepted Dec. 28, 2009, 8 pages.
Gunes, et al., A Taguchi approach for optimization of design parameters in a tube with coiled wire inserts, Applied Thermal Engineering 31 (2011) 2568e2577, Accepted Apr. 12, 2011, 12 pages.
Mooij, et al., Impact of light color on photobioreactor productivity, Algal Research 15 (2016) 32-42, Accepted Jan. 23, 2016, 11 pages.
Kong, et al., Light-Limited Continuous Culture of Chlorella vulgaris in a Taylor Vortex Reactor, Environmental Progress & Sustainable Energy (vol. 32, No. 4) DOI 10.1002/ep, Aug. 1, 2013, 8 pages.
Kong, et al., Enhanced Algal Growth Rate in a Taylor Vortex Reactor, Biotechnology and Bioengineering, vol. 110, No. 8, Aug. 2013, 10 pages.
Laws, et al., Photosynthetic Efficiency Optimization Studies with the Macroalga Gracilaria tikvihae: Implications for CO2 Emission Control from Power Plants, Bioresource Technology 37 (1991) 25-33, 9 pages.
Liu et al., A comprehensive review on passive heat transfer enhancements in pipe exchangers, Renewable and Sustainable Energy Reviews 19 (2013) 64-81, Accepted Nov. 5, 2012, 8 pages.

The National Alliance for Advanced Biofuels and Bioproducts (NAABB), Full Final Report Section I, Program Overview, 75 pages.
The National Alliance for Advanced Biofuels and Bioproducts (NAABB), Full Final Report Section II, Team R&D Overview, 99 pages.
The National Alliance for Advanced Biofuels and Bioproducts (NAABB), Full Final Report Section III, Individual Project Summaries Team R&D, Overview, 139 pages.
Olivares 2016 National Alliance for Advanced Biofuels and Bioproducts Synopsis (NAABB), 28 pages.
Fuentes et al., Outdoor continuous culture of Porphyridium cruentum in a tubular photobioreactor: quantitative analysis of the daily cyclic variation of culture parameters, Journal of Biotechnology 70 (1999) 271-288, accepted Dec. 22, 1998, 18 pages.
Promvonge, Thermal enhancement in a round tube with snail entry and coiled-wire inserts, International Communications in Heat and Mass Transfer 35 (2008) 623-629, Jan. 31, 2008, 7 pages.
Unkefer et al., Review of the algal biology program within the National Alliance for Advanced Biofuels and Bioproducts, Algal Research 22 (2017) 187-215, Accepted Jun. 1, 2016, 29 pages.
Sayre, Microalgae: The Potential for Carbon Capture, BioScience • Oct. 2010 / vol. 60 No. 9, www.biosciencemag.org, 6 pages.
Sheehan et al., A Look Back at the U.S. Department of Energy's Aquatic Species Program—Biodiesel from Algae, National Renewable Energy Laboratory NREL/TP-580-24190, Jul. 1998, 328 pages.
Tredici, Mario R Tredici (2010) Photobiology of microalgae mass cultures: understanding the tools for the next green revolution, Biofuels, 1:1, 143-162, DOI: 10.4155/bfs.09.10, 21 pages.
Coward et al., Utilising light-emitting diodes of specific narrow wavelengths for the optimization and co-production of multiple high-value compounds in Porphyridium purpureum, Bioresource Technology 221 (2016) 607-615, Accepted Sep. 22, 2016, 9 pages.
Vonshak et al., Mass Production of the Blue-green Alga Spirulina: An Overview, Biomass 15 (1988) 233-247, accepted Jan. 28, 1988, 15 pages.
Vonshak et al., The effect of light availability on the photosynthetic activity and productivity of outdoor cultures of Arthrospira platensis (Spirulina ), J Appl Phycol (2014) 26:1309-1315 DOI 10.1007/s10811-013-0133-1, Revised and accepted: Aug. 22, 2013, 7 pages.
Babcock et al., Hydrodynamics and mass transfer in a tubular airlift photobioreactor, J Appl Phycol, 14: 169-184, 2002, 16 pages.
Promthaisong, et al. Numerical Investigation on turbulent forced convection and heat transfer characteristic in spirally semicircle-grooved tube. International Journal of Mechanical and Materials Engineering (2016) 11:9, 15 pages.
Grima et al., Scale-up of tubular photobioreactors. J. Appl. Phycol. 12, 355-368, 2000.
Pulz, Photobioreactors: production systems for phototrophic microorganisms. Appl Microbiol Biotechnol 2001;57:287-93, 7 pages.
Hosseinverdi and Fasel, Laminar-turbulent transition in a laminar separation bubble in the presence of free-stream turbulence. (c) 2015 / Procedia IUTAM 14 (2015) 570-579, 2015, 10 pages.
Vonshak, Outdoor mass production of Spirulina: the basic concept. In: Vonshak A (ed) Spirulina platensis (Arthrospira): physiology, cell-biology and biotechnology. Taylor and Francis, Bristol, 1997, pp. 79-99, 22 pages.
Weissman, et al., Photobioreactor design: mixing, carbon utilization, and oxygen accumulation, 1988, Biotechnology and Bioengineering, vol. 31, pp. 336-344.
Almutairi, et al., Dynamics of laminar separation bubble over NACA-0012 airfoil near stall conditions. Aerospace Science and Technology 68 (2017) 193-203. Accepted May 9, 2017, available online May 15, 2017, 11 pages.
Lei, et al., Re-examination of the effect of a plane boundary on force and vortex shedding of a circular cylinder. Journal of Wind Engineering and Industrial Aerdynamics 80 (1999) 263-286, Aug. 31, 1998, 24 pages.
Hetsch and Rist, An analysis of the structure of laminar separation bubbles in swept infinite geometries, European Journal of Mechanics B/Fluids 28 (2009) 486-493, Mar. 12, 2009, 8 pages.

(56) References Cited

OTHER PUBLICATIONS

Tredici, M. R. (2004) Mass production of Microalgae: Photobioreactors. Handbook of Microalgal Culture: Biotechnology and Applied Phycology. Edited by Amos Richmond, 178-214, 37 pages.

Tulecke and Nickell, Production of Large Amounts of Plant Tissue by Submerged Culture. Science, New Series, vol. 130, No. 3379 (Oct. 2, 1959) 863-864, 3 pages.

Gudin and Chaumont, Cell fragility—The Key Problem of Microalgae Mass Production in closed Photobioreactors, Bioresource Technology 38: 145-151, 1991, 7 pages.

Wagner and Volgelmann, Cultivation of Plant Tissue Cultures in Bioreactors and Formation of Secondary Metabolites. Plant Tissue Culture and Its Bio-technological Application. Abstract Apr. 10, 2019. 4 pages.

Ogbonna, J.C. and Tanaka, H., Photobioreactor Design for Photobiological Production of Hydrogen. Institute of Applied Biochemistry, University of Tsukuba, Tsukuba, Japan. pp. 245-261.

Lee and Palsson, High-Density Algal Photobioreactors Using Light-Emitting Diodes. Biotechnology and Bioengineering, vol. 44, pp. 1161-1167 (1994).

Javanmardian, M., High-density algal cultures: Photobioreactor design and cell cycle kinetics. (c) 1991, 231 pages.

Pulz and Scheibenbogen et al., Photobioreactors: Design and Performance with Respect to Light Energy Input. Advances in Biotechnical Engineering/Biotechnology, vol. 59. (c) Springer-Verlag Berlin Heidelberg 1998. 30 Pages.

Miron et al., Comparative evaluation of compact photobioreactors for large-scale monoculture of microalgae. Journal of Biotechnology 70 (1999) 249-270.

International PCT Application No. PCT/US20/034097, filed May 21, 2020. First Named Inventor: Falco. International Search Report dated Aug. 25, 2020. 2 pages.

International PCT Application No. PCT/US20/034097, filed May 21, 2020. First Named Inventor: Falco. Written Opinion of the International Searching Authority dated Aug. 25, 2020. 10 pages.

\* cited by examiner sec. D sec. C sec. B sec. A

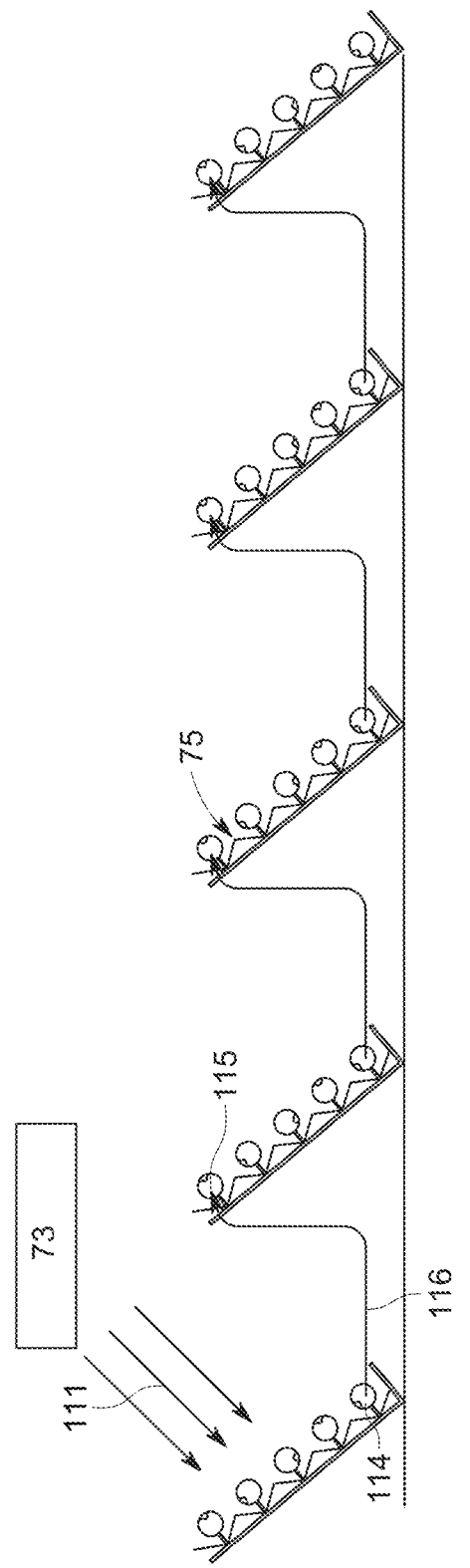

METHODS AND SYSTEMS FOR EFFICIENT BIOREACTOR MIXING AND LIGHT UTILIZATION EMBODYING LOW PROCESS ENERGY AND SCALABILITY

FIELD OF THE INVENTION

Embodiments of the present invention may relate to bioreactor and photobioreactor devices and methods for more efficient production of microorganisms via better use of light, generally better mixing, and even lower energy input. Some embodiments of the present invention utilize algae, which can be either phototrophic, mixotrophic, heterotrophic, or the like, but the philosophy underlying the various disclosed devices can be used to grow a wide range of microorganisms. Embodiments of the present invention may provide optimum use of light input, low shear stress, low bioreactor input energy, controlled feeding of $CO_2$ and nutrients perhaps along with gas removal, continuous production of the microorganisms (vs. batched production), or the like. Some aspects may include programmed, continuous prescribed feeding of nutrients, $CO_2$, $O_2$, light, sugars (such as with heterotrophic and/or mixotrophic microorganisms) and may even provide continuous removal of $O_2$, $CO_2$, or the like. Importantly, embodiments of the present invention may elucidate bioreactor design principles and even procedures that can be scaled from benchtop to commercial/industrial scales perhaps while keeping the microorganism (e.g., algae, etc.) productivity of much smaller bioreactors, and be economically viable.

BACKGROUND

The power generation industry is coming under increasing pressure to produce electricity from renewable energy sources. Many biofuels meet renewable energy source standards, however, sources of conventional biofuels, such as biomass, biodiesel, and bioethanol, and biogas may not be uniformly distributed geographically across the nation and the world, and in general, these sources may not be located close to power generation facilities. At the same time, reductions in carbon dioxide emissions and other gas emissions from various sources are becoming increasingly necessary and/or desirable. In addition, the imposition, or even potential imposition, of carbon taxes could make carbon capture and utilization even more economically desirable. Typically, capturing carbon dioxide from the flue gases of anthropogenic sources, such as electric power plants, and then sequestering them may be expensive, and the long-term outcome may be uncertain (e.g., the earth may shake and may eject the gas out again, underground contamination of water supplies, etc.). On the other hand, photosynthesis is nature's way of recycling carbon that is in the biosphere. In this process organisms performing photosynthesis, such as plants, may synthesize carbohydrates, proteins, oils and other cellular materials using sunlight and $CO_2$. One of the most efficient converters of $CO_2$ to biomass is microalgae (e.g., when using solar energy in the presence of nutrients). Algae may be the fastest growing photoautotrophic organisms on earth, and may even be one of nature's simplest microorganisms. In fact, over about 90% of $CO_2$ fed to algae can be absorbed, mostly such as through the production of cell mass.

Using algal biotechnology, $CO_2$ capture can be advantageous due to the production of useful, high-value products whose productivity may be enhanced from the use of $CO_2$ that could otherwise be emitted as a waste gas into the atmosphere that contributes to global warming. Production of algal biomass as a method of reducing $CO_2$ levels in combustion gas may be an attractive concept because dry algae may have a heating value roughly equivalent to coal. Furthermore, algal biomass can also be turned into a high-quality liquid fuel which may be similar to crude oil through thermochemical conversion by known technologies, such as High Temperature Liquefaction (to do this economically can require supplies of waste heat and low-cost electricity), or diesel fuel (e.g. biodiesel) via the transesterification of the algal biomass's lipids. Algal biomass also can be used for gasification to produce highly flammable organic fuel gases suitable for use in gas-burning powerplants.

Algal cultures also can be used for biological nitrogen oxides ("NOx") removal from combustion gases. Some algae species can remove NOx over a wide range of NOx concentrations and combustion gas flow rates. Nitrous oxide (NO), a major NOx component, may be dissolved in the aqueous phase, after which it may be oxidized to NO and assimilated by the algal cell. For example, NOx removal using the algae, *Dunaliella*, can occur under both light and dark conditions, perhaps with an efficiency of NOx removal of over about 96% (such as under light conditions). Over an 18-year period, the U.S. Department of Energy (DOE) funded an extensive series of studies to develop renewable transportation fuels from algae. In Japan, government organizations (MITI) in conjunction with private companies, have invested over $250 million into algal biotechnology. Each program took a different approach, but because of various problems addressed by certain embodiments of the present invention, there has been little large scale commercial success to date.

An additional valuable use of algae may be to produce fish food. The need for fish farms may be rapidly increasing, and the availability of fish used to feed other fish such as salmon, or the like, may be decreasing. Thus, many farms use soy and other vegetable protein for feed, but these substitutes do not contain the omega-3 fatty acids that make these farmed fish as valuable a food. Algae has these fatty acids and thus, is a valuable fish food.

In addition, algae are capable of growing in brackish and even saline waters that may be unsuitable for agriculture. This may enable all the advantages of algae production perhaps without incurring a serious water usage problem.

A major obstacle for feasible algal $CO_2$ capture, and perhaps even pollution abatement has been the lack of an efficient, yet cost-effective, growth system. DOE's research focused on growing algae in massive open ponds as big as about 4 $km^2$. As recently as 2016, the National Algal Biofuels Technology Review Final Report (a major 3-year U.S. government funded program) concluded that, "Cultivation of algae in algal raceways and open ponds is envisioned as the most economical route for algal biomass and biofuels production. In the coming decades, if the projected scales of biofuels are to be generated, algae have to be cultured in several thousand acres of land for the desired biomass yields." This resulted from examining many closed photobioreactor designs. Basically, the raceway ponds may require low capital input; however, algae grown in open and uncontrolled environments can result in low algal productivity perhaps due to contamination with environmental predators and even competing, slower growing species. Occasionally, sudden pond death was experienced. The open pond technology made growing and harvesting the algae prohibitively expensive, because the movement of massive amounts of dilute algal waters may have required very large agitators, pumps, and collectors, etc.

To reduce the above effects, major work has been done to examine and even understand the nature of biotic factors such as bacteria, viruses, invasive algal species, fungi, and even herbivores in algal ponds that may impact the algal biomass yields, and some progress has been made.

But, a major issue with these raceway ponds has not been addressed. As the raceway ponds get larger and larger, very significant portions of the flow may not experience the turbulence imparted by the paddlewheels, and thus do not mix well, or worse do not mix at all, and thus grow slowly. As Tredici (2004) notes, "the long-term productivity in large commercial raceways rarely exceed 12-13 g/m^2/d", while laboratory sized ponds have reached 40 g/m^2/d. Our understanding of this is that the lower productivity is because the paddle wheel turbulence decays in about twenty paddle chord lengths downstream from the paddle, so that during the remaining time of passage around the raceway, which could be large (90% or so in the 4 km2 raceways) the algae are not being mixed, so that the algae near the water surface, after the turbulence dies, would get all or more sunlight than the cells require, and as the algae greens up with its growth it will shade the algae below it from getting the light these cells need. Thus, a large fraction of the algae which exists below the water surface may not optimally grow because of lack of sufficient light. In addition, the lack of movement of the algae near the surface may create additional problems. According to Tredici (2004), "Outdoors, under full sunlight, the photosynthetic efficiency drops to one tenth—one fifth of the values observed at low irradiances. The major causes for this inefficiency are the light saturation effect (LSE) and photoinhibition, phenomena that strongly limit the growth of microalgae in outdoor culture. The main problem is that photosynthetic apparatus of phototrophs saturates at low irradiances and that, at irradiances above saturation, the absorbed photons are used inefficiently, generate heat, and may cause cell injury. Several strategies to overcome the LSE and photoinhibition have been proposed, based on engineering (light dilution, ultra-high cell density culture, high turbulence), physiologic (photo acclimation, nutrient deprivation) or genetic." These approaches (perhaps except for some genetic possibilities) may result in limiting the potential maximum growth of the algae, and hence other approaches are needed.

Thus, perhaps because of the lack of mixing, the yields from commercial/industrial size raceway ponds may always be lower than yields obtained in small laboratory raceway ponds, where the duration of time after the turbulence decayed to when the algae circulates back to the paddle wheel and is mixed again by the turbulence created, may be much smaller.

Furthermore, with low algal productivity and large flat-land requirements, this approach could, in the best-case scenario, be applicable to only about 1% of U.S. power plants. Looked out another way, Laws and Berning (1991) point out that, "If 20% of the $CO_2$ presently emitted by coal-fired power plants in the US were used to grow algae, an area of land equal to roughly 1% of the area of the United States would be required for the growth of algae." Coal use has dropped since then and a substantial number of plants have been replaced by natural gas, but the enormity of the land needs remains. Almost two decades later Sayre (2010) reanalyzed the algae growth story in raceway ponds and concluded from the perspective of individual coal plants that "a pond of approximately 7000 acres in size would be required to capture 80% of the $CO_2$ emissions from a 200-MWh coal-burning power plant during the day." Again, a massive use of land—likely more than is available around many industrial plants. Thus, a different approach to industrial scale algae production is needed.

The Japanese MITI approach, with stricter land constraints, focused on very expensive closed algal photobioreactors utilizing fiber optics for light transmission. In these controlled environments, much higher algal productivity was achieved, but the algal growth rates were not high enough to offset the capital costs of the systems utilized.

The new approaches must overcome the limitations confronting the industry today which may include the overall low area yields (or even yields per unit area) which may fall short of the theoretical maximum and those associated with scaling up microalgal culture to commercial size. Yet, as recent as 2016, the National Algal Biofuels Technology Review Final Report is still advocating raceway ponds.

In the past, attempts have been made to scale up enclosed photobioreactors to industrial/commercial scales. As with the open raceway ponds, the key problem to solve may be the mixing/light input which are needed to uniformly grow the algae in these large volume systems.

Current bioreactor systems may fall into six classes: (1) open raceway ponds; (2) stirred enclosed mixing vessels; (3) arrays of vertical tubes through which bubbles of $CO_2$ (or air) float up and can be used to move the algae, or other microorganisms, into and out of the light near tube walls, as well as to feed the algae; (5) bags through which $CO_2$ may be bubbled for the same reason, or even (6) recirculating pipe flow systems. A few may involve tanks with growth medium (e.g., fabric) hanging into water. These fabrics may be brushed clean to harvest the algae that grows on them. And, even short tubular reactors with mechanically turned mixing vanes in them. These systems may be considered batch process reactors.

As early as 1959, Tulecke and Nickell, and in 1963 by Wang and Staba, produced 20-liter bioreactors for the culture of plant cells. In the early 1970's, Kato and his colleagues at the Japan Tobacco and Salt Public Corporation investigated the use of air in mixing up to 1500 liters. Later, a 20,000-liter system was used by Noguchi at the same corporation. In the mid-1980's, Wagner and Vogelmann demonstrated that the airlift system was superior to all others in providing good productivity and a well-defined and controlled system of parameters, resulting in reproducible flow characteristics. They further suggested that fluid movement can be better controlled through the use of an internal draft tube through which the air mixture may be bubbled. Although such systems can be scaled up significantly, their operation may require much external energy and may not be cost effective for use as production systems for biofuels. In addition, mutual shading in vertical airlift systems may have an impact on the total installed system capacity in a given footprint.

As noted above, airlift reactors may typically consist of vertically oriented concentric tubular containers, in which the gases may be bubbled in at the bottom of the inner tube. The pressure gradient created at the bottom of the minor tube creates an annular liquid flow upward through the inner tube and then downward between the tubes. The external tube may be made out of translucent material, while the inner tube may be opaque. Therefore, the algae may be exposed to light while passing between the tubes and may be exposed to darkness while in the inner tube. The light-dark cycle may be determined by the geometrical design of the reactor (e.g., height, tube diameters, etc.) and by operational parameters (e.g., gas flow rate). Airlift bioreactors can have higher mass transfer coefficients and algal productivity when compared to conventional mechanically stirred systems. But analogous to mammalian cell production, large bubbles may result in poor mass transfer of critical gases. Bubbles that are too small may result in greater shear near the point of bubble creation and, therefore, more algal cells may be damaged or even killed. Both damaged and even killed cells can release components into the growth medium, that if too high, can greatly impact the health and thus the productivity of the system. However, control over the flow patterns are difficult or even impractical within a very large airlift bioreactor. The energy requirement for an airlift photobioreactor may be lower than that for a stirred system and may be suitable for higher value products than commodity transportation fuel, but even then, the pumping costs required for an airlift photobioreactor may be too great for low value commodity transportation fuels, or biocoke, and fish food, as examples, or the like.

Another type of photobioreactor that may be used in research projects is the bubble column bioreactor. Bubble columns can be translucent, large diameter vertically oriented containers filled with algae suspended in liquid medium, in which gases may be bubbled in at the bottom of the container. A key limitation of bubble columns may be that they are inherently batch processes. Furthermore, U.S. Patent App. US20080153080 notes that, "precisely defined flow lines are not reproducibly formed in very large systems, it can be difficult to control the mixing properties of the system, which can lead to low mass transfer coefficients, poor photo modulation and low productivity."

Complete mixing may be an important aspect of microorganism growth in all photobioreactors, but is not achieved, no matter what the scale. Complete mixing may require that the cells are moved across all of the scales of the photobioreactor, thus across from photic zone to the dark zone and back to the photic zone, as well as containing motions on microscales to enable full utilization of nutrients and $CO_2$. Javanmardian and Palsson (1991) developed an equation for the depth of light penetration—for the extent of the photic zone in any photobioreactor ("PBR"). Applying this equation to a high-density pond system suggests that at cell densities of 50 g/L, light penetration would be less than about 2 mm. This demonstrates that light penetration may limit algal biomass production in typical open pond situations. Ogbanna and Tanaka (1997) demonstrated that photosynthesis may be maintained with a light intensity of 7.3 micro moles/m2/s. Thus, when the light entering a PBR may be attenuated to this level, it may be considered to be the extent of the photic zone. In addition, Lee and Palsson (1994) found that both light path and light intensity may increase algal biomass production with light path perhaps having a greater impact. Thus, a mixing protocol which can efficiently get the algae cells into and out of the photic zones may be essential to having a productive photobioreactor.

Past attempts at improving photobioreactors to achieve better light availability perhaps at a scale larger than defined by about 2 times the photic zone have not succeeded without excessive use of energy, excessive shear stress on the algae, excessive maintenance, or the like. Tredici (2004) seemed to have reviewed all then known photobioreactors, including his own group's experiments, and showed that pipe-type PBRs could roughly produce about 50% more biomass per m^2/d than raceway ponds, or approximately 1.5* 12.5=18.75 g/m^2/d—this is under naturally occurring turbulent mixing. Flat Plate PBRs produced more at around 25-28 g/m^2/d. In general, he concluded that flat plate bioreactors may have the most promise for scaling up. But these batch type production processes are not easily scalable to the sizes needed.

Some of the highest reported algae productivities may have come from laboratory size raceway ponds (about 40 g/m^2/d) and even carefully orientated flat plate PBRs (about 28 g/m^2/d).

Looking back to the raceway pond BR/PBR, Mottahedeh in U.S. Pat. App. US20140315290 A1 attempts to improve their output perhaps by covering a raceway pond. Although many of the contamination and even evaporation issues may be removed, the mixing problem has not been solved. He attempts to address improving mixing by creating wave motion in his raceway. However, particle motions excited by waves may decrease exponentially as an observer moves below the water surface, so algae deeper in the raceway channel may not be mixed.

Another type of bioreactor includes a tank type bioreactor. For example, U.S. Pat. No. 5,846,816 may disclose a triangular cross-sectional tank, in which an internal mixing may be driven by a jet of gas forced up through an apex which may be on the bottom of the tank. Even with recirculation, the closed cell type motions will not bring the algae held in the recirculation cells close to the walls to receive light. Systems such as these seem to put high shear stress on the microorganisms, they require high energy input, they may be expensive to build, and seem to be batch processes. U.S. Pat. No. 7,824,904 may provide a tank with paddles that can stir the algae. In particular, sets of double counterrotating paddles with artificial lighting in them may provide light to the algae. These type of photobioreactors have at least three drawbacks when considering scaleup: a) they may require a lot of energy to keep the fluid moving; b) they may be essentially batch processes, perhaps with each batch being a small fraction of the needed algae; and perhaps even c) these processes may be very costly, high maintenance systems.

Other examples of closed photobioreactors may include U.S. Pat. Nos. 2,732,663; 4,473,970; 4,233,958; 4,868,123; and 6,827,036.

Burlew (1961)—provides an overview of algae bioreactors. These may include glass tubes, open tanks, open trenches, and perhaps even covered trenches. In these systems, carbon dioxide may be fed into a liquid perhaps via gas sparging. More recently, Pulz (1998) may have reviewed algae photobioreactors, and Richmond 2004 may have reviewed the general state of the art of microalgae culturing, including reactor design. Both references (Richmond 2004 and Pulz 1998) note that open systems, such as natural lakes, circular ponds, and raceway reactors may be the predominate commercial technology. Examples of open-air systems used for cultivation of algae may be found in U.S. Pat. Nos. 3,650,068; 3,468,057; and 4,217,728. All of these are subject to the limitations discussed above.

In the past photobioreactors have attempted to provide an appropriate mixing using turbulent flow. These have failed to provide enough energy at mixing scales that are the order of the bioreactor's boundaries. Increasing the flow speed attempts to improve the mixing on these large scales but may be very inefficient since excessive energy may be needed to drive the flow. Thus, photobioreactors tend to be small diameter pipe flow photobioreactors, of diameters from about 1 to about 5 cm, that may enable most of the algae in these pipes to see some light (e.g., to, at least, be in the weak side of the photic zone) when the incident light may be very intensive, even if the turbulent motions don't carry the cells to the walls. Practitioners using these bioreactors attempt to create enough energy in scales of motion which carry cells across the bioreactor flow, perhaps by moving the mean flow at a fast speed. Since the energy in the large-scale turbulent motion may increase linearly with mean flow speed, this does increase the energy in the large scales but, because of the nature of turbulence, the flow increase creates very little additional energy in the large scales. Thus, an uneconomical amount of energy may be needed to drive the mean flow to create the desired energy in these cross-flow scales. Furthermore, the high speeds needed also create cross-flows may create high flow related shear, that may be harmful to many algae cells. As will be discussed herein, embodiments of the present invention provide these needed scales very efficiently, perhaps with very little flow shear, and even at remarkably slow flow speeds.

In the case of raceway ponds, most may have their surface exposed to the air (even if in tents or greenhouses), where contamination can easily occur, which sometimes may lead to an alga kill, or at the minimum, slow growth, or the like. In addition, if the intent is to have the algae utilize concentrated $CO_2$, these devices may be inefficient in holding the gas in the water until it may be used by the algae. Furthermore, evaporation of the water may occur. In any case, it may take days for a flow to be circulated around the ponds and pipes or in the bags and cylinders until the algae has grown enough to be harvested. Algae grown in enclosed mixing vessels, usually heterotrophically (without light) may need to be batch feed, and again after the period of time required for full growth, the process may be stopped, the algae may be removed, and the vessels may need to be cleaned out.

In terms of scale of these algae production devices, pipe-type flow systems must be small enough in diameter to allow the ambient light to get to the algae flowing near the center of the pipes, as natural turbulence may not produce sufficient mixing to supply light to many of these cells. Similarly, raceway pond depths may need to be shallow enough to enable light to penetrate into the bottom of the ponds. This has practically restricted the size of these pipes to a couple of inches in diameter, and the depth of the ponds to about 4 to about 8 inches, and the width of the bags to a couple of inches, or the like. In addition to red and blue light penetration in water decaying exponentially, as algae matures and greens up, the algae nearest the wall of the PBR may shade the algae further in, so that even less light may be available. Light penetration through almost fully growth algal cultures can be as little as a millimeter. The inherently small scale of these systems and their inherently batch flow nature may severely limit the option to be used as waste converters of industrial processes which may have continuous, large output.

One of the problems associated with poor algae development and even poor growth rates in all photobioreactors, whether laboratory or commercial, may be tied to the amount of time an algal cell spends in the photic zone, and the amount of time it may spend outside of the photic zone. Again, the photic zone may be that in which the incident photon flux may be great enough to trigger photochemistry in the microorganism.

An example of the complexity of the response of algae to growth conditions is illustrated in Richmond (2004). "Under controlled lab conditions, it is possible to accurately adjust cell density to the intensity of the light source. Providing this adjustment is made and care is taken to eliminate conditions or substances which inhibit cell growth, the algae called *Spirulina* sp. responds positively, i.e. with increased output rate of cell mass, to each increment of additional irradiance up to 4000 micro moles/m^2/s (applied on each side of a flat plate in an flat plate reactor 1.4 cm across). The same effect was obtained with the algae *Chlorococcum littorate* grown in 1 cm optical path flat plates. The OCD rose steadily in response to increasing light intensity from 120 to 2000 micro moles/m^2/s, but without any loss in light-use efficiency: A flux of 360 micromoles/m^2/s resulted in ca. 50 mg/l/h, and 2000 micromoles/m^2/s yielding 400 mg/l/h, or 400*24=9.6 gm/l/d. But, in stark contrast, Molina-Grima et al. (1997) found in their system a steady decrease in quantum efficiency as the PFD rose from 820 to 3270 micromoles/m^2/s. The inability of that system to utilize successfully high irradiance was seen in that each rise in the intensity of the light source and the dilution rate resulted in increased light/cell (from ca. 6 to 62) and although areal productivity increased initially in response to increased irradiance (i.e. from 821 to 1620 micromoles photons), it decreased when the culture was exposed to 3270 micromole photons/m^2/s. There is no simple explanation for the disagreement between these results." Richmond (2004)

Two timescales may be involved in the photosynthetic reaction, the light reaction time, which may be the order of nanoseconds to microseconds, and the dark reaction time, which may be of the order of about 1 to about 15 milliseconds. The first timescale may be so short that the light reaction may be considered instantaneous, hence the photosynthetic reaction center turnover time may be essentially equal to the dark reaction time.

But, in any photobioreactor, there may be an additional timescale that may be important to the overall growth rate of the algae. It may be the algae cell travel time into and out of the photic zone. A photic zone may be the region in which there may be enough light to enable photosynthesis; it may extend from the wall of a photobioreactor into the algae suspension at a distance that may depend on the density of the algae. The cell travel-time, may be the average time required for cells to move back and forth between a photic zone and the dark regions interior of the reactor. The speed of these motions, and therefore the cell travel-time, may be difficult to measure. But, two extremes can be estimated. If, ideally, a cross-flow velocity could be generated in a PBR, that could bring cells across the optical path of the bioreactor to its walls, it could represent the shortest possible travel time for an algae cell to get across the dark zone to the photic zone. This could be a motion of the scale of the cross-flow dimension of the bioreactor. If this motion had velocity u, then the time to cross the reactor of dimension D would be D/u. On the other hand, in a turbulent flow there may be eddies of all scales of the PBR. If we use as a representative velocity of the turbulence energy the so-called turbulence intensity, or the rms intensity of the spectral distribution, then properly normalized, this measure may not depend on what generated the turbulence. These cell travel times could be much greater than the hypothetical directed cross-stream velocity we discussed above. Richmond (2004) hypothesizes that the cell travel time could be about 30 times longer than the time associated with the directed cross-stream velocity. Creating a significant shortening of the algae cell time in the dark zone could be an important contributor to the efficiency of a photobioreactor, and may be responsible for the differences in the results described above. Of course, if there may be very little turbulence, as is the case greater than about 20 blade diameters downstream of the paddle wheels in raceway ponds, then the algae in the dark zones may remain there for a much longer time.

A directed cross-flow could take mechanical input of the types just mentioned. However, embodiments of the present invention create directed cross-flows, on top of natural turbulence. These cross-flows may not be controlled as precisely as, say, an array of jets emanating from the walls of the pipe-type BR/PBR all around the circumference and all along the length of the pipe (which may be economically impractical concept for a PBR), for example, but we can essentially generate the needed cross-flows, whose goal is to shortening the time algae spend in the dark zone, and to decrease the time spent under high light input at the walls so as to reduce possible photobleaching.

Current commercially working closed pipe-type photobioreactors for algae are used to grow algae that create high value products such as nutraceuticals, chemicals, antioxidant astaxanthin, and the fatty acid omega-3. These typically have pipe diameters around 50 mm and have volumes and run at mass flow rates which may be much smaller than would be useful to handle industrial scale waste mass flow rates. Past studies of algae cultured in photobioreactors may have used narrow-bore tubes arranged in parallel, perhaps being horizontal to the ground and on racks. These may contain feed and harvest points to produce the biomass and may require large surface area to volume ratios. In addition to utilizing high velocities, these systems may often rely on churning provided by pumping the biomass/growth medium through the piping which may be partially full (e.g., and thus may have a free surface). Some mixing may occur perhaps because of the waves at the free surface (but as mentioned earlier, particle motions below surface waves move in circles that decay exponentially as one moves down from the free surface), and additional light can get to the algae, but the downsides may include that high shear stresses may be associated with the air-water interface, and the photobioreactor tube volume cannot be fully utilized. The cost of pumping in these systems should preclude them from being used in the production of biofuels on a large scale. Such systems are also not practical on a very large scale such as covering hundreds, if not thousands of hectares perhaps due to the high costs which primarily result from the need to push the fluid through the pipe at high velocity, and even the use of a very large number of these small pipes, with their attendant connections, fittings etc. There are also high costs because the pipes should be able to withstand the pressure created by the high-speed flows. Another cost may include the maintenance of so many 'live' joints. Also, the shear that an algal cell may experience at the free surface may be higher than in the interior of the liquid flow, which may cause stress reactions, chemicals released into the flow, and perhaps even death of some of the cells, or the like. This, of course, may limit the type of alga that can be grown, and the productivity of the process for any given algae.

To produce a large mass of microorganisms, a large volume reactor may be needed. As described above, the fraction of algal mass may be the order of a few percent of the volume of water it is in. If small pipes may be the basis for the bioreactor, then a very large number of small pipes may be needed to attain the required volume. As noted above, the need for small diameter pipes may be intimately associated with the need to thoroughly mix the microorganisms with their growth media, and, if phototrophic or even mixotrophic algae are used, they may need to at the same time be exposed to light, perhaps with a consistent light/dark duty cycle. To move the fluid through these pipes fast enough to provide turbulent mixing, a large amount of pumping power may be needed per unit length of the pipe (drag $\sim V^2$, and the pumping power is $\sim V^3$, where V is the mean velocity). However, this can't be accomplished for several reasons. First, the friction needed to be overcome by the flow moving fast enough to maintain strong turbulence, and thus have a reasonable amount of mixing, may be large. Second, the longer the pipe is, the greater the pressure drop that a pumping system must overcome. To keep the flow turbulent is a consequence of the Reynolds number $R=UD/nu$. For turbulent flow, R should be above R>2000 for industrial roughness pipes (note that glass pipes may require some roughness added). Thus, as the diameter increases, the speed can go down in proportion to the increase in pipe diameter (assuming the same temperature, and therefore constant kinematic viscosity, nu). So, it appears that as a pipe gets larger, the flow can move more slowly and the turbulence could persist. Thus, to meet the needs of the energy required to drive the flow, larger pipes may be indicated, just from the necessity of maintaining turbulent flow. But, of course, in a photobioreactor, as we have as noted, the problem of bringing the alga to the light, using the motions created by turbulence, may increase as the pipe diameter increases, and it may become a limiting factor to scaling up.

If a cross-flow velocity could be created by some mechanism, another benefit of a larger pipe and lower speed could be that the shear stresses exerted on the microorganisms could be less. This may enable a greater growth rate, as more microorganisms should survive the flow.

But larger scale continuously processing pipe-like bioreactors have not been successful perhaps because of the inherent nature of the motions in a turbulent flow. Unfortunately, the energy in the large scales of motion of a turbulent flow is a small fraction of the total energy that may be put into the turbulence by the mean flow instabilities when the Reynolds number of this flow may be high enough to create turbulence. Since the turbulence spectrum remains largely self-similar, if the Reynolds number is kept the same as the pipe diameter increases, the energy in the turbulence could overall decrease (e.g., the turbulence energy is proportional to the mean flow, U, in the pipe), the flow speed in the large eddies could thus decrease, and hence the time it takes for any microorganisms to traverse the radius of the larger pipe will increase (distance is larger (the path is random) and cross-flow velocity is smaller). This means that a microorganism that is near the center of a pipe, especially a large pipe, should not have a strong probability to be transported to the walls of the pipe with reasonably rapid frequency to be exposed it to the light it needs to grow at an acceptable rate. Furthermore, the light it formerly may have received in the interior of the bioreactor could, unfortunately, be obscured by the growth of microorganisms near the walls of the pipe as it may proceed down the length of the pipe. Thus, as we have noted, photobioreactors to date have been keep to scales small enough that light can penetrate deep into the center of the pipes. These small pipe systems rely on bringing the light to the alga, because of the low cross-flow intensity of the turbulent eddies.

Here we review two examples of scaled up pipe-type photobioreactors that were unsuccessful. They illustrate the inability of turbulence (produced in a smooth pipe flow at high enough Reynolds number), by itself to move the algae that may be in the dark zones to the photic zones frequently enough to create the growth rates desired. The first is the Aquasearch Inc. pipe system in Kailua-Kona Hi. The pipes ranged from about 7.08 inches to about 16.1 inches in diameter, and was run over a Reynolds number range of about 2,000-200,000. At best it achieved areal productivity of about 13 g/m^2/d. The, volumetric productivity maxed out at 0.052 g/l/d. Our second example of a scaled-up pipe-type photobioreactor is the one built by Hidrobiologica SA (Argentina). It consisted of about 10-inch diameter pipes laid parallel to the ground. The tubes were only partially filled and the culture was circulated at about 6-10 cm/s. This system was able to achieve about 0.2 g/l/d (approximately 24 g/m^2/d). Initially a sustainable output, which may in some ways reflect the presence of secondary flows in the elliptical shapes (35 cm wide×9 cm high) of the flexible pipes. This may be another way to introduce large scale secondary motions. The secondary flows seemed very slow. However, it did not produce the cross-flows needed to move the algae into and out of the photic zone.

Mixing mechanisms can present a challenge in a bulk bioreactor and can be problematic perhaps once the cells pass from the mixing area of the bioreactor to the solar collection tubes where photosynthesis may occur. A challenge to scale-up in photobioreactor systems may include the increased shear stress from the high intensity mechanical mixing motions and even high intensity turbulent induced motions that can result in cell damage. Cells may often be more resistant to static hydrodynamic shear and may be less resistant to shear created by a liquid/air surface. Cell damage and lysis can occur at several points, including bubble creation, bubble rising and, perhaps as for mammalian cells, bubbles bursting at the liquid/air interface, or the like. Plant cell walls may contain cellulosic material that may give them high tensile strength but may have extremely low shear resistance. The use of fixed blade impellers and even excessive airflows in airlift bioreactors may produce high shear rates that can result in cell breakage. The optimum level of turbulence for mixing, which may create high shear stress for cells, may be a result of fluid flow and even gas velocity. As the cell density increases, the viscosity of the fluid rises, which may work against uniform mixing of, and even subsequent optimum mass transfer of, nutrients, $CO_2$, or the like. High airflow rates at high cell densities in an airlift bioreactor can result in shear becoming too great and cell breakage may occur. Algae, similar to other species of plants in a suspension culture, may vary in the resistance to shear. This may be part of the challenge in developing a standard photobioreactor in which all cells can be grown.

Existing rotating, or shaking, or bubble forcing function bioreactors may not be feasible scaled up to provide consistent mixing and may use a high amount of energy and even maintenance needed to drive these flows. Thus, all of these proposed techniques may be limited by the scale of their forcing functions. Both the power to operate these large-scale bioreactors and the capitol costs of them may be economically prohibitive.

A further issue with increasing turbulence levels produced by increasing fluid speeds may be that most of the energy in a turbulence energy spectrum is in scales that may be significantly smaller than the geometric scale of the bioreactor geometry. In the case of a pipe, the peak in the energy spectrum may be about ⅕ of the pipe diameter. Energy in these scales may be transferred to smaller and smaller scales, and very little, if any, gets transferred to larger scales. Ideally, a device is needed that can produce mixing on scales of a photobioreactor dimensions, and contain only enough energy in the smaller scales to produce the mixing needed for the necessary transfer of $CO_2$, nutrients, or the like. The energy that natural pipe turbulence may create goes into these small scales—which as noted above could produce damaging shear—but ideally a mechanism needs to be developed that produces energy on larger scales that can convect the cells from the center of the pipe to the light at the photoreactor boundaries. Microorganism cells should be convected into and out of region of light to enable efficient photosynthesis. The problem is that the naturally occurring distribution of energy in the turbulence of a pipe-type duct flow can't be manipulated by flow speed changes, or area changes, to change the shape of its energy spectrum.

In the discipline of heat transfer, the industry seems to have developed ways to enhance the heat transfer from or even to fluid flowing in a pipe. These applications may extend from boilers to cooling towers. Heat transfer may emphasize moving the heat energy from the immediate vicinity of the walls (perhaps towards the walls or away from the walls). As a result, a pipe inner surface may be grooved, perhaps having a superficial resemblance to some embodiments of the present invention. However, there are major differences in the shapes, scales, and resulting flow field modifications from the heat transfer systems as compared to the systems described herein.

There is a need for producing the correct amount of mixing without damaging the microorganism cells, without using excessive energy, and perhaps even without allowing grown cells from shadowing those that need light. Embodiments of the present invention may provide scales of motion that take microorganisms that have grown and that may be blocking light coming from the outside from entering the bioreactor, or blocking light from LEDs inside the bioreactor, from getting to microorganisms more than a few millimeters away, that continue to need light to grow.

SUMMARY OF THE INVENTION

Embodiments of the present invention provide technology and methods and apparatus that can efficiently grow microorganisms perhaps on a large scale and even in continuously producing bioreactors.

As discussed above, there may be a compelling need to grow microalgae and other microbes in a protected environment, on a large scale, while using minimal energy input for the production of food, fuel, nutraceuticals and renewable chemicals. Briefly, particularly urgent non-limiting examples of this need may involve the growth of microorganisms on a scale consistent with the scale of production of industrial wastes such as $CO_2$, perhaps so that the biomass resulting from their growth using the $CO_2$ can be converted into useful products. Many industrial processes run continuously, such as coal fired electrical generating power plants, natural gas electrical generating plants, steel mills, concrete factories, ethanol refineries, or the like, and thus batch processing their wastes may not be a suitable solution. In all of these cases the effluent consists of massive amounts of $CO_2$ (about 10 to about 15% percent of the effluent), which for a 500 MW supercritical coal plant can amount to 21,900,000 pounds of CO2 per day! If the need is to be met, a continuous flow bioreactor and its ancillary plant may need to convert the continuously emitted very large mass flow of $CO_2$ into fuel, chemicals and possible food supplements. The needed bioreactor should be very robust, as interruptions from the death of the microorganisms may cause failure of the system's carbon utilization, and therefore introduction of the carbon into the atmosphere. For optimum performance (which may be equivalent to the greatest growth rate of the microorganisms with the right internal composition—carbohydrates, or lipids, or proteins) the needed continuous flow bioreactor could be capable of generating and maintaining an optimum degree of mixing over many length scales. Of particular interest may be to impart as much energy in scales the order of the bioreactor scale to bring the microorganisms into contact with light at the photobioreactor's boundaries (if photosynthesis is to be accomplished) using as little of the energy required to create the overall flow as is possible. If mixing can be achieved more efficiently than by having to increase the intensity of naturally occurring turbulence, less energy could be needed. The energy decay of these large scales is known to be slower than that of small scales.

Embodiments of the present invention may provide a new closed duct-type bioreactor/photobioreactor (BR/PBR) that may enable the fast growth of microorganisms in continuously producing BR/PBRs on any scale from laboratory to industrial/commercial, perhaps using minimal energy input. Various embodiments may provide scalability perhaps by using passive, stationary, non-rotating, non-pulsating, low shear stress producing, fluid mechanical mixing mechanisms that may produce fluid mixing on all scales such as may be necessary to have efficient contact of microorganisms with nutrients/growth media, effective exposure to light in appropriate light/dark duty cycles for various phototrophic organisms, and perhaps even efficient contact with $CO_2$ when needed, that may require lower energy input than traditional BR/PBRs to drive the flows. Scalability may enable better growth of phototrophic, heterotrophic and mixotrophic microorganisms perhaps for drug and nutraceutical development, as well as better growth of microorganisms such as algae and cyanobacteria used to handle large mass flows of $CO_2$ effluent from industrial smokestacks, and furthermore, better performance in wastewater treatment scenarios, perhaps so that effluents can be bio-remediated and converted into useful products. A continuous process may provide precise feeding and/or light exposure requirements as may be needed to optimize micro-organism growth rates and even chemical processes. Large scale, continuous flowing, low energy requirements of these BR/PBRs may be consistent with the nature of production of gaseous and liquid effluents emanating from many industrial processes. Of course, the PBRs may be adapted to a quasi-continuous process such as if dependent on sunlight only. Like all closed bioreactors, the nature of the new BR/PBRs may remove contamination issues and may prevent escape of $CO_2$ and even 02. Low energy inputs and even low maintenance design should contribute to economic viability of growing algae for fuels monetizing $CO_2$ flue gases, cleaning wastewater, or the like. Some of these characteristics may remove many of the limitations of current microorganism BR/PBRs. Embodiments of the present invention may be constructed with low cost materials and fabrication techniques.

It is therefore a goal of certain embodiments of the present invention to provide a device that may continuously mix algae, perhaps bringing and taking the cells towards the free surface or the walls (e.g., into the light zone, or photic zone) and away from the light again. Such a device may solve problems in that it may prevent the algae near the wall from staying there and getting light-saturated, and perhaps it may even bring the algae in the interior of the PBR to the light so they can get enough light to grow.

One goal for some embodiments of the present invention may be a creation of spectrum of motions for a mixing regime which can efficiently move microorganisms into and out of the photic zones. The spectrum of such motions may be referred to as Growth Enhancing Mixing Spectrum ("GEMS").

It is another goal in some embodiments of the present invention to provide energy in large scales to mix fed organic carbon and nutrients if better heterotrophic/mixotrophic growth is to be realized. Yet another goal may include the ability generate and even maintain a constant degree of mixing over the time needed for the microorganisms to grow to maturity.

It is a goal in some embodiments of the present invention to provide a system that can be scaled efficiently, perhaps with very little flow shear, and even at remarkably slow flow speeds so as to reduce energy requirements.

Yet another goal in embodiments of the present invention is to provide a bioreactor system or even a photobioreactor system that can continuously grow microalgae and other microbes in a protected environment, perhaps on a large scale, and even using optimum growth practices, while using a minimum amount of energy to do so.

One goal of some embodiments of the present invention may include to at least equal the maximum laboratory PBR growth rates perhaps with a scalable, continuously running, cost effective PBR that can be used in industrial situations.

Another goal in some embodiments of the present invention may provide that a bioreactor be easily and even inexpensively temperature controlled. Furthermore, a bioreactor may require minimum maintenance and may even be adjustable for pH, nutrient, $CO_2$ variations, $O_2$ removal, or the like perhaps as the algae grows.

It is a goal of certain embodiments of the present invention to provide a strong cross-flow perhaps in a pipe-type bioreactor and perhaps even without the use of mechanical forcing due to blades, propellers, rotors, bubbles, jets, or any device that requires direct mechanical energy input, or the like.

Another goal of various embodiments of the present invention may include shortening the time microorganisms spend in a dark zone perhaps with directed cross-flows that may move the microorganisms into and out of a photic zone perhaps with the frequency needed to maximize growth.

Naturally, further objects, goals and embodiments of the inventions are disclosed throughout other areas of the specification, claims, and drawings.

BRIEF DESCRIPTION OF THE DRAWINGS

FIG. 62 shows an example layout for a bioreactor system in accordance with some embodiments of the present invention.

DETAILED DESCRIPTION OF THE PREFERRED EMBODIMENTS

Figure 1:
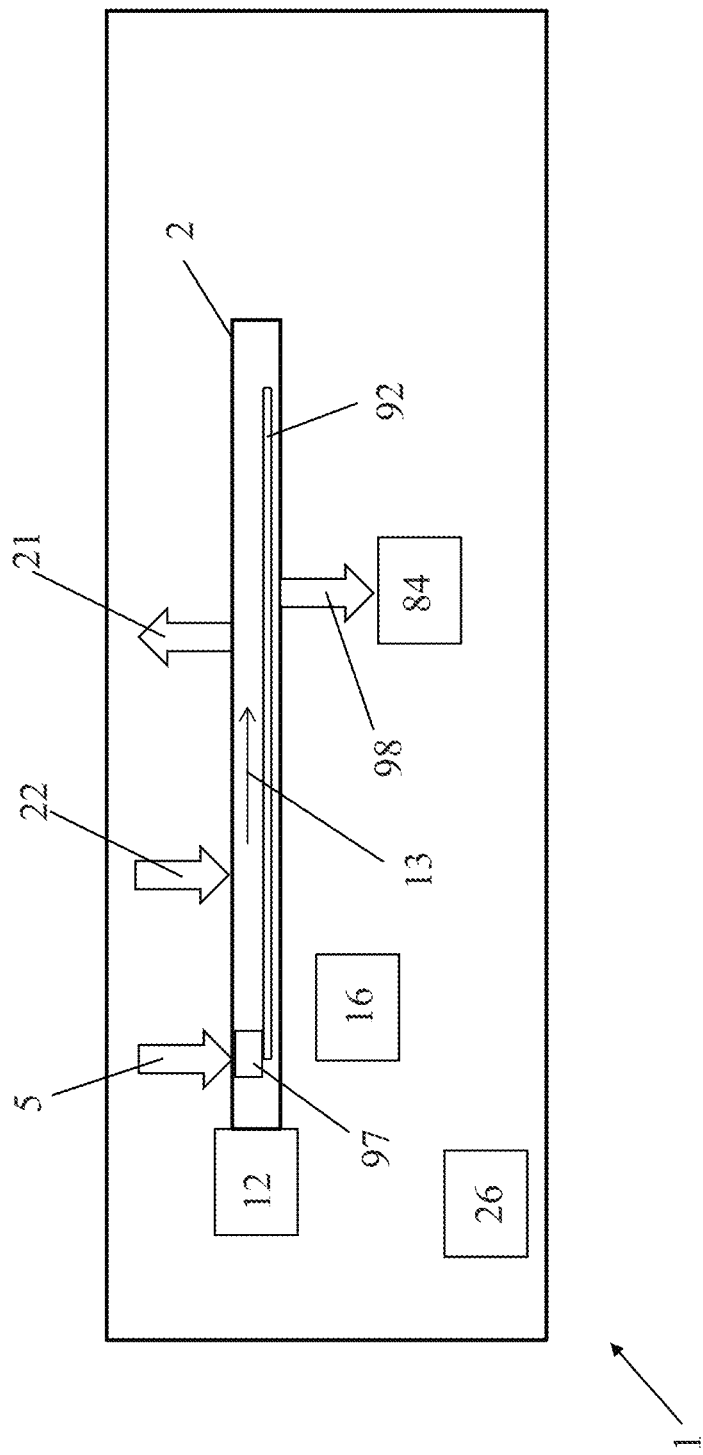
FIG. 1 is a schematic diagram of a bioreactor system according to some embodiments of the present invention.

The present invention includes a variety of aspects, which may be combined in different ways. The following descriptions are provided to list elements and describe some of the embodiments of the present invention. These elements are listed with initial embodiments; however, it should be understood that they may be combined in any manner and in any number to create additional embodiments. The variously described examples and preferred embodiments should not be construed to limit the present invention to only the explicitly described systems, techniques, and applications. The specific embodiment or embodiments shown are examples only. The specification should be understood and is intended as supporting broad claims as well as each embodiment, and even claims where other embodiments may be excluded. Importantly, disclosure of merely exemplary embodiments is not meant to limit the breadth of other more encompassing claims that may be made where such may be only one of several methods or embodiments which could be employed in a broader claim or the like. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

In view of the aforementioned disadvantages of existing bioreactors and photobioreactors, embodiments of the present invention may provide enhanced productivity of microorganisms (e.g., algae, cyanobacteria, or the like) for bioreactor systems, such as closed photobioreactor systems, perhaps on scales not economically achievable today. However, the modifications required to create the systems described herein can be applied to either small scale or even large bioreactors and photobioreactors with significant benefits of microorganism growth and even low energy usage.

Embodiments of the present invention may be provide continuously flowing, closed bioreactors that can be modified to grow phototrophic, heterotrophic, mixotrophic, or the like microorganisms, which may include continuously present static mixing devices that can introduce significant energy perhaps into cross-stream mixing motions on cross-stream scales of the diameter of the apparatus, as well as perhaps imparting energy to motions across the entire turbulent energy spectrum. Bioreactor systems in the various embodiments of the present invention can be used to grow a very large number of microorganisms, perhaps since the mixing motions can be imparted with a large degree of control, even with low shear stress, that may result in very little energy loss.

Embodiments of the present invention provide fluid flow coordinators (92) or even passive microorganisms flow modifiers (93) that can create a new energy spectrum, which may be a superior fluid mixing energy spectrum, that we have called the Growth Enhancing Mixing Spectrum ("GEMS"). The ability to create GEMS in a bioreactor allows scalability to sizes significantly beyond the size of traditional bioreactors, perhaps while utilizing very little additional mechanical energy to stir the fluid perhaps for mixing purposes.

GEMS may be an energy spectrum that may contain much more energy in the large scales (~D) of the flow. These scales may persist for a long time. When a fluid flow and the items contained therein come near an inwardly protruding helical spine, it may result in flow separation that is perhaps unsteady in time and space, and even elliptical in character, and may even depend on the geometry around it. An inwardly protruding helical spine may bringing flow (with the microorganisms in it) to a light source at the walls of the pipe-type reactor.

Once an inwardly protruding helical spine or any device that may create the desired flow separations may be designed, created in, or even installed in, a pipe-type bioreactor, it need not move or change shape. It may be considered a static flow modifier or even a passive mixing device. Because of the nature of the separations induced by a passive mixing device, bioreactors can be designed and even used for processing microorganisms from lab scales to industrial/commercial scales. Because there may not be any mechanical motion of the device to create the GEMS, there may not be any motors or electricity required. The establishment of the cross-flows may take energy out of a main flow, but because the overall flow in a GEMS bioreactor can be run at slower bulk speeds than are currently used in pipe-type bioreactors or photobioreactors, the energy requirements to produce algae, for example, may actually go down. A required passive mixing device may scale with the diameter of the main bounding surface of the bioreactor (e.g., the diameter of a pipe) or perhaps even with a gap size in co-axial implementations, and the GEMS mixing that it may introduce may scale proportionally to a mixing mechanism.

Examples in this discussion include discussion on the growth of microalgae. This is not meant to limit the scope of the disclosure in any way. Any discussion of algae or microalgae or the like may be applied to any type of microorganism. Embodiments of the present invention may modify the spectrum of cross-flow motions that can be made perhaps to optimize the growth of a wide range of microorganisms, alga, genetic modifications of an alga, or the like. In addition, some embodiments of the present invention include circular tubing components such as circular pipes. However, it is understood that this is a non-limiting example only and the invention is not limited to round pipes as channels of any cross-section can benefit.

Embodiments of the present invention try to avoid bioreactor systems that can produce high shear rates which can result in cell breakage. The optimum level of turbulence for mixing, which may create shear stress for cells, may be a result of fluid flow and even gas velocity. If the optimum intensity of turbulence, over the full range of scales of the spectrum, can be created via other means (perhaps than blade impellers or excessive airflows), then cell breakage can be reduced. As the cell density may increase, the effective viscosity of the fluid mixture may rise, which may work against uniform mixing and even subsequent optimum mass transfer of nutrients. Algae, which may be similar to other species of plants in suspension culture, vary in their resistance to shear. This has been a major challenge in developing a standard photobioreactor in which all cells can be grown. It is desirable to produce the cross-flow motions as gently as possible, via separated flow from a surface so moving devices may not be needed to impart thrust to the fluid.

Figure 4:
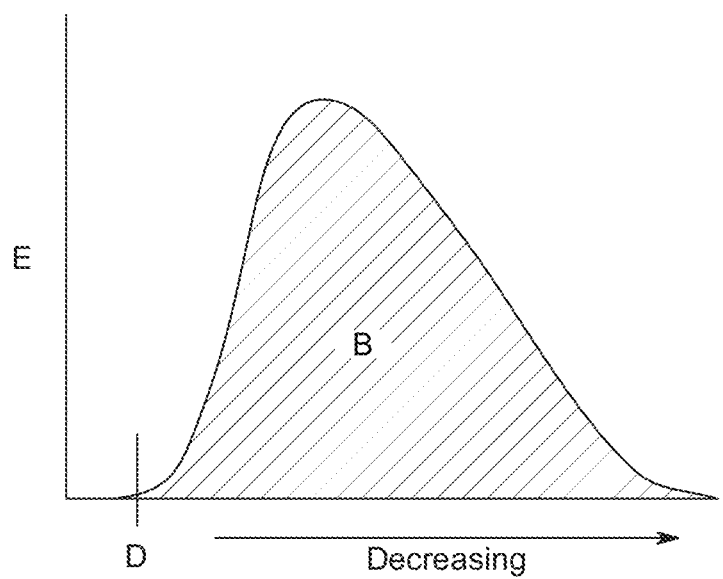
FIG. 4 is an example of a naturally occurring 3-D turbulence energy spectrum in accordance with some embodiments of the present invention.

Fully developed turbulent flow in the pipes of past bioreactor systems may create very little energy in scales of the diameter of the pipe. FIG. 4 shows an example of a naturally occurring 3-D turbulence energy spectrum, wherein the x-axis represents the wavenumber of the scales of motion that may be generated. Wavenumber is proportional to 1/wavelength and wavelength is a representation of the size of the eddies. The wavenumber may go from zero to infinity, wherein smaller wavenumbers may represent larger scales of motion. The energy in each of these scales is represented the y-axis. As may be understood from FIG. 4, there is very little energy in large scale motions, the demarcation labeled "D" represents the energy in eddies the size of the diameter of the pipe.

There may be very slow, or essentially no, transport of mass from a center of a pipe to the walls of the pipe and from the walls back to the center over many diameters of pipe length. In a pipe-type bioreactor, microorganisms could be transported very slowly from the center of a pipe to its walls and vice versa perhaps by the naturally occurring turbulence. Since the energy in the turbulence may be proportional to the mean flow speed in a pipe, even at high speeds (which could also produce high shear stress that may damage the microorganisms, and may use more energy), the time scales for transport across a pipe, $D/u'$ (where $u'$ is the intensity of the turbulence, and U is the mean flow speed) are such that the microorganisms could not get to the walls any more frequently per unit length of pipe.

This may be because, as is well-known to those familiar with the art of turbulent flows, even the large scales of the turbulent energy spectrum may be quasi-self-similar. The energy spectrum may not change shape as the speed of the flow may change. It may increase in size, (e.g., the area under the spectral shape may increase). Thus, even though there may be more energy in large-scale motions as the mean pipe flow speed may increase (this may be true, in proportion for all the scales), there may not be different types of eddies and there may not be any new energy for new large eddies. This is what may be needed to create a transport of the algae across a pipe diameter.

Embodiments of the present invention may focus on the transfer of microorganisms such as algae cells (e.g., the transfer of their cell mass or mass transfer) from an interior of the ducts to the light that may enter a photobioreactor at the walls of the ducts, and may even penetrate in as described above creating a photic zone. A photic zone may effectively be deepened by getting as much as possible of the light at the walls to the algae cells in the interior of the pipe perhaps by moving the algae that has grown and darkened in color, away from the walls, and replacing them with other algae cells that may be deeper in the center of the pipe bioreactor, perhaps that have not yet grown enough because they have not received as much light to deepened their color. It may be desirable to create scales that may be large enough to convect the algae from the center of the pipe towards the walls. Since the center region of a pipe flow may be essentially inviscid, these scales by definition should be inviscid (e.g., not governed by viscosity). To those skilled in the art of fluid mechanics, this may mean that the scales of motion are Reynolds number independent, and that they can carry the algal cells across the largely inviscid outer region of the pipe flow all the way to the pipe walls. A Reynolds number independence furthermore may enable us to change an overall speed of the flow and may not change the resulting cross-flow dynamics. Embodiments of the present invention may act to create large scale cross flows. Because these large-scale motions may not be affected by viscosity, they may also not be affected as the density of the algal suspension increases, and as happens, along with the cell growth, the viscosity of the mixture may increase. Thus, they are of a scale that may reflect the need to transport the algae across a pipe. These motions may not be affected as efforts to slow down the flow may be made, perhaps in the interest of decreasing the energy needed to drive the main flow, because as we discuss herein, they may be generated by separation processes, that also may be Reynolds number independent.

To produce such flows, in general, may mean that systems and methods may need to be much larger with respect the duct diameter than heat transfer devices. They may also be of a much larger axial scale (e.g., pitch) than heat transfer augmentation devices. There may be no requirement for devices to interact with viscous sublayer scales, and there may be a desire to have them operate perhaps essentially the same, as the fluid viscosity itself may change with increasing algae density. There may be however, an inviscid/viscous interaction that may take place as cross-flows generated may interact with portions of the wall that they may be directed towards. New devices may have very little shear stress as opposed to heat transfer augmentation devices which may be designed to have high shear stress. Embodiments of the present invention may be considered a mass transfer system.

Furthermore, although mixing over a large range of scales in a bioreactor may be essential to enable high and even consistent growth rate of all microorganisms, unlike mixing to enhance heat transfer, the shear stresses that may be imparted to the fluid, and thus may be imparted to the microorganisms in that fluid, may result from such mixing and should be kept as low as possible so as not to damage the microorganisms. Hence, when considering new devices and philosophies that can lead to mass transfer of microorganisms, and to the gases (e.g., $CO_2$ and $O_2$), and to the nutrients in a bioreactor, the range of heat transfer augmentation devices do little to meet these requirements. Objectives of mixing constituents in a pipe flow bioreactor may also be different from heat transfer to or even from a pipe. In a bioreactor, all scales of mixing down to those of the microorganisms may be important. This mixing on the smallest scales may enable microorganisms to exchange gases and even feed on nutrients. On the scale of the pipe, mixing of CO and nutrients in the water, when continually reintroducing them into the center of the pipe, may be important for their utilization by the microorganisms.

Getting all the necessary scales of mixing, while not creating high shear stress may be an important concept. Some embodiments of the present invention provide scaled, passive, helical impressions of specified wavelength into circular ducts (or any other duct shapes) that may create needed inviscid large scales for mixing and all the requisite scales perhaps with very low shear.

Embodiments of the present invention may provide methods and systems that can continuously apply a forcing function onto an algae suspension that may: 1) result in an unsteady spectrum of motions which can produce cross-flows that extend across the reactor dimensions; 2) keep a constant fluctuating energy spectrum intensity perhaps at all scales of the motion imparted; 3) keep this constant fluctuation energy spectrum perhaps all along a length of a reactor, perhaps throughout the growth of the algae or, if needed, which can algorithmically adjust the energy in the large scale motions at prescribed stages of algal development; and perhaps even 4) differ from a classical turbulence energy spectrum in that it may have significantly more energy in scales of the primary scale of the bioreactor (e.g., a distance between its walls). The alga may need to be moved on these scales if they are to be moved into the source of photons of light coming into the walls of the bioreactor and perhaps then away from the walls, even out of the high intensity light energy, without being damaged perhaps by receiving too much light. It may be desirable to have algae experience a constant light/dark duty cycle (e.g., photo adaptability). In a laboratory this may be possible to do, for example, on small liter-scale bioreactors perhaps by using magnetic agitators or even rotating propellers. But, to do this on much larger, commercial scales, using classical bioreactors as outlined above, could be impossible without using unacceptably large amounts of energy, putting unacceptably high shear stresses on the algae (which may cause their cells to be damaged), and perhaps even taking large amounts of land. Furthermore, a light/dark cycling in these past devices could have long dark times and even be very aperiodic, rather than stochastically steady as may occur in embodiments of the present invention.

Figure 5:
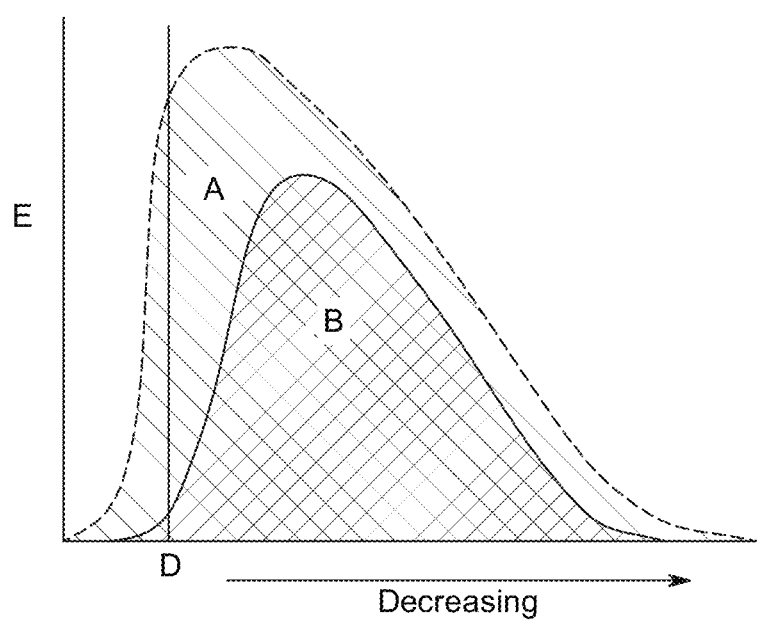
FIG. 5 is an example of a new turbulence energy spectrum (A+B) over the old (classical) spectrum (B) in accordance with some embodiments of the present invention.

Embodiments of the present invention may provide passive devices that can result in mixing of an entire flow. It may be that we are augmenting the classical three-dimensional turbulent energy spectrum as represented in FIG. 4, by adding fluctuating energy into scales of motion that may be most responsible for bringing algae cells into and out of the locations of high light intensity, e.g., cross-flow motion of the scale of the bioreactors. FIG. 5 shows an example of a new spectrum (A+B) and the old classical spectrum (B). This energy spectrum may be a plot of the energy in the various eddies in the flow field versus the sizes of the eddies (size may be defined by their turn over length scales). The size of the eddies may get smaller as we move to the right of the x-axis (e.g., smaller scale eddies are to the right on the x-axis). The new enhanced spectrum may have a constant shape and magnitude as the algae (or other microorganisms) flows down the spiral intrusion modified pipe and grows; the additional energy may be the energy in the area "A". The new enhanced energy spectrum may be stochastically steady perhaps because a fluid flow coordinator or even a passive microorganism flow modifier may be present all along an axis of a pipe-type bioreactor. In the turbulence energy spectrum that could exist in a pipe without the enhancements, the energy could exist only under the curve "B", as noted above. In a normal turbulence pipe flow, the flow may basically flow along the axis of the pipe perhaps with occasional excursions (rarely of a scale compared to the pipe diameter scale) towards and even away from the walls.

Figure 6:
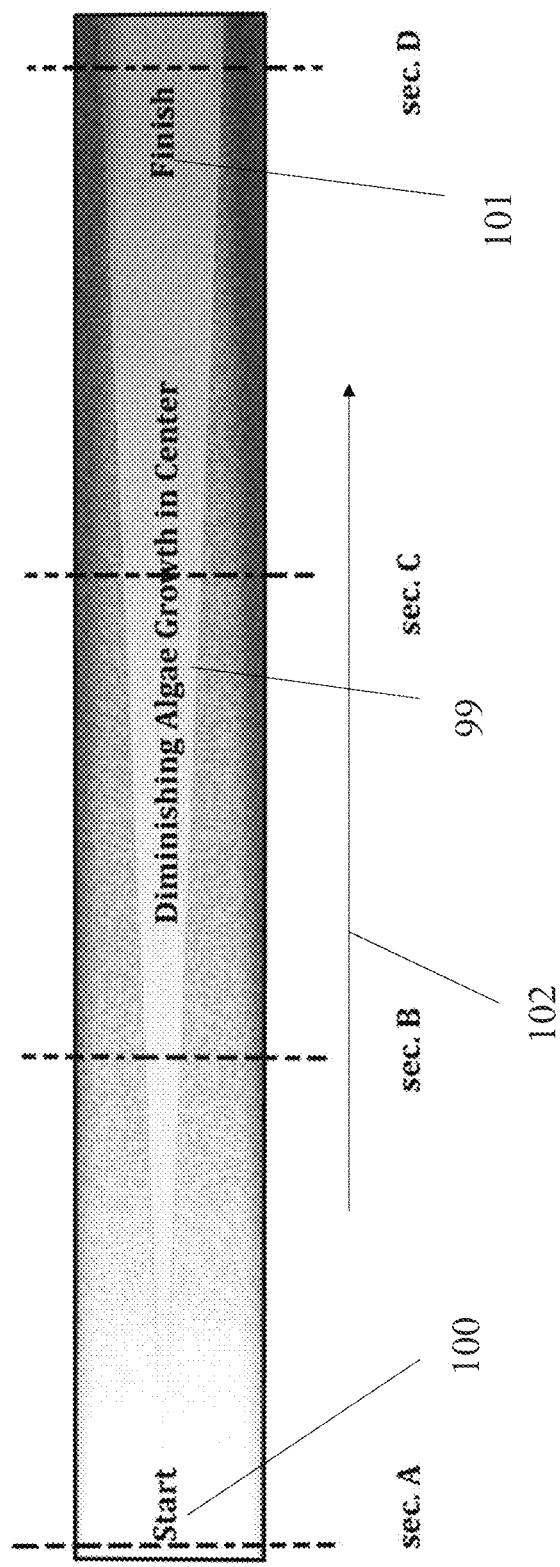
FIG. 6 shows an algae density during growth due to effective light penetration in accordance with some embodiments of the present invention.

FIG. 6 shows the average or mean flow results of algae growth under naturally occurring turbulence conditions in a tubular photobioreactor that is uniformly illuminated around its walls. Algae that may be near the walls of a pipe may stay there for too long a time, receiving light, growing fast, and darkening. The result may be a shading of the algal cells deeper in the pipe, and thus slower growth of all alga that may be away from the walls and also the light. This is represented by the lighter shading in the center of the pipe. Conceptually, if the pipe may be long enough (e.g., equivalent to the algae being given more time to grow), eventually all the algae could grow and even darken because there will be some energy in the large scales, that may carry the algae, however unevenly, from centerline to a wall. Of course, this uneven growth could result in inefficient production, and the longer the resident times may occur for algae near the high intensity light, which could result in photobleaching of some of the algae, their death, and perhaps even the underdevelopment of other cells.

Figure 10:
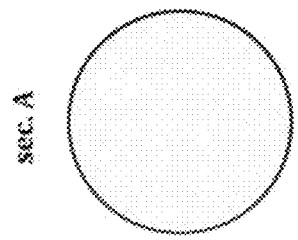
FIG. 10 shows a cross-section at sec. D of FIG. 6 in accordance with some embodiments of the present invention.
Figure 9:
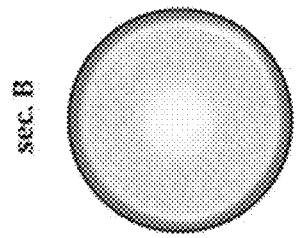
FIG. 9 shows a cross-section at sec. C of FIG. 6 in accordance with some embodiments of the present invention.
Figure 8:
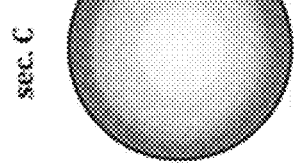
FIG. 8 shows a cross-section at sec. B of FIG. 6 in accordance with some embodiments of the present invention.
Figure 7:
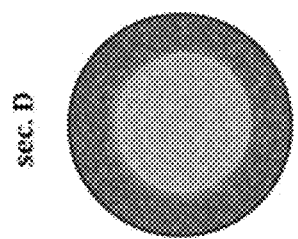
FIG. 7 shows a cross-section at sec. A of FIG. 6 in accordance with some embodiments of the present invention.

FIG. 6 shows a non-limiting example of the mean algae density in a pipe of a photobioreactor during growth due to effective light penetration. A fluid flow direction (102) may be from the right to the left. As algae grows and its density increases on the pipe wall, it may slow down and/or stop the algae growth in the center of the pipe. At the beginning (100), light may be able to penetrate from the walls to the center of the pipe as shown on the cross-section A represented in FIG. 7 (sec. A). This may be at about ~100% light penetration. As the algae grows, the light penetration may decrease and the algae growth in the center of the pipe may diminish (99), see cross-section B and cross-section C represented in FIG. 8 (sec. B) and FIG. 9 (sec. C). FIG. 8 may be at about 70% light penetration and FIG. 9 may be at about 30% light penetration. Finally, once the algae may be grown at the end of the pipe, section (101), there may be very little if any, algae growth away from the sides of the pipe, see cross-section D represented in FIG. 10 (sec D).

In naturally occurring turbulence, there may be larger scale motions, some which may be the scale of the diameter of the pipe, but they may have very little of the turbulent flow's energy, and thus may result on very slow cross-flow motions. These may not be of much use to the algal growth, perhaps because they move the algae towards and away from the light at the walls too slowly to result in optimum algae growth. Naturally occurring turbulence, when assisting mixing purposes in biological systems, may mainly assist in scales that can enable better contact of microbes with nutrients and with $CO_2/O_2$, for example. Pipe turbulence may be poor in bringing algal cells into the light at the walls or moving these cells away from the walls (see the low energy in FIG. 4 at the location of the pipe diameter indicated by the line and letter "D"). The new enhanced spectrum of FIG. 5, which we may refer to as the Growth Enhancing Mixing Spectrum ("GEMS"), may be important for algae growth perhaps because it may move the cells on scales that can bring the alga into contact with, and then take them away from, the high intensity light coming into the bioreactor at the walls. Since there may be little energy in motions on the order of the pipe diameter in ordinary turbulence to carry algae towards and away from the walls where light may be introduced, this may lead to the classical algae growth problem: algae that are near the walls of a photobioreactor, grow fast, become green, largely remain near the walls, and can even prevent light from getting to the rest of the algae in the pipe (e.g., they shade these algae from the incident light) which therefore do not grow, or grow very slowly as can be understood in FIGS. 6-10.

Figure 70:
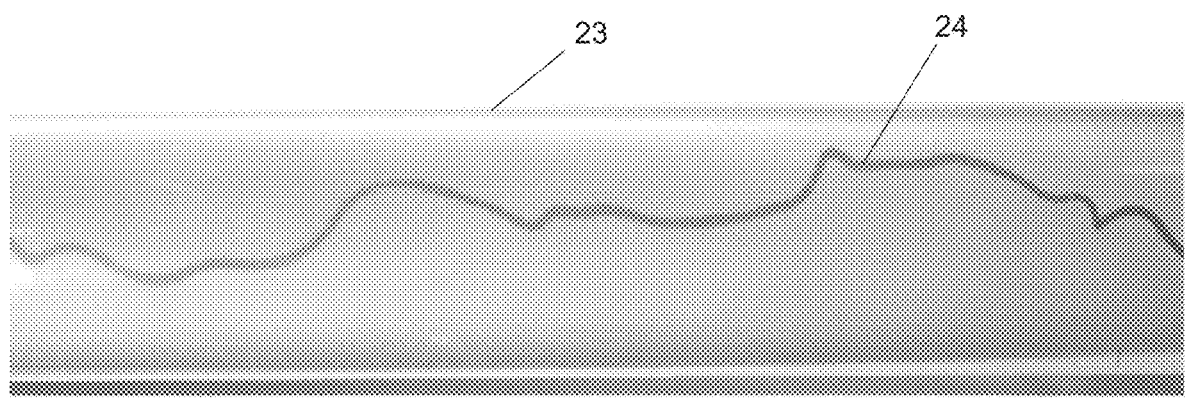
FIG. 70 shows an example of a photograph of a movement of dye in a tubing component in accordance with some embodiments of the present invention.

FIG. 70 shows a photograph of an example movement of a dye (mixed with a dilute polymer solution to enable us to follow the dyed particle paths easier) that has been injected into the centerline of a standard smooth walled tubing component (23). The polymer dye paths are shown at a random time centered at 10 pipe diameters downstream of the injector in a 6" diameter pipe. These figures may represent a range of lateral or even cross-stream mixing that 'natural turbulence' (the churning phenomenon) may produce. The Reynolds number of this flow (the indicator of whether the flow is turbulent or not), is about 10,000, and it may be known that turbulence may set in at a Reynolds number of about 2000. Thus, this flow should be considered fully turbulent. When a flow is turbulent in standard piping, it may only produce little bumps (24) in the dye line and may not move the dye across the pipe to the walls. The turbulence may not be not strong enough to break the dye filament as it may only cause it to wave and kink a bit. Note that dye in the filament is made viscoelastic by mixing a dilute polymer solution into it so that it may stay together so as to be able to view the history of its motion (otherwise it could diffuse quickly and disperse into the water due to the small-scale motions of the turbulence. The dye in FIG. 70 shows that the dye undergoes wiggling due to the motions of the large-scale eddies in natural turbulence. Over the field of view (more than 5 pipe diameters) none of the dyed particles may have come to the walls of the pipe, which illustrates that naturally occurring turbulence does not have a lot of energy in eddies of the diameter of the pipe, and thus, is ineffective in bringing the algae to the light coming into the photobioreactor at the walls of the pipe.

Embodiments of the present invention may provide a GEMS system. These systems may produce the energy under area "A" of the spectrum of FIG. 5 and may also produce a full spectrum of classical turbulent motions that may be needed for mixing of the $CO_2$ and nutrients, or the like, and it may do this at much lower flow speeds (e.g., or Reynolds Numbers) perhaps even than required to sustain classical turbulence in a pipe. Thus, for a given system, this may be at a much lower flow speed. Embodiments of the present invention may also create more energy over all of the classical turbulence wavelengths (see FIG. 5). Thus, systems of the present invention may enable a full range of motions needed for growth perhaps at a much lower level of shear stress, so that the algae or other microorganisms may not be damaged by the flow itself. Time scales for cross-flow motions in embodiments of the present invention may not be governed by the overall turbulence intensity, but may be governed by a bursting intensity of the separation regions that may develop on a fluid flow coordinator or even a passive microorganism flow modifier. These time scales can be described as D/U' vs. D/u'. Since U' may be much larger than u', the time to move algae across a bioreactor may be much less than the naturally occurring turbulence would take. Furthermore, because a much lower mean axial pipe flow speed may be used (since U' may essentially be independent of u' in the GEMS), while achieving the needed mixing motions, the energy needed to drive the flow may be minimal (e.g., energy needed square of the speed).

Figure 71:
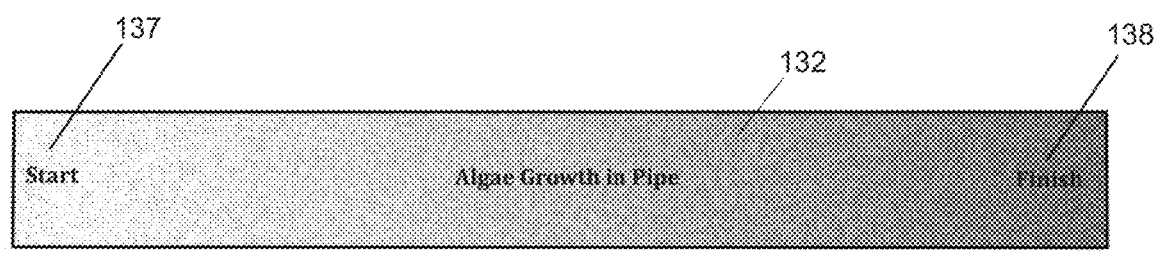
FIG. 71 shows an example of algae growth in a tube in accordance with some embodiments of the present invention.
Figure 72:
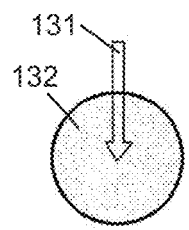
FIG. 72 shows an example of a cross-sectional density of algae and the penetration of light therein at a section of a tubing in FIG. 71 in accordance with some embodiments of the present invention.
Figure 73:
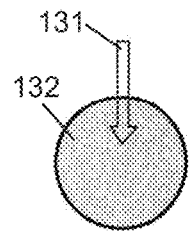
FIG. 73 shows an example of a cross-sectional density of algae and the penetration of light therein at a section of a tubing in FIG. 71 in accordance with some embodiments of the present invention.
Figure 74:
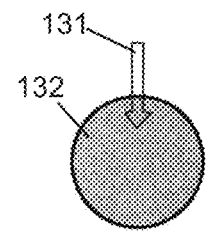
FIG. 74 shows an example of a cross-sectional density of algae and the penetration of light therein at a section of a tubing in FIG. 71 in accordance with some embodiments of the present invention.
Figure 75:
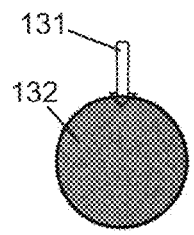
FIG. 75 shows an example of a cross-sectional density of algae and the penetration of light therein at a section of a tubing in FIG. 71 in accordance with some embodiments of the present invention.

Embodiments of the present invention can maintain this spectrum throughout the growth of the algal system, perhaps as it may exist within the bioreactor all along the length of the pipe. It may be desirable to produce algae growth that may be as uniform as possible across the pipe, at each station along the length of the pipe, as indicated by the shading in FIG. 71. Ideally the GEMS spectrum may be able to do this. FIG. 71 provides an example of algae growth in a tube, perhaps at a start (137) of a tube, light may be able to penetrate from the walls to a center of the tube. Microorganism growth density (132) is represented by shading in FIG. 71. FIGS. 72 to 75 provide examples of the cross-sectional densities at certain stations of FIG. 71 nominally showing the decreasing penetration of a light zone (131) that may occur as the density of microorganisms (132) increases in a tubing component, and emphasizing the uniformity of algae growth across the tube. FIG. 72 may show about 100% of light penetration, FIG. 73 may show about 70% of light penetration, FIG. 74 may show about 30% of light penetration, and FIG. 75 may show about 10% of light penetration. As the light penetration decreases with increasing algae density, the continued algae growth increasingly depends upon bring the algae to the light at the walls of the tube. If necessary, the energy in the spectrum can be amplified at different stations along the tube, perhaps by adjusting a passive mixing device such as, but not limited to, in amplitude, pitch and even profile shape.

Figure 76:
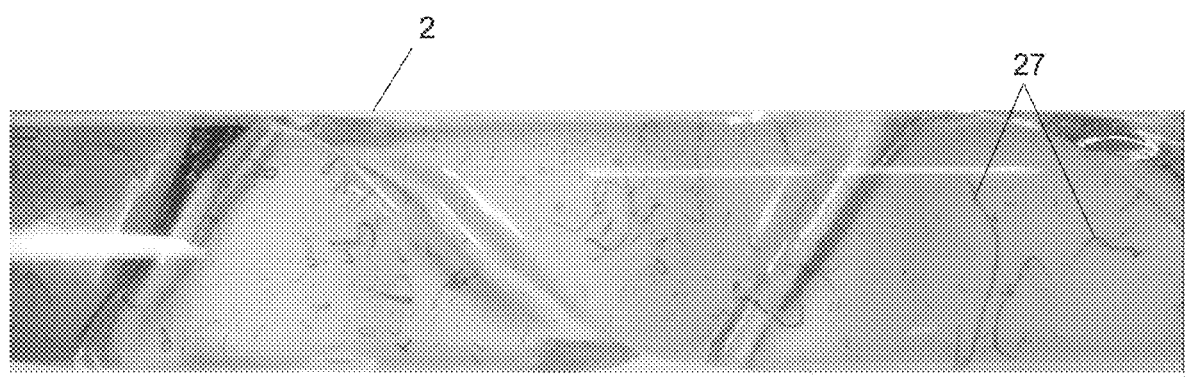
FIG. 76 shows an example of a dispersion of microorganisms in a tubing component in accordance with some embodiments of the present invention.

An example of the particle paths (illustrated by dyed particles) that can result in such uniform growth is shown in FIGS. 28-31, and using a dye in even more dilute polymer solution, in FIG. 76.

Embodiments of the present invention may provide a GEMS (the Growth Enhancing Mixing Spectrum), and the means by which GEMS may be generated may include employing passive, low shear stress, low energy usage, flow field altering devices, that produce cross-flows of the order of magnitude of the scale of the duct type bioreactor, or the like. In general, devices may create flow separation from their surface which may scale on the cross-flow dimension of the apparatus.

Embodiments of the present invention may provide a bioreactor system comprising a tubing component; a fluid input configured to add a fluid into said tubing component; an inoculate input configured to add microorganisms into said tubing component; multiple nutrient and gas inputs configured to add nutrients and gases into said tubing component; a fluid flow impetus capable of creating a fluid flow of said fluid, said microorganisms, and said nutrients and gases through said tubing component; a fluid flow coordinator capable of inducing unsteady multiscale cross flows within said fluid and promoting said microorganisms to disperse within said fluid in said tubing component; and perhaps even a microorganism collector or algae collector attached to said tubing component.

Other embodiments of the present invention may provide a method for a biologically active environment comprising the steps of flowing a fluid through a tubing component; adding microorganisms to said fluid in said tubing component; adding nutrients to said fluid in said tubing component; continuously inducing unsteady multiscale cross-flows within said fluid in said tubing component; promoting dispersion and mixing of said microorganisms within said fluid in said tubing component; and perhaps even harvesting grown microorganisms from said fluid.

Embodiments of the present invention may provide a bioreactor system comprising a tubing component; a fluid input configured to add a fluid into said tubing component; an inoculate input configured to add microorganisms into said tubing component; a nutrient input configured to add nutrients into said tubing component; a fluid flow impetus capable of creating a fluid flow of said fluid, said microorganisms, and said nutrients through said tubing component; a passive flow modifier capable of passively generating cross-flows in said fluid containing microorganisms, convecting them substantially throughout said tubing component and promoting dispersion of said microorganisms substantially within said fluid in said tubing component; and perhaps even a microorganism collector attached to said tubing component.

In yet other embodiments of the present invention, they may provide a method for a biologically active environment comprising the steps of flowing a fluid throughout a tubing component; adding microorganisms to said fluid in said tubing component; adding nutrients to said fluid in said tubing component; passively generating cross flows in said fluid substantially throughout said tubing component; promoting dispersion of said microorganisms substantially within said fluid in said tubing component; and harvesting grown microorganisms from said fluid.

FIG. 1 provides a schematic example of bioreactor systems in accordance with some embodiments of the present invention. Embodiments of the present invention may provide a bioreactor system (1) with a tubing component (2), an input (5) which may provide input of a fluid, a fluid flow impetus (12) which may create a fluid flow (13) in the tubing component, a fluid flow coordinator (92), a gas input (22), a gas release (21), inputted components (97), an output (98), outputted components (84), a program (26), and perhaps even a system constituent (16), or any combination or permutation thereof. Fluids may flow through a tubing component, either single pass or recirculated, where microorganisms may be added, nutrients may be added, or the like. Outputted components (84) may include microorganisms exiting a system perhaps into a microorganism collector where microorganisms may be harvested or even continuously harvested. In some embodiments, a microorganism collector may be attached to a tubing component.

Figure 2:
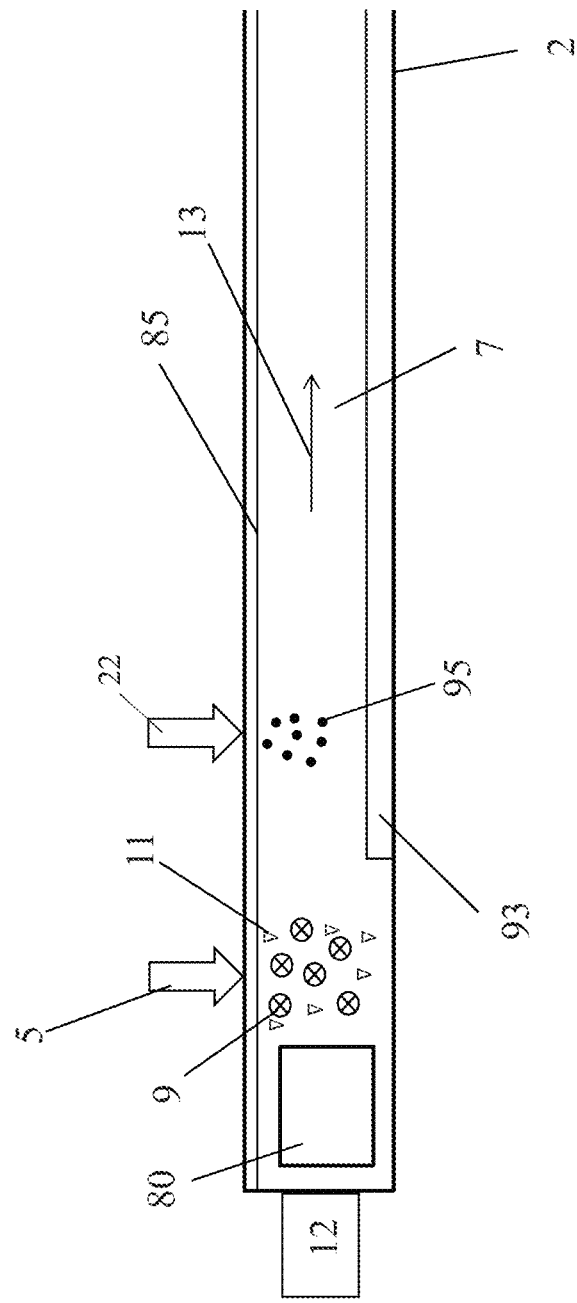
FIG. 2 is a schematic diagram of bioreactor system according to some embodiments of the present invention.

FIG. 2 provides an example of bioreactor system which may include, but is not limited to, a tubing component (2) which may be substantially filled (85) with a fluid (7), an input (5) which may input microorganisms (9) or nutrients (11) or the like, a gas input (22) which may input gas (95). Fluid in the tubing component may be flowing in a fluid flow (13) perhaps driven by a fluid flow impetus (12). The microorganisms and other inputted items may be continuously mixed perhaps with a continuous mixing element (80). A flow of the fluid may be modified perhaps with a passive microorganism flow modifier (93).

Embodiments of the present invention may provide substantially filling a tubing component with a fluid and wherein a continuous mixing element or the like may be configured to optimally continuously mix when a tubing component may be substantially full. A fluid input may be applied to a substantially filled tubing component with a fluid which may result in optimum, more complete, preferred, mixing of the constituents of said fluid, and may result in more exposure of the constituents of a fluid to light coming into the bioreactor from its walls. A substantially filled tubing component with a fluid may enable a fluid to receive a maximum force from a fluid flow coordinator, passive microorganisms flow modifier, or even inwardly protruding helical spines perhaps so as to create a most intense fluid mixing motion. A substantially filled tubing component may be almost entirely filled. For example, using percentage values as one example, for a tubing component to be substantially filled, it should be understood that embodiments of the invention may encompass the option of percentage values that include 99.5%, 99%, 97%, 95%, 92% or even 90% of a maximum amount of fluid that may completely fill a tubing component.

Figure 3:
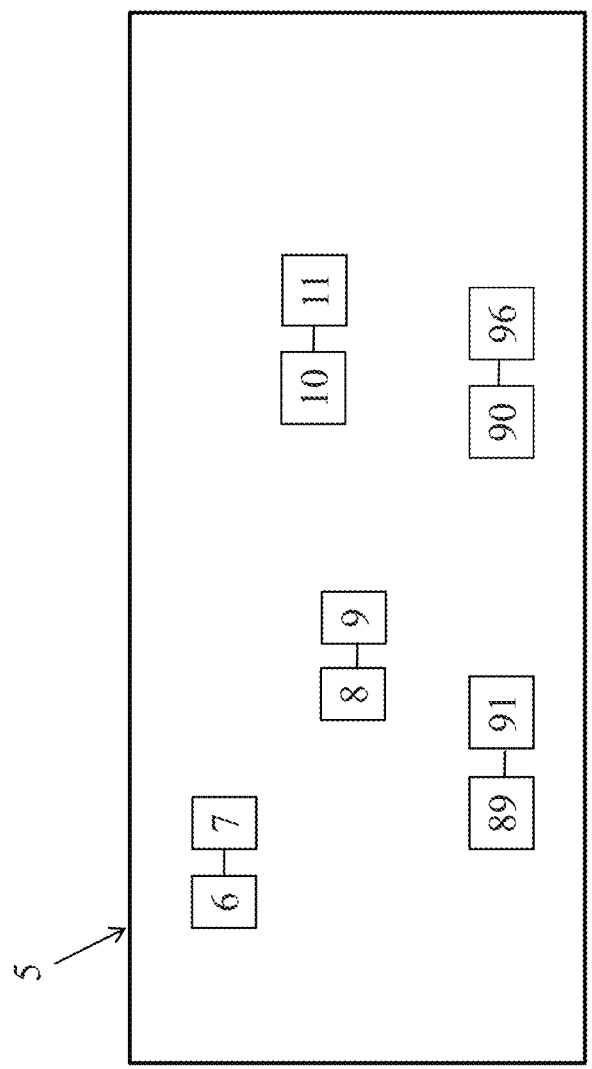
FIG. 3 is a schematic diagram of bioreactor system according to some embodiments of the present invention.

FIG. 3 provides a schematic representation of examples of inputs that may be used in various embodiments of the present invention. An input may be any kind of device that may allow something to be added to a tubing component such as but not limited to a valve, nozzle, inlet, spout, or the like. There may be at least one input, two inputs, or a plurality of inputs in a device. For example, an input (5) may be a fluid input (6) which can be configured to add fluid (7) into a tubing component. An input (5) may be an inoculate input (8) which may be configured to add microorganisms (9), biomass, mineral mass, or the like into a tubing component. An input (5) may be a waste input (89) or even an industrial waste input which may add waste (91) such as industrial waste, commercial waste, carbon dioxide from electrical generating plants, carbon dioxide from concrete plants, carbon dioxide from steel plants, carbon dioxide from ethanol plants, carbon dioxide from breweries, carbon dioxide emitted in flue gas, wastewater from municipalities, or the like into a tubing component. An input (5) may be a nutrient input (10) which may be configured to add nutrients (11) into a tubing component. An input (5) may be a growth stimulator input (90) which may add growth stimulator (96) into a tubing component. As shown in FIG. 1, an input may add inputted components (97) to a tubing component such as but not limited to microorganisms, fluid, waste, nutrients, growth stimulators, biomass, mineral mass, or the like. An input may be configured to continuously or even quasi-continuously add, at selected stations along the tubing-type bioreactor, inputted components such as nutrients or the like to a tubing component.

A bioreactor system (1) may include any manufactured or even engineered device or system that may support a biologically active environment. A bioreactor system may include, but is not limited to a photobioreactor system, a fermentation bioreactor system, an open bioreactor system, a closed bioreactor system, a large-scale bioreactor system, a single-pass photobioreactor system, a single-pass gravity driven bioreactor system, fermentation bioreactor system, a recirculating bioreactor system, or the like. The pipe flow modification system can also be configured to serve as a slurry conveyance pipeline, open channel flow system, high temperature systems, high pressure systems, or both, or the like. In some embodiments, a bioreactor system may be a photobioreactor utilizing microalgae. In other embodiments a bioreactor system may optimize cultivation of microorganisms, and the tubing component with passive flow modifiers described may optimize a thermochemical conversion of biomass, or may even provide conveyance of slurries of biomass or minerals or even foodstuffs or the like. A tubing component with passive flow modifiers described may be used in high temperature and high-pressure systems perhaps for high temperature carbonization of biomass; a high temperature and high-pressure system perhaps for high temperature liquefaction of biomass to make biocrude; a high temperature liquefaction of biomass into crude oil; a high-temperature and high-pressure system, or the like in various embodiments of the present invention. Thermochemical changes may be used in various systems perhaps to make crude oil, sterilize, or the like. A tubing component system with the passive flow modifier may be used to transport slurry of any kind, water slurries, oil, gas, mineral solids such as but not limited to pulverized coal, ores, iron ore, phosphates, limestone, silt, or the like.

A bioreactor system may provide a system with minimal water loss perhaps in a closed bioreactor system and may even provide substantially no contamination perhaps in a closed system. This may be achieved by utilizing valves or the like to prevent leaks. A bioreactor system may include systems that provide flowing a fluid through a tubing component, adding microorganisms to a fluid in a tubing component, adding nutrients to a fluid in a tubing component, modifying a flow of the microorganisms in a fluid, degassing—of oxygen for example, and perhaps even harvesting grown microorganisms from a fluid, or the like. A bioreactor system may be run continuously or even quasi-continuously.

A tubing component (2) may be any kind of hollow body of glass, rubber, plastic, opaque plastic, metal, glass lined steel pipes, stainless steel, polycarbonate, acrylic, polyvinyl chloride, acrylonitrile-butadiene-styrene, concrete, earth (for perhaps furrowed fields or the like), and any combination thereof or any other material that may convey or even contain liquids. A tubing component may be a cylindrical body, a pipe, duct, chute, a preformed circular tubing, a cylindrical tubing, or the like and may even be transparent, opaque, or the like. When a tubing component may be clear it may allow light to be transmitted to the items contained therein such as for phototrophic or even mixotrophic microorganisms. In some embodiments of the present invention, phototrophic or mixotrophic microorganisms may be used with a glass or even plastic tubing; heterotrophic microorganisms may be used with opaque plastic tubing (like white PVC, for example) or perhaps even any one of various metals, glass lined steel pipes, or the like.

A fluid flow impetus (12) may be anything that may cause motion to a fluid in a tubing component such as but not limited to a motor, air, valve, pump, gravity, a combination of a pump and gravity, power supply, or the like. A fluid may be a substance such as a liquid, gas, a mixture of liquid and gas, including but not limited to: a slurry of liquid, gases, and solids; a slurry with microorganism solids; liquid medium; water; dilute polymer solution; polymer solution; aqueous solution, wastewater; or the like. A fluid flow impetus may be capable of creating a fluid flow (13) of a fluid in a direction and perhaps even with microorganisms, nutrients, biomass, or other materials that may be added to a fluid, or the like through a tubing component. A fluid flow impetus may provide a low mean flow speed to a fluid flow. A low mean flow speed may include but is not limited to about 1 inch/second, about 0.5 inch/second, about 1.5 inches/second, about 2 inches/second, about 3 inches/second, about 4 inches per second, about 5 inches per second, about 6 inches per second, greater than about 6 inches/second, or the like. A low mean flow speed can be the order of about 1 inch/second and may still create an enhanced mixing. Of course, any required mean flow speed may be utilized in the various embodiments of the present invention and all are meant to be included in this disclosure. A fluid flow impetus may create a downstream fluid flow as may be discussed herein. In some embodiments a fluid flow impetus may provide a continuous mixing element in that it may provide continuous mixing of all the fluid and other constituents with its flow.

In some embodiments, a bioreactor system may include a gas input (22) which may add at least one gas to a tubing component. A gas input may be configured to add gas into a tubing component. A gas input may be the same as an input (5) or may be different. There may be one, at least one, multiple, or more inputs, input locations, input at preferred locations, or even gas inputs in a system, or the like. A gas input may be any kind of device that may allow a gas to be added to a tubing component. Gas (95) added to a system may include but is not limited to oxygen, carbon dioxide, carbon dioxide effluent, air, or the like. A gas input (22) may be a continuous gas input perhaps configured to continuously add gas into a tubing component. A gas release (21) may be included in a bioreactor system which may be any kind of device that may allow releasing of a gas from a tubing component. Embodiments of the present invention may provide a gas release, at least one gas release, multiple gas releases, or more than one gas releases, or the like. Released gas may include but is not limited to oxygen or carbon dioxide such as by an oxygen gas release or even a carbon dioxide release or the like. A gas input or even a gas release may be a valve, spout, nozzle, outlet or the like.

Various kinds of microorganisms may be used in embodiments of the present invention such as but not limited to algae, bacteria, archaea, protozoa, fungi, viruses, phototrophic microorganisms, heterotrophic microorganisms, mixotrophic microorganisms, cyanobacteria, microalgae, phototrophic algae, microphototrophic algae, heterotrophic algae, highly alkaline algae, acidic algae, or the like.

An output (98) may be any kind of device that may allow something to exit or even be removed from a tubing component including but not limited to a valve, spout, nozzle, outlet or the like. An output (98) may remove outputted components (84) from a tubing component such as but not limited to gases, microorganisms, or the like. An output may be a continuous microorganism output where it may continuously remove microorganisms from a tubing component. Embodiments of the present invention may include at least one system constituent (16) which may include but is not limited to a pH adjuster, a temperature adjuster, a constant temperature control, a growth stimulator input, pH meter, optical density measurement, carbon dioxide analyzer, oxygen analyzer, a sequential feeder of gases or nutrients or the like, a sequential monitor, a sequential gas release, monitoring equipment or the like. For example a constant temperature control may provide a constant temperature in a bioreactor system which may be achieved by, but not limited to, controlled space heating, tubing wrapped with heat tape, tubing wrapped with heat wire, using water temperature control for tubing placed in water channels, using water temperature control for tubing placed in ponds, or the like. A tubing element may be heated in hot oil or hot air hot sand or the like. Embodiments of the present invention may provide monitoring fluid in a tubing component such as but not limited to: adjusting a pH of a fluid in a tubing component; adjusting a temperature of a fluid in a tubing component; adding a growth stimulator to a fluid in a tubing component; providing a pH meter; providing an optical density measurement; analyzing carbon dioxide in a fluid; analyzing oxygen in a fluid; monitoring a bioreactor system; or the like. Embodiments of the present invention may provide sequential feeding of at least one gas and perhaps even nutrients or the like to a fluid in a tubing component; monitoring a step of sequential feeding of at least one gas and perhaps even nutrients or the like to a fluid in a tubing component; sequentially releasing at least one gas from a tubing component, or the like. Sequential may be a particular order of events that may be desired.

Embodiments of the present invention may provide a program (26) that may allow a system to be automated such as but not limited to programmatically adding nutrients into a tubing component. A program may be a computer program that may analyze an upstream state of the microorganisms growth and may determine an amount of $CO_2$ (or other gas), nutrients, Ph buffering, a temperature change, or the like that may be needed to be added to, or even removed from, a bioreactor flow perhaps at some downstream location of a tubing component perhaps to foster optimal microorganism growth. Nutrients (11) may include but are not limited to carbon dioxide, carbon sources, oxygen, nitrogen, phosphorous, potassium, wastewater, sugars, chemicals, any substance needed to achieve a desired result, any combination or permutation herein, or the like.

Figure 19:
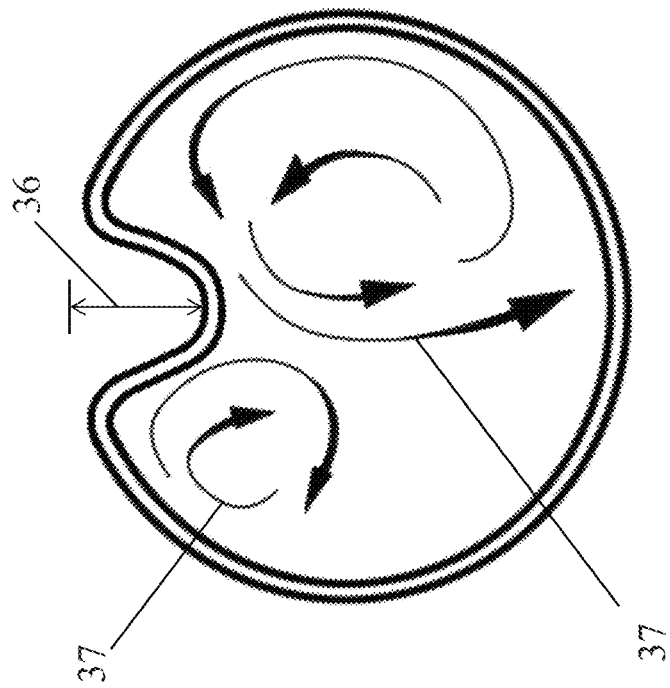
FIG. 19 shows another example of the projection of the paths of selected fluid particles traveling over some downstream distance, onto the chosen cross-sectional plane of a tubing component having an inwardly protruding helical spine with cross flows in accordance with some embodiments of the present invention.
Figure 18:
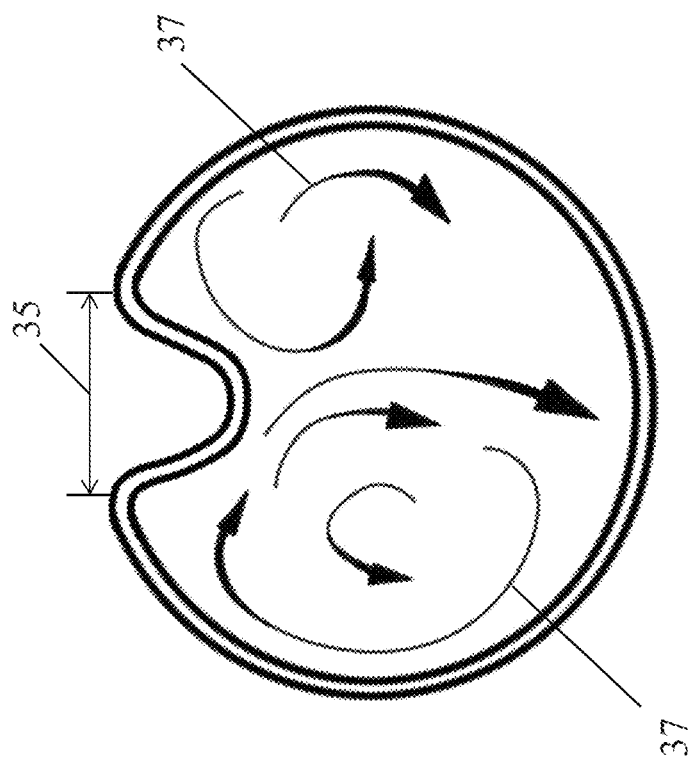
FIG. 18 shows an example of the projection of the paths of selected fluid particles traveling over some downstream distance, onto the chosen cross-sectional plane of a tubing component having an inwardly protruding helical spine in accordance with some embodiments of the present invention.

Embodiments of the present invention may provide a fluid flow coordinator (92) perhaps capable of inducing unsteady multiscale cross flows (37) within a fluid and even capable of promoting microorganisms to disperse (27) within a fluid in a tubing component. This may include continuously inducing unsteady multiscale cross flows within a fluid such that it may provide continuous unsteady separation of fluid. Continuous flows and flow separations, or the like may provide separations or inducing of an element that may not be interrupted, may be steady, may produce a stochastic distribution, may be consecutive, may be perpetual, or the like. A fluid flow coordinator (92) may be any kind of design, method, apparatus, flow modifier, protrusion, spine, or the like that can promote dispersion of microorganisms and perhaps other components in a fluid perhaps with the help of inducing unsteady multiscale cross flows in the fluid. As discussed herein, it may be desirable to move microorganisms around an inside of a tubing component perhaps for sufficient mixing or even to allow the microorganisms to move to and away from light coming in through a tubing component. FIGS. 18 and 19 show examples of unsteady multiscale cross flows (37) the projection of who's particle paths over a given downstream distance are drawn onto the cross-sections depicted, that may be desirable for proper mixing of the components in a fluid. As may be understood from these figures, cross flows may be random, irregular, uneven, unstable, in varying degrees, in multiples, or the like. In some embodiments, the present invention may provide cross-flows or even unsteady multiscale cross-flows that are non-vortex flows. Organized vortexes may contain microorganisms in a whirling mass so that the microorganisms may not be able to disperse from the vortex. Unsteady multiscale cross-flows may be characterized by continuously variable spiral churning of multiscale cross flows and may even occur at any scaling of the various embodiments of the present invention including but not limited to scaling based on a tubing component's diameter. A dispersion (27) of microorganisms within a fluid in a tubing component may include scattering, driving in various directions, disseminating, dispelling, or the like of the microorganisms within a fluid. Dispersion of microorganisms may be uneven, within, across, substantially across, from one side to another, from about one side to another, or the like of a tubing component. Dispersion of microorganisms may be substantially dispersive. This may occur as the fluid flow moves along so that the dispersion may occur in all directions, vertically, diagonally, horizontally, or the like throughout the tubing. A non-limiting example of dispersion (27) of microorganisms may be understood in FIGS. 28-31 and 79. FIGS. 28, 29, 30, 31, and 79 show photographs of a movement of a dye (dissolved in a dilute polymer solution) that has been injected into a tubing component filled with water. The polymer dye paths are shown at random times and the dye may be representative of a dispersion (27) of microorganisms perhaps having movement across an entire cross-section (38) of a tubing component. A fluid flow coordinator can encompass any type of method or system that can create these types of cross flows or dispersions.

Figure 17:
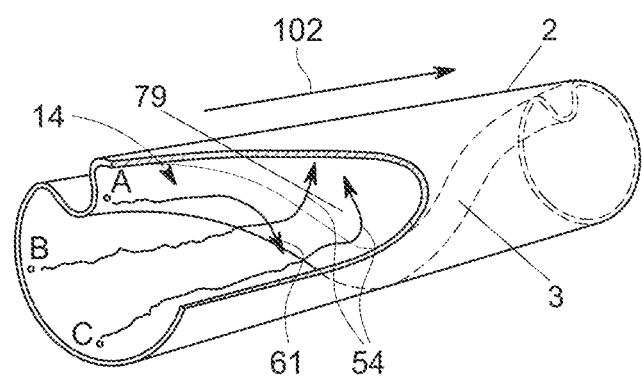
FIG. 17 shows a cutaway view of an example of an inside of tubing component having an inwardly protruding helical spine showing its effects on the fluid particle's paths resulting in their cross-flows in accordance with some embodiments of the present invention.

Other embodiments of the present invention may provide a passive microorganism flow modifier (93) perhaps capable of passively generating cross flows (61) in a fluid perhaps substantially throughout a tubing component and may even be capable of promoting dispersion (27) of microorganisms substantially within a fluid in a tubing component. FIG. 17 provides a non-limiting example of a cross flow (61) which may include a fluid flow that may be non-linear, that can move from one side to another, that may move in multi-dimensions, that may be indefinite, may be unconfined, or the like. Cross-flows may be unsteady multiscale cross flows as discussed herein. Cross-flows or even unsteady multiscale cross flows may be generated or even continuously generated passively perhaps a by passive microorganism flow modifier in that there may be no moving parts, or activity associated with the flow modifier such that it may be inactive, inert, quiescent, or the like. Cross-flows may move substantially throughout a tubing component allowing dispersion of microorganisms substantially within a fluid perhaps so that microorganisms may have movement across an entire cross-section (38) of a tubing component and may even promote movement along the fluid as it moves downstream perhaps so that the dispersion may occur in all directions, vertically, diagonally, horizontally, or the like throughout the tubing. A passive microorganism flow modifier or embodiments which provide passively modifying a flow of a fluid can encompass any type of method or system that can create the types of cross-flows or dispersions discussed herein.

In some embodiments, it may be desirable to have a fluid coordinator or even a passive microorganism flow modifier that may not create high shear stress which may damage the microorganisms, may not remove a lot of energy from a flow, may not require a lot of energy to operate, may not be intermittent, may be a vortex generator, may not have highly correlated flows, or the like. Of course, in the alternative, these elements may be used in some embodiments of the present invention. In some embodiments of the present invention, a fluid flow coordinator or even a passive microorganism flow modifier may be located inside a tubing component.

Embodiments of the present invention may provide a bioreactor system comprising a tubing component comprising an inwardly protruding helical spine along an inside surface of at least part of said tubing component; a fluid input configured to add a fluid into said tubing component; an inoculate input configured to add microorganisms into said tubing component; a nutrient input configured to add nutrients into said tubing component; and perhaps even a fluid flow impetus capable of creating a fluid flow of said fluid, said microorganisms, and said nutrients through said tubing component.

Other embodiments of the present invention may provide a method for a biologically active environment comprising the steps of flowing a fluid through a tubing component, wherein said tubing component comprises an inwardly protruding helical spine along an inside surface of at least part of said tubing component; adding microorganisms to said fluid in said tubing component; adding nutrients to said fluid in said tubing component; modifying a flow of said microorganisms in said fluid with said inwardly protruding helical spine of said tubing component; and perhaps even harvesting grown microorganisms from said fluid.

Embodiments of the present invention may provide a method for a biologically active environment comprising the steps of flowing a fluid throughout a transparent tubing component, wherein said tubing component comprises an inwardly protruding helical spine along an inside surface of at least part of said tubing component; adding algae to said fluid in said transparent tubing component; adding nutrients to said fluid in said transparent tubing component; adding at least one gas into said transparent tubing component; exposing at least some of said transparent tubing component to a lighting element; passively generating unsteady multiscale cross flows in said fluid containing said algae substantially throughout said transparent tubing component; promoting dispersion of said algae substantially within said fluid in said transparent tubing component; and perhaps even harvesting grown algae from said fluid.

Other embodiments of the present invention may provide a bioreactor system comprising a transparent tubing component; a fluid input configured to add a fluid into said transparent tubing component; an inoculate input configured to add algae into said transparent tubing component; a nutrient input configured to add nutrients into said transparent tubing component; a fluid flow impetus capable of creating a fluid flow of said fluid, said algae, and said nutrients through said transparent tubing component; at least one gas input capable of adding a gas to said fluid in said transparent tubing component; at least one lighting element capable of providing light to at least part of said transparent tubing component; an inwardly protruding helical spine along an inside surface of at least part of said tubing component capable of passively generating cross flows in said fluid substantially throughout said transparent tubing component and promoting dispersion of said microorganisms substantially within said fluid in said transparent tubing component; continuously exposing said microorganisms to said nutrients, light from said lighting element, and said at least one gas; and perhaps even an algae collector attached to said tubing component.

Figure 11:
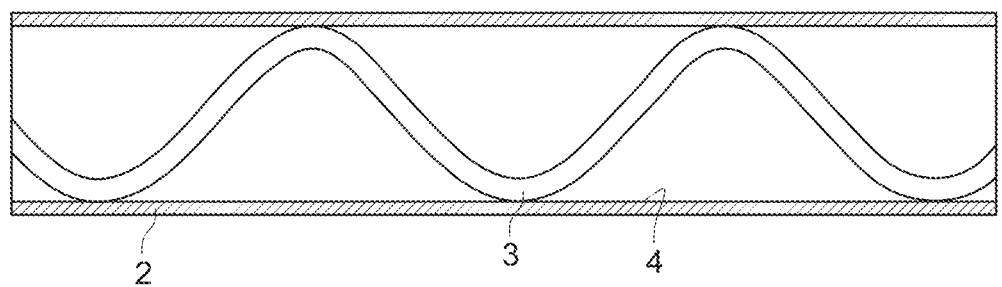
FIG. 11 shows an example of a tubing component with an inwardly protruding helical spine in accordance with some embodiments of the present invention.

Embodiments of the present invention may provide a tubing component having an inwardly protruding helical spine along an inside surface of at least part of a tubing component. FIG. 11 provides a non-limiting example of a tubing component (2) having an inside surface (4) and an inwardly protruding helical spine (3). An inwardly protruding helical spine may be a projection, bulge, extension, or the like perhaps inward such as toward an inside, interior, center, or the like of a tubing component perhaps so that a fluid flow may come into contact with it. An inside surface of a tubing component may be an inside of a hollow tube, pipe, or the like. A helical spine may be present along at least part of a tubing component, may be along an entire tubing component, or the like. Part of a tubing component may be between about 10% and about 100%. A helical spine or any type of fluid flow coordinator or passive microorganism flow modifier or the like may be applied along a wall of a system such as but not limited to a channel wall of a closed channel flow system.

Figure 12:
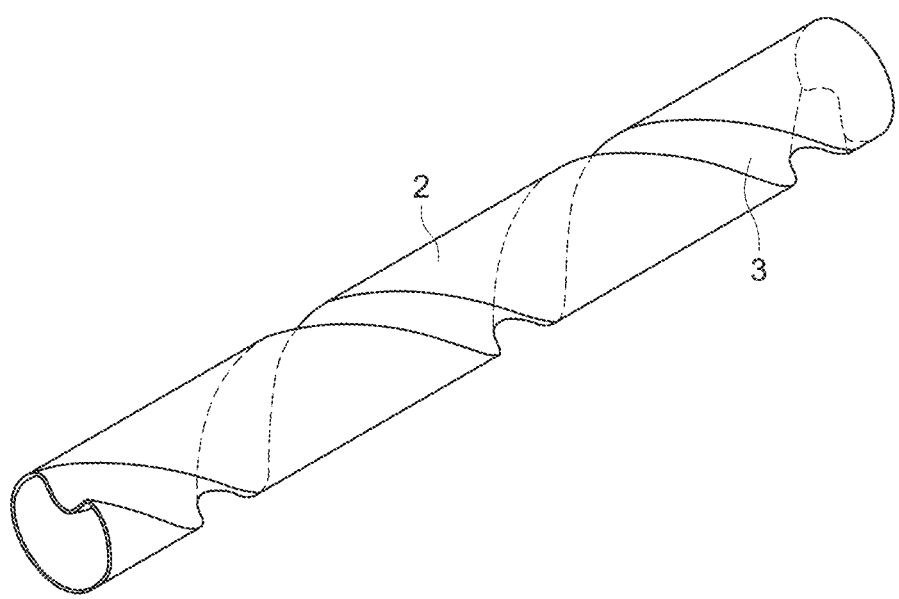
FIG. 12 shows an isometric view of an example of tubing component having an inwardly protruding helical spine in accordance with some embodiments of the present invention.
Figure 13:
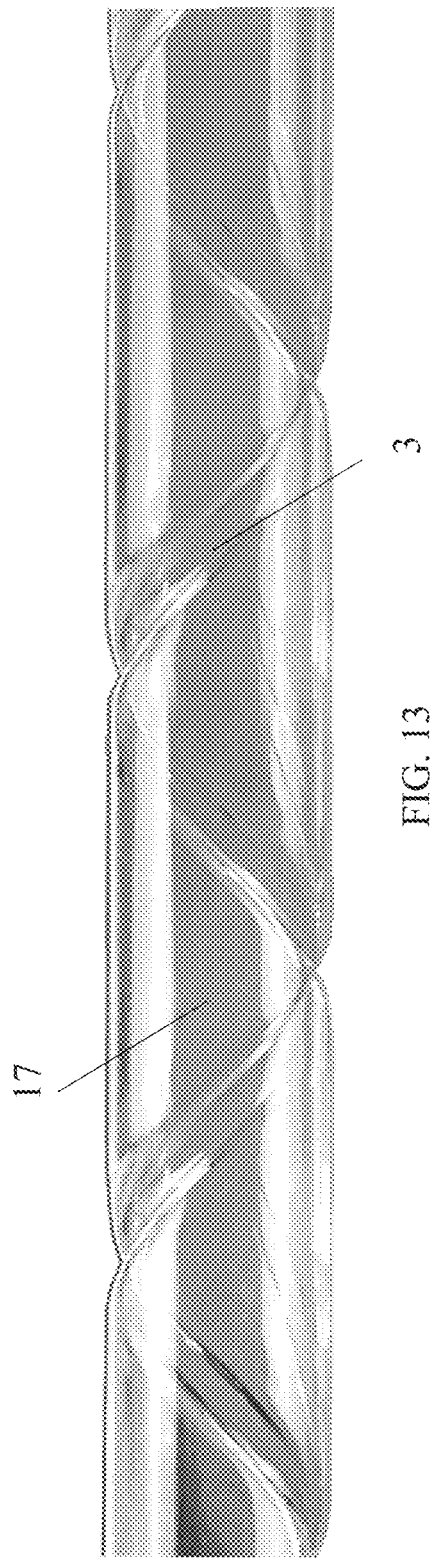
FIG. 13 shows an example of an acrylic pipe in accordance with some embodiments of the present invention.
Figure 14:
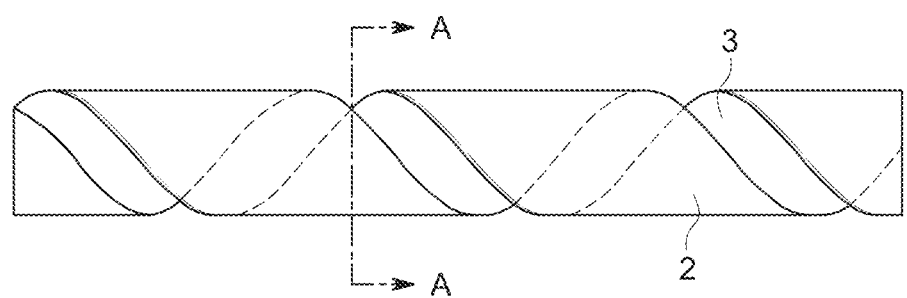
FIG. 14 shows a top view of an example of tubing component having an inwardly protruding helical spine in accordance with some embodiments of the present invention.
Figure 15:
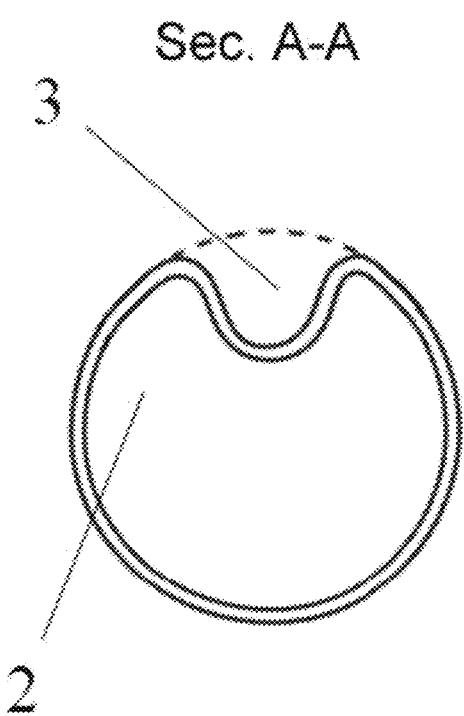
FIG. 15 shows an example cross-section of a tubing component having an inwardly protruding helical spine at Sec. A-A of FIG. 14 in accordance with some embodiments of the present invention.

FIG. 12 shows an isometric view of an example of tubing component having an inwardly protruding helical spine and FIG. 14 shows a top view of an example of tubing component having an inwardly protruding helical spine. FIG. 15 shows an example cross-section of a tubing component having an inwardly protruding helical spine at Sec. A-A of FIG. 14. FIG. 13. shows an example of an acrylic tubing component (17) with an inwardly protruding helical spine (3). A cross section of an inwardly protruding helical spine may be symmetric or it may even be asymmetric.

Embodiments of the present invention may provide that an inwardly protruding helical spine (3) may be capable of inducing unsteady multiscale cross flows (37) within a fluid and may even be capable of promoting microorganisms to disperse (27) within a fluid in a tubing component as may be discussed herein. This may provide continuous exposing of microorganisms to light and to nutrients, including $CO_2$, as the microorganism may flow throughout a tubing component.

FIG. 17 shows an example of an inside of a tubing component (2) where an inwardly protruding helical spine (3) may affect the fluid flow (102) of a fluid. In the figure are three examples of pathlines of algae particles as they may approach an inwardly protruding helical spine and get separated from it along with the flow, creating cross-flows (61). These three examples represent three algae cells A, B, and C that are initially at the cross-section shown in FIGS. 16 and 17 and how they may proceed to move down a tubing component in a downstream fluid flow (79). The flow of the fluid and the algae may be modified (14) by the inwardly protruding helical spine perhaps creating separated flows (54) and even unsteady separation of fluid flow. In particular, this figure shows an example of a large change in direction that the algae undergo as the flow they are in undergoes separation from the inwardly protruding helical spine. Embodiments of the present invention may provide an inwardly protruding helical spine that may be configured to separate flows (54) and perhaps combined with an unsteady magnitude and direction of approach flows, may prevent fluid flow reattachment of the separated flows perhaps in the immediate region downstream (79) of a protruding helical spine.

FIGS. 18 and 19 provide examples of a cross-section of a tubing component having an inwardly protruding helical spine showing flow fields that may occur in the cross-flow direction perhaps as a result of inwardly protruding helical spine. These are examples of short time segment projections of the pathlines of the cross-flow motions projected onto these specific cross-sections. FIG. 18 illustrates an instant that a cross flow approaches a helical spine coming from the left of the page. It may separate somewhere in the vicinity of the greatest depth of an intrusion of the spine and the flow may then be directed towards the center of the pipe. Instantaneously an unsteady recirculating region may form behind the intrusion of the spine, circulating in the other direction. FIG. 19 illustrates an instant that a cross flow may come from the right of the page. It will destroy the recirculating region, and although it will be different in magnitude and coming from somewhat different direction, but it will also separate from the intrusion in the vicinity of the intrusion's maximum height, and also be directed into the center of the pipe. The separated flows sometimes may show the existence of shed vortices, and these shed vortices may quickly break down perhaps producing turbulent energy. This series of events may occur all along the entire length of the helical spine, which, again, may extend all along the length of a tubing component. The unsteady nature of the cross flows, such as unsteady multiscale cross flows (37), may enable them to approach an inwardly protruding helical spine from any direction. FIGS. 18 and 19 provide a non-limiting example of a width (35) and depth (36) of an inwardly protruding helical spine that can result in these motions as discussed further herein.

Figure 22:
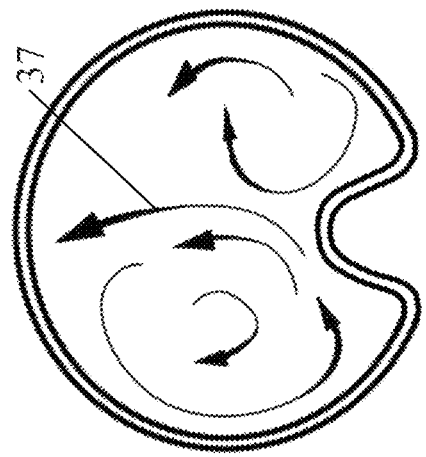
FIG. 22 shows an example cross-section of a tubing component having an inwardly protruding helical spine at about a 180-degree angle with cross flows in accordance with some embodiments of the present invention.
Figure 21:
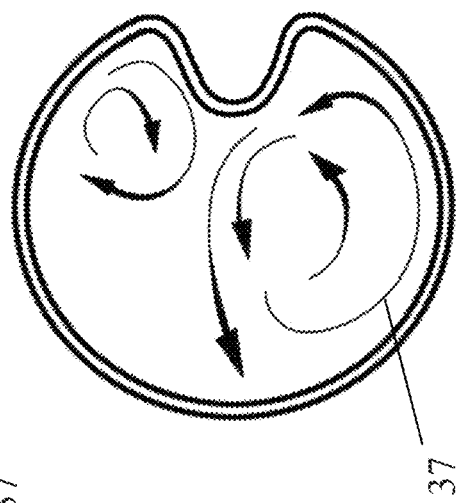
FIG. 21 shows an example cross-section of a tubing component having an inwardly protruding helical spine at about a 90-degree angle with cross flows in accordance with some embodiments of the present invention.
Figure 20:
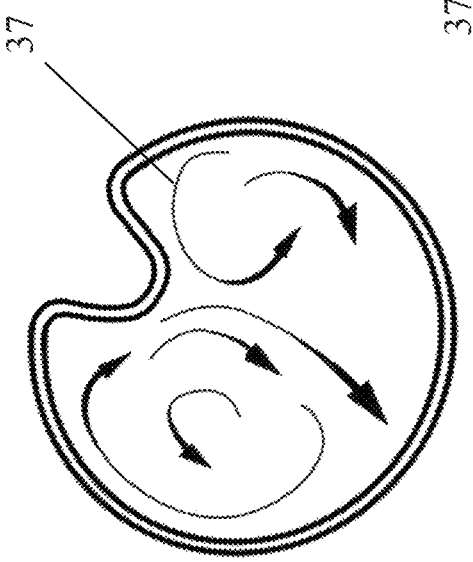
FIG. 20 shows an example cross-section of a tubing component having an inwardly protruding helical spine at about a 45-degree angle with cross flows in accordance with some embodiments of the present invention.

At different stations along a bioreactor (i.e., along the length of the tube component), as a result of the helical spine, the cross-flows may be directed towards other parts of the tubing wall as shown in FIGS. 20-22. FIGS. 20-22 show one example of the cross-sectional views of the projections of the pathlines at different downstream sections of the tubular bioreactor, in particular, at a downstream location along an inwardly protruding helical spine such that spine may have moved at about 45 degrees (FIG. 20), at about 90 degrees (FIG. 21), and at about 180 degrees (FIG. 22) respectively from the position in FIG. 18. Of course, in any of these images, a cross-flow may come to an inwardly protruding helical spine from any direction.

Figure 23:
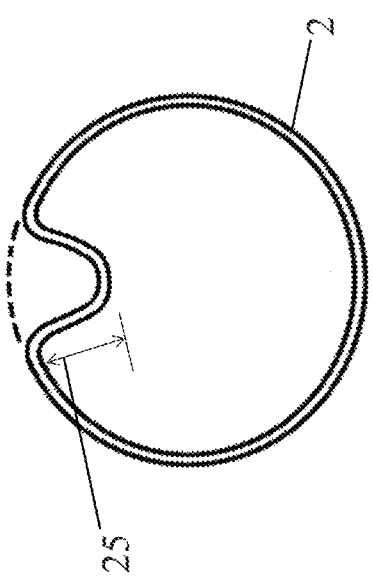
FIG. 23 shows an example of an inwardly protruding helical spine made by an indent in accordance with some embodiments of the present invention.
Figure 24:
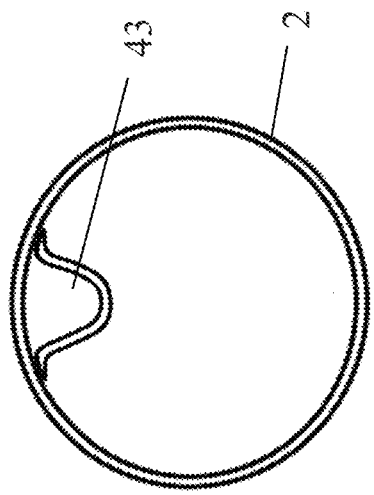
FIG. 24 shows an example of an inserted inwardly protruding helical spine in accordance with some embodiments of the present invention.
Figure 25:
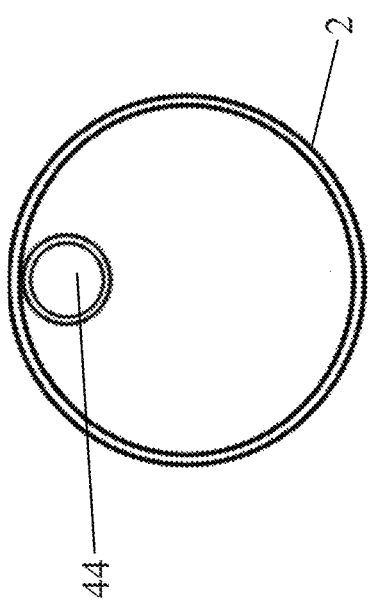
FIG. 25 shows an example of an inwardly protruding helical spine made by inserting a spiraling tube into a tubing component in accordance with some embodiments of the present invention.
Figure 26:
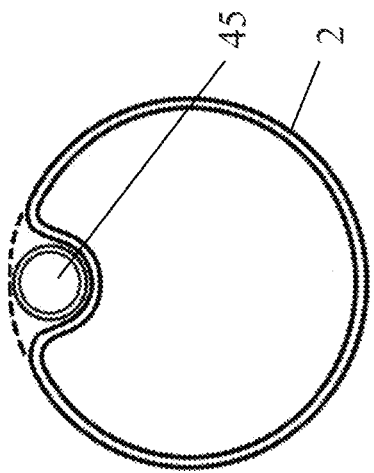
FIG. 26 shows an example of an inserted inwardly protruding helical spine made by indenting a flexible tubing component in accordance with some embodiments of the present invention.

In some embodiments, an inwardly protruding helical spine may be achieved in a tubing component perhaps by inserting a spiraling tube (44) or even a spiraling shape (43) into a tubing component (2) perhaps to provide an inserted inwardly protruding helical spine. A tube may be a flexible tube or even a rigid tube. In other embodiments, an inwardly protruding helical spine may be achieved in a tubing component perhaps by extrusion or even molding a tubing component perhaps to provide an extruded inwardly protruding helical spine or even a molded inwardly protruding helical spine. Extrusion may include forming, pressing out, expelling, or the like of a tubing component to create a desired shape. A molded inwardly protruding helical spine may be a tubing component that is shaped into a particular shape. A shape (43) of an insert or even a shape of an inwardly protruding helical spine may be any kind of shape such as but not limited to rounded contours, circular cylinders, streamlined shapes, airfoil shapes, or the like. Bioreactor systems may utilize hydroforming techniques or the like. FIG. 23 shows a non-limiting cross-section of inwardly protruding helical spine perhaps made by indenting (25) tubing component (2), perhaps either during manufacture or even after. FIG. 24 shows a non-limiting cross-section of inwardly protruding helical spine perhaps made by inserting a shape (43) into a tubing component (2). FIG. 25 shows a non-limiting example of a cross-section of inwardly protruding helical spine perhaps made by inserting a spiraling tube (44) into a tubing component (2). FIG. 26 shows a non-limiting example of a cross-section of a method for indenting (45) a tubing component (2) such as flexible tube, perhaps made of silicone or the like. In some embodiments, the present invention may be made by sequentially impressing an inwardly protruding helical spine into a preformed circular or even a cylindrical tubing component.

A helical spine may be a continuous helical spine or may even be a substantially continuous helical spine perhaps so that cross-flow fluid motions created by a helical spine create sufficiently frequent forcing on the fluid that we can bring microorganisms to the light at the walls perhaps with the same frequency as could occur with a fully continuous helical spine. A length of a cross flow travel of a cell after it may leave the vicinity of the wall may be shortened perhaps due to fluid motion decay mechanisms which have more time to act do to gaps in the spine. The gaps prevent continual reinforcement of the cross flows. However, as long as the forcing could bring the cell to the wall region, and hence may enable it to gather the photons of light it requires for growth, embodiments of the present invention may provide a substantially continuous helical spine forcing function.

For those embodiments of the present invention that may relate to a helical spine or the like that may be only partially located inside a tubing component or the like may have at least one gap (28), or the like, it may not matter if cross flow have decayed enough to prevent continued movement of a cell away from the wall perhaps to a quarter, half radius, or any other position within a tubing component as it may come away from a wall, perhaps as long as the cell may find itself in a next cross-stream current perhaps created by a continuation of a spiraling intrusion perhaps after a gap.

Embodiments of the present invention may provide a helical spine that may cover a sufficient amount of a pipe's interior perhaps so that crossflow motions that it may create may not have time to decay perhaps before receiving another impulse from a helical spine. If the motions have time to decay, they may not continue to provide the superior mixing that may be created by a continuous helical spine. The helical spine could cover a significant portion of a pipe perhaps so as to constantly apply a forcing to the fluid, and thus may produce a stochastically steady state (e.g., the probabilities that various mixing states can be repeated and can remain constant) of mixing at each cross-section of the tubing component. If gaps in a helical spine are too large, the flow it may produce can decay as it moves downstream and perhaps before it may encounter another portion of a spine again. This may result in a condition of increasing mixing at some locations and decreasing mixing at other locations, perhaps depending on where the microorganism is located with respect to the helical spine sections in the tubing component.

A helical spine may interact with a significant portion of a flow fluid perhaps continually and even all along a tubing component. A local effect of any forcing function from a helical spine or any other fluid flow modifier which can create the cross flows and thus create mixing may quickly decay as the fluid moves away, perhaps downstream of it. A decay may occur continually, perhaps as a result of the nature of fluids through naturally occurring non-linear turbulence energy transfer and the effect of viscosity. This may not be preventable. It may be desirable to have a forcing function that may be repeated again and again perhaps so that it may be active over a significant portion of a tubing component which may continually impart energy to force the fluid to move across a tubing component. This may allow a same intensity and even quality of mixing during an entire life of the processes.

For a given length of pipe, any length of a helical spiral, or even combinations of lengths of segments of helical spirals can enhance cross flow mixing. Thus, in a pipe of length x, one section of helical spiral of length x/10, for example, can locally enhance the cross-flow velocities and perhaps even the mixing. Whereas five sections of a helical spiral, each of a length x/10, may be spaced apart over the length of the pipe and can further enhance the cross flows and the mixing. Of course, some embodiments may utilize an almost continuous length of helical spiral over an entire length of pipe.

Figure 27:
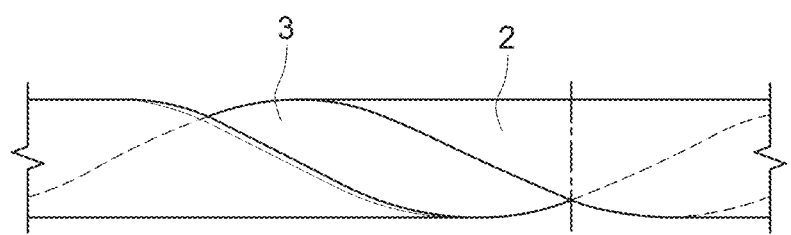
FIG. 27 shows an example of a tubing component having an inwardly protruding helical spine in accordance with some embodiments of the present invention.
Figure 28:
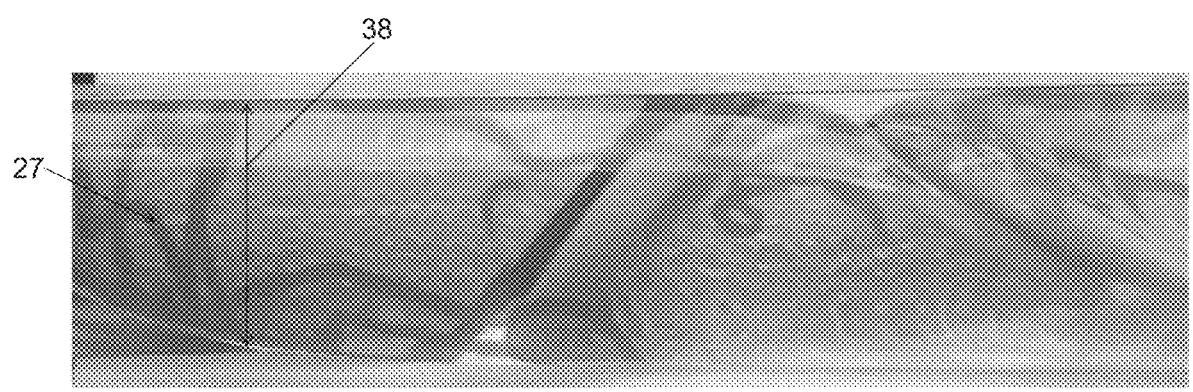
FIG. 28 shows a photograph of movement of a dye injected into a tubing component having an inwardly protruding helical spine in accordance with some embodiments of the present invention.
Figure 29:
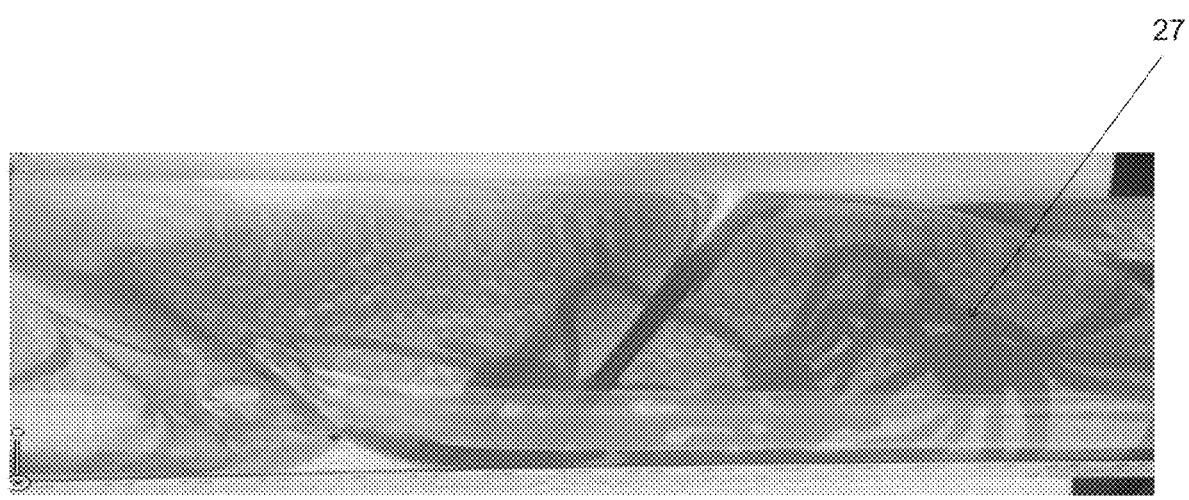
FIG. 29 shows a photograph of movement of a dye injected into a tubing component having an inwardly protruding helical spine in accordance with some embodiments of the present invention.

FIG. 27 shows an example of a tubing component (2) having an inwardly protruding helical spine (3). FIGS. 28 and 29 show photographs of a movement of a dilute polymer dye that has been injected into a tubing component with an inwardly protruding helical spine. The polymer dye paths are shown at two random times. The dye may be representative of a dispersion (27) of microorganisms perhaps having movement across an entire cross-section (38) of a tubing component. These motions may provide a Growth Enhancing Mixing Spectrum ("GEMS"). In FIGS. 28 and 29 experiments were conducted using about 6" diameter clear acrylic pipe. Some experiments have been done with pipes ranging from about 1.5 inches to about 8 inches in diameter.

Figure 30:
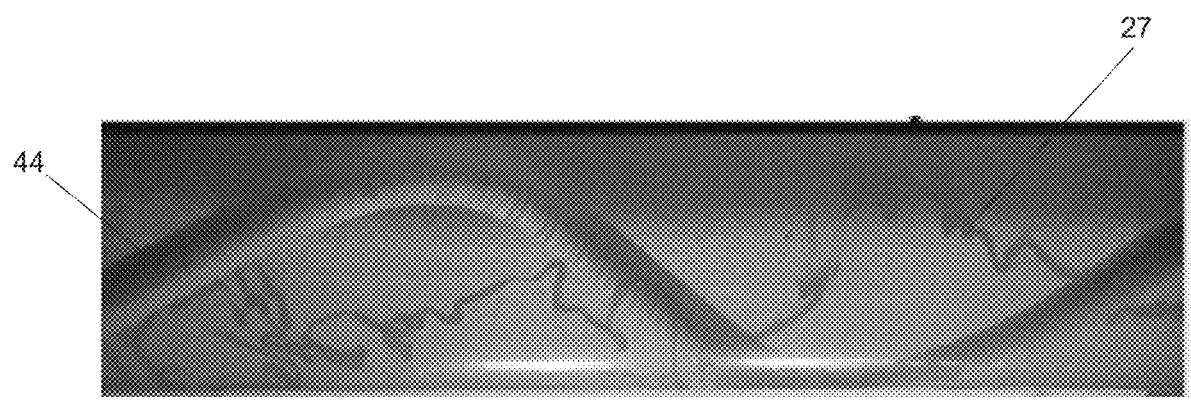
FIG. 30 shows a photograph of movement of a dye injected into a tubing component having an inserted inwardly protruding helical spine in accordance with some embodiments of the present invention.
Figure 31:
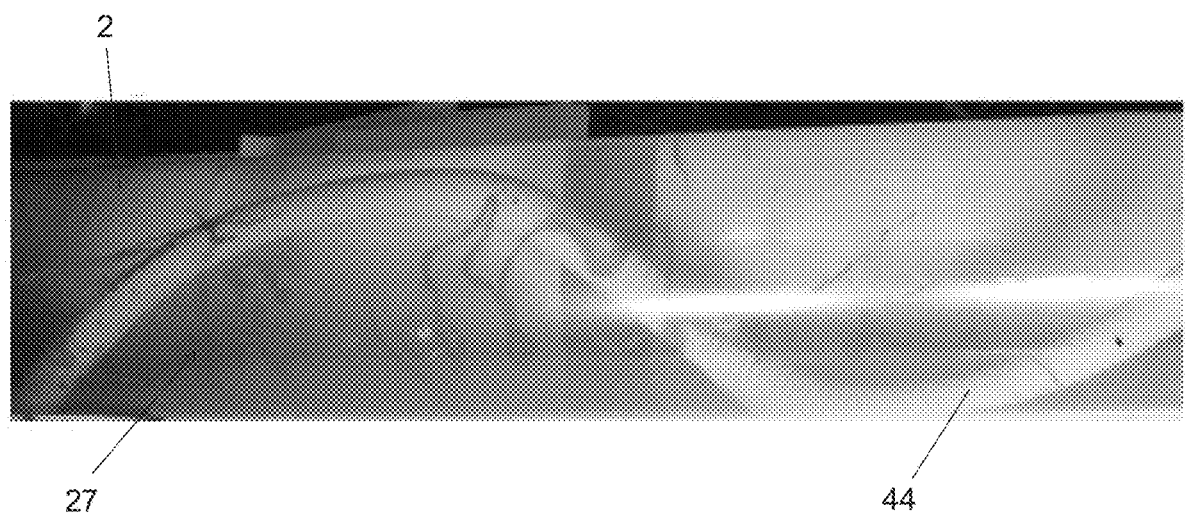
FIG. 31 shows a photograph of movement of a dye injected into a tubing component having an inserted inwardly protruding helical spine in accordance with some embodiments of the present invention.

FIGS. 30 and 31 show an example of the movement of a dye (in a dilute polymer solution) in a tubing component in which the spiral intrusion (44) was created by spiraling tube being placed the tubing component (2). The polymer dye paths are show at two random times. Again, the dye may be representative of a dispersion (27) of microorganisms. In FIGS. 30 and 31, experiments were conducted using about 8" diameter clear PVC pipe with 1¼-inch spiraled tubing inside.

Figure 42:
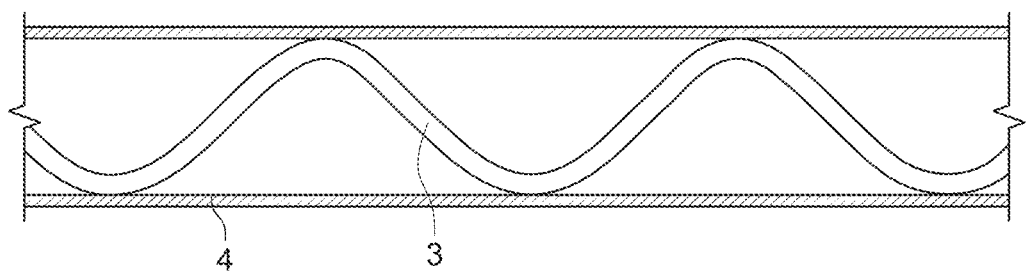
FIG. 42 shows an example of a continuous inwardly protruding helical spine in accordance with some embodiments of the present invention.
Figure 43:
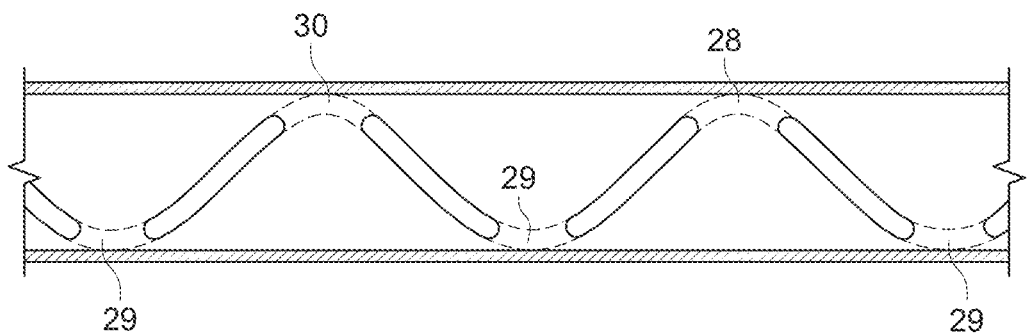
FIG. 43 shows an example of a segmented inwardly protruding helical spine in accordance with some embodiments of the present invention.

Embodiments of the present invention may provide at least one gap (28) in an inwardly protruding helical spine or the like. A gap may be a space, opening, break, interval, or the like in a helical spine or perhaps even between segments of a helical spine. FIG. 42 shows an example of a continuous inwardly protruding helical spine (3) located along an inside surface (4) of a tubing component. An inwardly protruding helical spine may not need to be continuous and may have individual segments, perhaps taking on an overall helical character that can create separation which may result in cross flows. An inwardly protruding helical spine may include at least one gap (28) which may be evenly spaced (29) along an inwardly protruding helical spine and may even be located along a top inside (30) of a tubing component as may be understood from FIG. 43. Gaps do not necessarily have to be evenly spaced, or of the same widths. Gaps may be provided for gas transport. Some embodiments may provide a plurality of gaps in a helical spine. A shape of a gap or even individual segments may have any shape. It may be desirable to provide a shape that can keep the shear stress low enough so as to not destroy the algal cells. For example, an "on-ramp" and an "off-ramp" of a segment may provide gentle transitions.

Embodiments of the present invention may address gas bubbles that may occur in a bioreactor system. When used with phototrophic algae or the like, $CO_2$ may need to be introduced into a tubing component and the algae grows, they may emit $O_2$. When used with heterotrophic algae, $O_2$ or air may need to be introduced and as they grow, they may generate $CO_2$. Thus, gas may be present in a bioreactor system and removal of gas (e.g., oxygen for phototrophic algae or carbon dioxide for heterotrophic algae) and perhaps even proper distribution of gas among the algae cells within a tubing component may be desired. Since gases may be lighter than water, they may accumulate at a top of the pipes and may accumulate upstream of spiral indents of a helical spine perhaps at a top of the pipe, which may act as a barrier to the gas flow that may be present every spiral rotation. Gas bubbles can accumulate on an upstream side of a piece of a spiral indentation, perhaps resulting in rather large gas bubbles forming, which can inhibit an effect of the spiral on the flow, and may even prevent the distribution of gases like $CO_2$ that may be perforable. A gas flow inhibition may be prevented perhaps by making a passageway at a top of a helical spine. A size of that gap could depend on an angle that the tubing components may be laying at, a flow speed within the tubing component, or even a diameter of the tubing component. Thus, size and scale of gaps and a passageway may vary.

Figure 44:
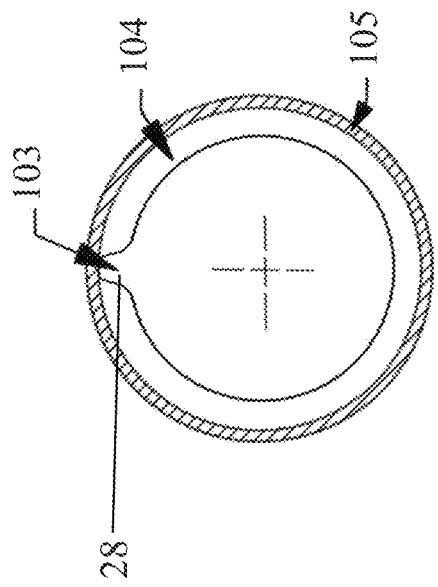
FIG. 44 shows an example end view of a cross-section of a tubing component with a gap in accordance with some embodiments of the present invention.
Figure 45:
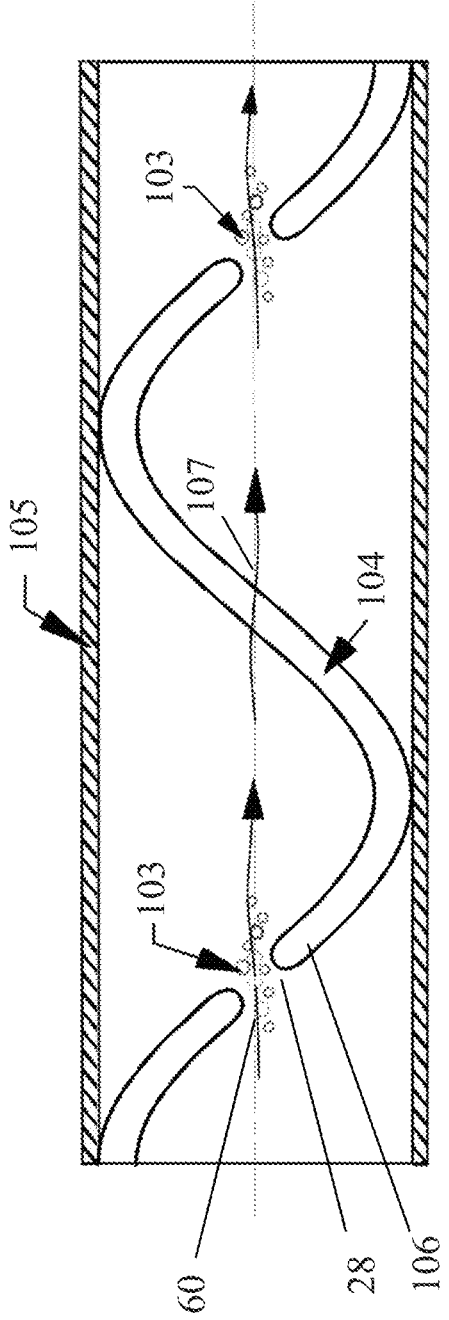
FIG. 45 shows an example top view of a tubing component showing gaps in a helical spine and gas bubble movement in accordance with some embodiments of the present invention.

FIGS. 44 and 45 shows a representation of a gap in a helical spine at a top of a tubing component that may allow gas bubbles to pass through. FIG. 44 shows an end view cross section of a tubing component where a gap (28) in an inner groove of a helical spine (104) may be located at an inside top (103) of a tubing component (105). FIG. 45 shows a top view of a segment of a tubing component (105) having a gap (28) in an inner groove of a helical spine (104) which may be located at an inside top (103) of a tubing component (105). Bubbles (60) perhaps even unstable, short lived separation bubbles may be unevenly distributed along a helical spine (104). A possible path (107) of the gas bubbles may be understood from FIG. 45, although it may represent the average movement of the gas bubbles along the tubing component, as they may also experience strong crossflow motions. A gap (28) may be narrow in the helical spine perhaps located at the top position of the tubing component perhaps to enable gases to flow along the pipe. Gases may naturally rise to the top of the pipe.

Gaps may also be put into the spirals at the bottoms of the tubing components for the purposes of drainage of the bioreactor tubing components.

Embodiments of the present invention may allow for the passage of substrates in the form of balls, irregular compact shapes, or disc shaped substrates, that microorganisms, such as the bacteria *Actinobacillus succinogenes*, may grow on as they flow on down the tube mixing with $CO_2$ and sugars and nutrients. Such bacteria may grow heterotrophically. In these designs the gaps in the helical spine may be designed to enable their passage with the greatest ease. The helical spine may have more and wider gaps, because the tube bioreactor may use the additional mixing that the irregular motions of the substrate materials creates.

Figure 16:
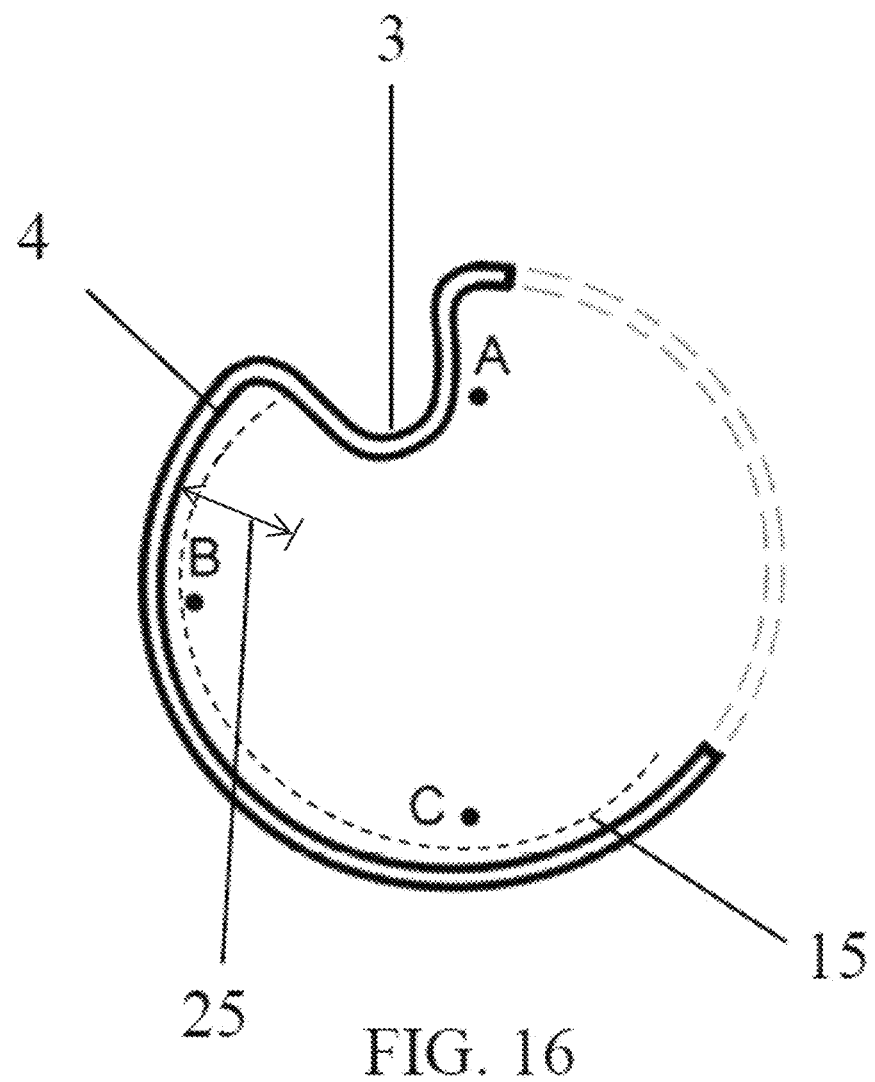
FIG. 16 shows a cross-section end view of FIG. 17 where A, B, and C may be fluid particle paths associated with A, B, and C of FIG. 17 in accordance with some embodiments of the present invention.

Embodiments of the present invention may provide positioning an inwardly protruding helical spine (3) so that it may protrude into a fluid flow at a distance (25) from an inside surface (4) of a tubing component that puts the protrusions beyond a predominantly viscosity governed flow field (15) as may be understood from FIG. 16. A predominantly viscosity governed flow field (15) may be a viscous sublayer. A height of a sublayer may depend on the speed of the flow in a pipe. The higher the flow speed, the thinner the sublayer may be. It may be desirable to provide a low speed perhaps to provide a low energy system and thus a sublayer may be at its widest or perhaps even close to a thickest possible layer. This may be ¹⁄₂₀ of a radius of a tubing component. In turbulent pipe and duct flows, the region close to the walls may be governed by viscosity. In a pipe flow, for example, this viscous governed region may be called the viscous sublayer and its thickness (e.g., a region of viscosity's influence) may depend on a Reynold number of the flow (which may change with the speed of flow in any given pipe) and may depend less so on pressure gradient. As the Reynolds number may decrease, the viscous layer may increase in thickness, but it may not be greater than about ¹⁄₂₀ of the radius of the pipe, if the flow remains naturally turbulent. In this region, the viscosity may dominate. The viscous sublayer may not have a well-defined boundary and even at this estimate, there may be some viscous influence perhaps for another about ¹⁄₂₀ of a radius, but inertial forces may be getting stronger and stronger as we move further away from the wall. For a flow to behave as shown by particle paths in FIG. 17, it may not be dominated by viscosity. Thus, a protruding helical spine may have amplitudes that may be greater than or even significantly greater than a viscous layer. Therefore, any "decorative" impressions that may be made as "designs" into the surface of a tubing component may not have a desired effect. If a spine protrusion was buried in a viscous governed region, it may not result in flow separations and achieve desired cross-flows. Such flow could largely go over a spine, back down to the wall, and may continue along the wall, or may even locally separate and form a closed recirculating region immediately behind the spiral, again it may not create the needed cross-flows. It may be the inviscid reaction (e.g., the behavior of a fluid where viscosity may not be important) to a protruding helical spine that may be desired. Because we desired that the flow may be run at the lowest possible Reynolds number (e.g., lowest possible speed) where this effect can be maintained, perhaps so as to use the minimum energy to drive the flow (e.g., and thus making the processes most economical), the viscous sublayer may grow thick. At higher speeds, the viscous sublayer may be thinner and thus the height of the protrusion can be made smaller, but needs to be large enough to protrude out of a viscous region. However, at higher Reynolds numbers, although the economics for a given pipe mass flow rate may be undesirable, these smaller spiral intrusions could be used in some embodiments of the present invention. Therefore, the distance (25) of a protrusion may vary depending on the details of the system. Protrusions of a helical spine may generally make up portions of a spiral that may have a boundary contained within a spiraling locus of a path.

Embodiments of the present invention may provide a system that may be configured to produce fluid dynamic effects. For example, an inwardly protruding helical spine, or other flow modifier or the like, may provide, but is not limited to local unsteady separation of said fluid flow; local adverse pressure gradients in said fluid flow; unsteady, low shear stress, stagnation lines in said fluid flow; unsteady, unstable, short lived separation bubbles unevenly distributed along the helical spine in said tubing component resulting in strong cross-flows; continuous unsteady separation of a fluid containing microorganisms from an inwardly protruding helical spine in a fluid flow all along a tubing component; any combination thereof; or the like as may be discussed herein.

As discussed herein and as suggested by FIGS. 6-10, there may be a problem with microorganism sticking to an inside wall of a tubing component. Thus, the present invention, in some embodiments, may prevent microorganisms from sticking to an inside of a tubing component perhaps with a fluid flow coordinator, a passive microorganism flow modifier, an inwardly protruding helical spine, an outwardly protruding helical spine, or the like. In embodiments of the present invention, it may provide that an inwardly protruding helical spine may not use any moving parts, mechanical motions, or even moving mechanical parts perhaps that are associated with a mixing process.

The present invention, in some embodiments may provide scaling of a helical spine, fluid flow coordinator, passive microorganism flow modifier, or the like perhaps to provide a scaled helical spine, scaled fluid flow coordinator, a scaled passive microorganism flow-modifier, or the like. FIGS. 32-36 show various examples of an inwardly protruding helical spine (3) and a few representative samples of how it may be scaled to provide a scaled inwardly protruding helical spine (33). Scaling may provide changes to any one of or any combination of changes or even customizing of a pitch (34), width (35), depth (36), or the like of an inwardly protruding helical spine. This may provide a customized pitch, a customized width, a customized depth, or the like of a helical spine. A depth, width, or even a pitch may be proportional to a main bounding duct scale (e.g., a diameter of pipe, a channel width, if a channel, co-axial gap if coaxial pipe, or the like), and may be proportional to velocity of the mean fluid flow in the ducts. A scaled inwardly protruding helical spine may be customized so that it may be tailored to a specific type of microorganism used in a bioreactor system. A customized depth, customized width, customized cross-sectional profile, or even a customized pitch of a scaled inwardly protruding helical spine may be tailored to a specific tubing component's scale (e.g., a pipe's diameter) or may even be tailored to a specific velocity of a mean flow used in a bioreactor system.

A scaled inwardly protruding helical spine may be scaled perhaps by a scaling element which may include but is not limited to changing a pitch of a scaled inwardly protruding helical spine; changing a width of a scaled inwardly protruding helical spine; changing a height of a scaled inwardly protruding helical spine; changing the cross-sectional shape of a scaled inwardly protruding helical spine, changing the number of scaled inwardly protruding helical spines; changing the position of a scaled inwardly protruding helical spine; optimizing a scaled inwardly protruding helical spine perhaps to promote better movement of microorganisms within a tubing component; optimizing a scaled inwardly protruding helical spine perhaps to promote better movement of microorganisms to interact with light and dark areas within a tubing component; optimizing a scaled inwardly protruding helical spine perhaps to promote better movement of microorganisms to interact with nutrients within a tubing component; and perhaps even optimizing a scaled inwardly protruding helical spine perhaps to promote better movement of microorganisms to interact with gases within a tubing component, or the like.

Figure 32:
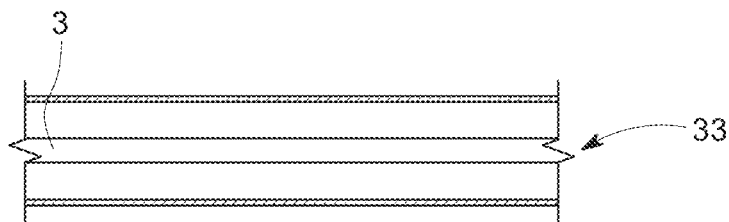
FIG. 32 shows an example of a scaled inwardly protruding helical spine in accordance with some embodiments of the present invention.
Figure 33:
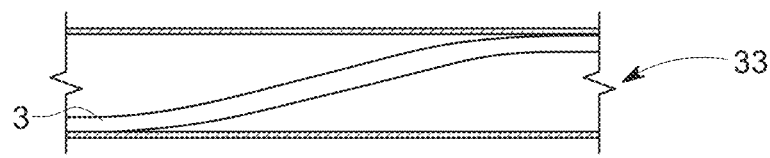
FIG. 33 shows an example of a scaled inwardly protruding helical spine in accordance with some embodiments of the present invention.
Figure 34:
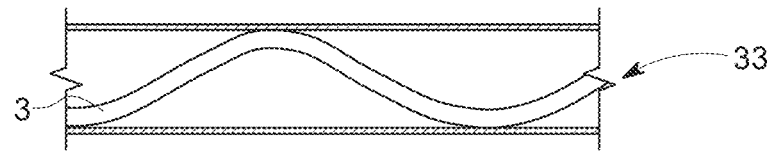
FIG. 34 shows an example of a scaled inwardly protruding helical spine in accordance with some embodiments of the present invention.
Figure 35:
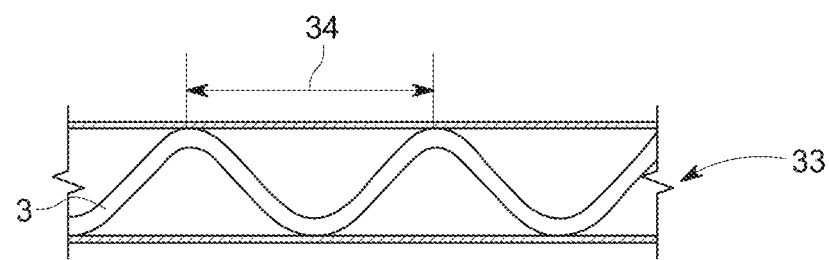
FIG. 35 shows an example of a scaled inwardly protruding helical spine in accordance with some embodiments of the present invention.
Figure 36:
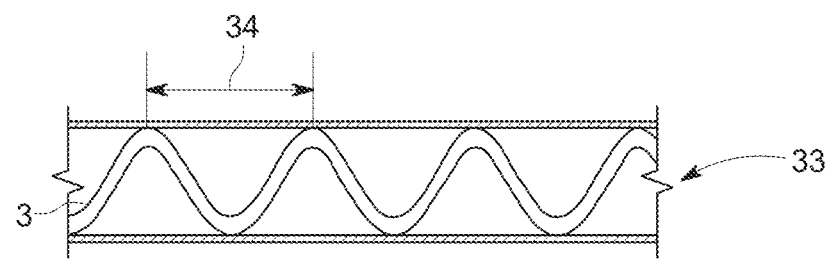
FIG. 36 shows an example of a scaled inwardly protruding helical spine in accordance with some embodiments of the present invention.
Figure 37:
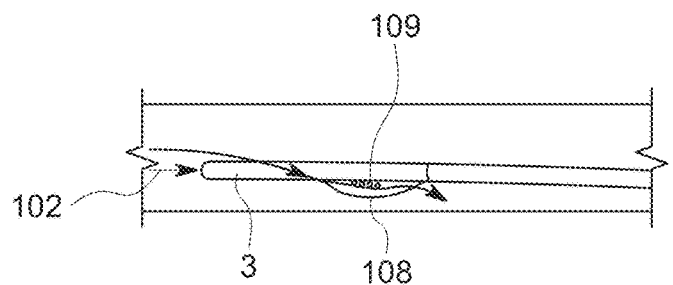
FIG. 37 shows an example of an inwardly protruding helical spine with a fluid flow in accordance with some embodiments of the present invention.
Figure 38:
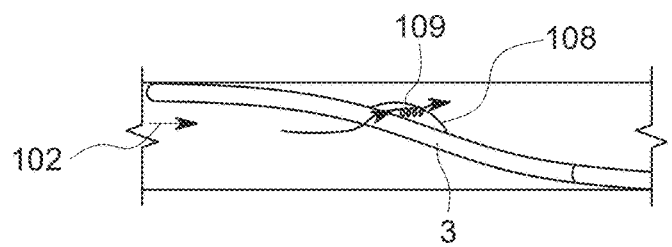
FIG. 38 shows an example of an inwardly protruding helical spine with a fluid flow in accordance with some embodiments of the present invention.
Figure 39:
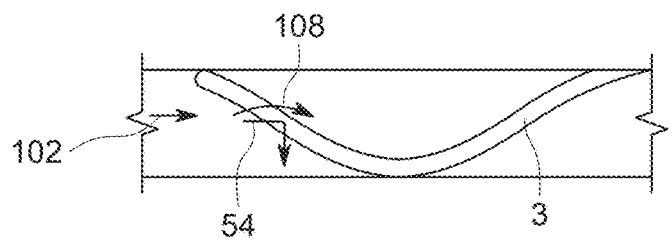
FIG. 39 shows an example of an inwardly protruding helical spine with a fluid flow in accordance with some embodiments of the present invention.
Figure 40:
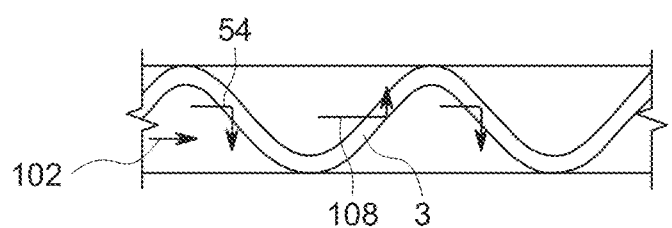
FIG. 40 shows an example of an inwardly protruding helical spine with a fluid flow in accordance with some embodiments of the present invention.
Figure 41:
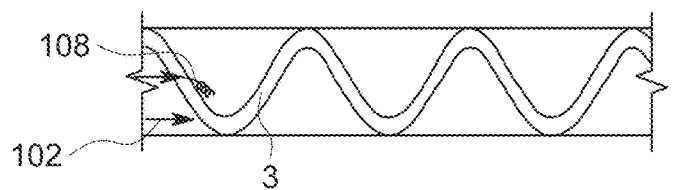
FIG. 41 shows an example of an inwardly protruding helical spine with a fluid flow in accordance with some embodiments of the present invention.
Figure 47:
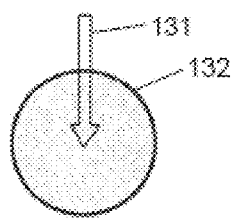
FIG. 47 shows an example of a light zone penetration vs. the stochastically uniform algae growth in accordance with some embodiments of the present invention.
Figure 48:
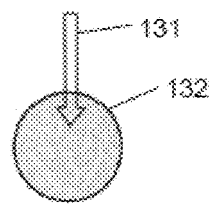
FIG. 48 shows an example of a light zone penetration vs. the stochastically uniform algae growth in accordance with some embodiments of the present invention.
Figure 49:
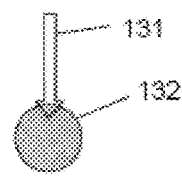
FIG. 49 shows an example of a light zone penetration vs. the stochastically uniform algae growth in accordance with some embodiments of the present invention.
Figure 50:
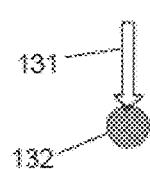
FIG. 50 shows an example of a light zone penetration vs. the stochastically uniform algae growth in accordance with some embodiments of the present invention.

FIG. 32 shows a spine that may be almost straight. Each of FIGS. 33 through 36 have changes to show how a pitch may be varied perhaps based on the needs of a particular system. A pitch (34) of a spiral may be a distance between each revolution of a spiral as may be understood in FIGS. 35 and 36. A width may be a distance across a spine such as may be understood in FIG. 18 and a depth may be the distance of a spine measured from an exterior a tubing component to perhaps the end of a protrusion of a spine as may be understood in FIG. 19.

As may be understood from FIGS. 37-41, fluid flow may vary with different pitches of an inwardly protruding helical spine (3) that protrudes out of the viscosity dominated layer as discussed above. A pitch may be a function of the speed of the fluid flow and perhaps even a diameter of tubing component. Because flow separation may be Reynolds number independent, the angle of incidence of the mean flow may play a large role. This angle could be such that over a range of mean speeds, the inwardly protruding helical spine may be able to create unsteady flow separation. Each of FIGS. 37-41 show examples of approximate flow fields (108) from a fluid flow (102) expected from inwardly protruding helical spines (3) at different pitches or wavelengths. A range of pitches or wavelengths of the inwardly protruding helical spine may be available to produce the desired cross flows.

FIG. 37 shows an example of a long wavelength spiraling obstruction of an inwardly protruding helical spine. It may indicate that local separation bubbles may occur at some locations and that these may remain attached to an inwardly protruding helical spine (3) perhaps with internal corkscrewing particle paths (109) in these attached separation bubbles. FIG. 38 shows an example of a shorter wavelength spiraling and it may again indicate that local attached separation bubbles may occur at various locations perhaps that have corkscrewing particle paths (109) or even internal vortices corkscrewing in them. FIGS. 37 and 38 provide examples of wavelengths that may not create desired cross flows. There may be a range of wavelengths that may not create these desired cross flows.

FIG. 39 shows an example of a shorter wavelength spiral intrusion than the inwardly protruding helical spine (3) of FIG. 38. This may provide a sufficiently 'bluff' body to the oncoming flow (102) so that the flow fields (108) approaching may not remain attached, or that may not reattach to the inwardly protruding helical spine, and thus may separate into separated flows (54) from the inwardly protruding helical spine (3), and may go across the flow. This may be a desired effect. FIG. 40 shows an example an even shorter wavelength of an inwardly protruding helical spine than of FIG. 39. This also may cause an oncoming flow (102) to separate into separate flows (54) and may go across the flow as shown in the flow fields (108). Again, this is may be a desired effect. Thus, there may be a range of spiraling intrusion wavelengths that may accomplish desired cross flows.

FIG. 41 shows an example of when a wavelength of inwardly protruding helical spine (3) may be too short. A fluid flow (102) may form that has corkscrewing particle paths (109) perhaps with attached separation bubbles on the downstream side of the helical spine. The bubbles may remain attached and may not provide the desired cross flows. Overall there may be a range of wavelengths that can create the desired cross flows which may be optimized perhaps for a specific case of pipe diameter, flow speed, spiral width, spiral depth, or the like.

Embodiments of the present invention may provide various configurations of tubing components including but not limited to inclined (63), single linear section, wherein a tubing component may turn back on itself again and again (65), a tubing component may line a periphery of an inside of a building, loop, cylindrical duct; a closed and winding loop, any combination thereof, or the like. Tubing components may be mounted in a position including but not limited to vertically, horizontally, sloped, angled, any combination thereof perhaps providing a method for vertically mounting a tubing component, horizontally mounting a tubing component, mounting a tubing component at a slope, mounting a tubing component at an angle, any combination thereof, or the like. A tubing component, perhaps as a single linear section, could run along a downhill grade perhaps using only gravity to drive it from a coal plant, for example, to an algae biomass processing plant.

A tubing component may have a diameter including, but not limited to, about 6 inches, about 8 inches, about 12 inches, about 16 inches, about 24 inches, about 36 inches, about 42 inches, up to about 60 inches, less than about 0.5 inches, about 0.5 inches, about 1 inch, about 2 inches, about 3 inches, about 4 inches, about 5 inches in diameter, or the like. Both larger and smaller sizes of a tubing diameter could be used. For drugs (e.g., penicillin, antibiotics, or the like) perhaps about 6 inches and even smaller sizes may be appropriate. For capturing $CO_2$ perhaps from industrial chimneys, tubing sizes may need to be larger where fluid dynamically it can be scaled up to a needed size perhaps without losing its mixing component. An important purpose of embodiments of the present invention may be to handle large mass flows of $CO_2$ from coal and natural gas power plants, and even cement factories, or the like where about 24 inch and larger diameter pipes may be used. Optimal mixing that may be produced in the various embodiments as discussed herein may be achieved on all scales, perhaps from the smallest scales to the largest allowed by a pipe diameter. A system's grade can be related to a diameter of a tubing component, a speed of the flow in a tubing component, the type of microorganisms, and perhaps even the gases that may need to be expelled. Embodiments of the present invention may provide that the amount of fluid added to fill a fluid component's area may be as much as possible perhaps so that the forcing effect of the flow modifiers, for example, the spiraling, may be applied to as much of the fluid flow as possible.

FIGS. 46-50 show a system modification perhaps for certain microorganisms (for example, certain algae) that can grow to be very dense and perhaps under conditions of prescribed light/dark ratios. Algae can require very different growth conditions, particularly the time in light and the time in dark regions. FIG. 46 provides a contracted tubing (67) with perhaps multiple area-contractions (68) in the tubing. It may start (133) at a wider diameter and may end (135) at a smaller diameter. Contraction of a tubing component may be reduced in diameter, may be narrowed, may be tapered, or the like. In this example, as a diameter of a tubing component may decrease, a flow speed may increase, perhaps so the cross-flow speeds which may bring the algae to the light at the walls may also increase. These area changes can be setup perhaps to keep light/dark ratios constant or may even increase a light/dark ratio perhaps as a mixture may become more dense (e.g., as it goes downstream in the pipe). These figures are showing an example of a system modification that may compensate for an increasing density of a mixture. Microorganism growth density (132) is represented by shading in FIG. 46. FIGS. 47 to 50 provide examples of the stochastically uniform cross-sectional densities at certain stations of FIG. 46 under optimal mixing due to the various embodiments of the present invention, nominally showing the decreasing penetration of a light zone (131) that may occur as the density of microorganisms increases in a tubing component. In some embodiments, this may be an ideal density of algae with light penetration under optimal mixing due to the various embodiments of the present invention. With optimal mixing from the various embodiments of the present invention as discussed herein, a microorganism growth density may be stochastically uniform across each of these cross-sections even though a growth density may increase as they grow further down a tubing component. FIG. 47 shows an example of light zone penetration (131) at ~100% where the microorganism growth density (132) may be minimal. FIG. 48 shows an example of reduced light zone penetration (131) where the microorganism growth density (132) may be more than in FIG. 47. The density of the microorganisms is shown to remain uniform across the pipe at this station because of the optimal mixing from the various embodiments of the present invention. FIG. 49 shows an example of light zone penetration (131) to half again where the microorganism growth density (132) may be more than FIG. 48. The density of the microorganisms is again shown to remain uniform across the pipe at this station because of the optimal mixing from the various embodiments of the present invention. FIG. 50 shows an example of light zone penetration (131) that is just minimally into the mixture, where the microorganism growth density (132) may be more than FIG. 49. Again, the density of the microorganisms is again shown to remain uniform across the pipe at this station because of the optimal mixing from the various embodiments of the present invention. Notably, because the optimal mixing brings the microorganisms to the light at the pipe walls, and then takes them away from the walls, enabling other microorganisms to get to the walls and the light. Remarkably, as the microorganism growth density (132) increases, it can remain stochastically uniform with optimal mixing as described herein.

Figure 46:
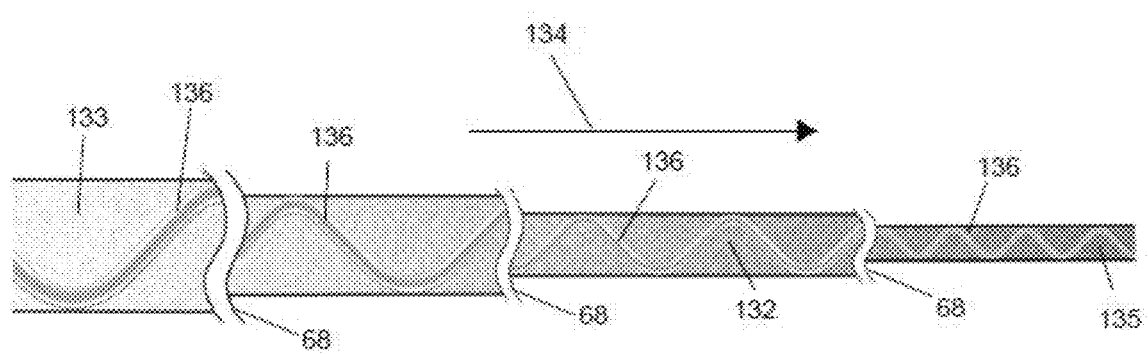
FIG. 46 shows an example of a contracted tubing in accordance with some embodiments of the present invention.

Embodiments of the present invention may provide contracted tubing that may have an inwardly protruding helical spine with an adjusted spiral width, pitch, shape, or the like perhaps based on a change in flow speed and even a tubing diameter as a non-limiting example, FIG. 46 provides a depiction of a changes that can be made to a helical spine (136) such as by changing its amplitude and even pitch as a tubing component's diameter may decrease, perhaps to keep a ratio of the helical spine in the optimal zone of amplitude and pitch.

Figure 51:
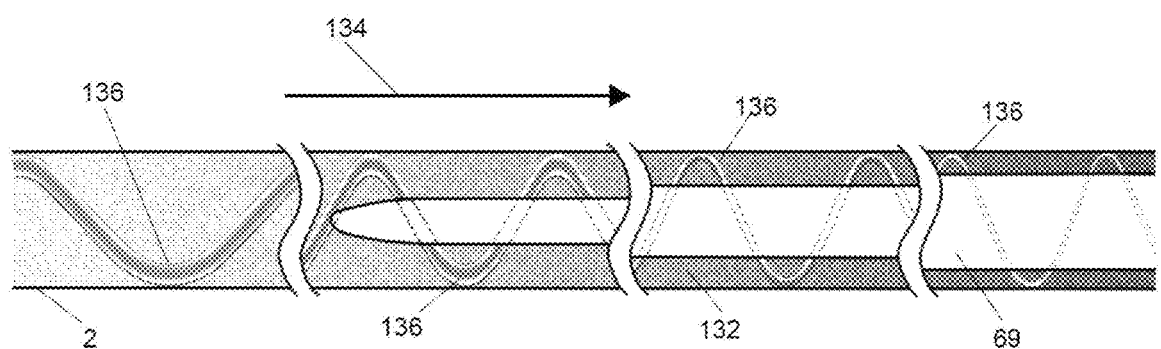
FIG. 51 shows an example of an inside tubing component in accordance with some embodiments of the present invention.
Figure 52:
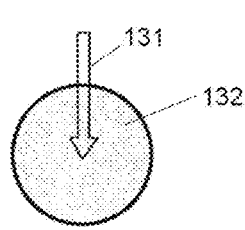
FIG. 52 shows an example of a light zone penetration in accordance with some embodiments of the present invention.
Figure 53:
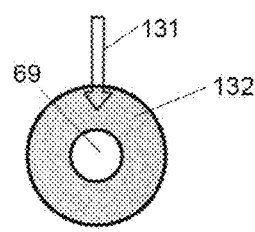
FIG. 53 shows an example of a light zone penetration in accordance with some embodiments of the present invention.
Figure 54:
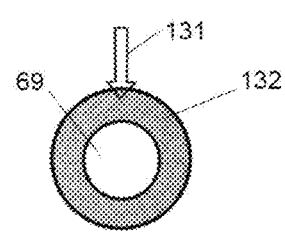
FIG. 54 shows an example of a light zone penetration in accordance with some embodiments of the present invention.
Figure 55:
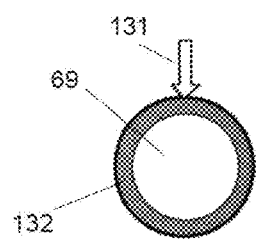
FIG. 55 shows an example of a light zone penetration in accordance with some embodiments of the present invention.

FIGS. 51-55 provide an example of an embodiment of the present invention to perhaps address many of the same concerns as provided in the discussion of FIGS. 46-50. FIG. 51 shows an example of tubing component (2) which may have a constant diameter and an inside tubing component (69) may be inserted into the outer tubing. An inside tubing component may be a coaxial body tubing or the like. This approach may allow more light to the algae perhaps because the insert can be lighted. Some microorganisms can grow faster with the additional light. An inside tubing component may need some supporting (e.g., centering) pieces. To keep the ratio of the helical spine in the optimal zone of amplitude and pitch, FIG. 51 depicts an example of a changes that can be made to a helical spine (136) perhaps where its amplitude and even pitch may decrease as a tubing component's annular space may decrease. FIGS. 52-55 provide examples densities of a microorganism mixture that may be stochastically constant across the cross-sections at certain sections of FIG. 51. An inside tubing component (69) can be configured to enable the light zone to perhaps extend all across the annulus, perhaps even as the density of the mixture may become very high. But at a minimum, it can also provide more area of illuminated wall, so that the optimal mixing from the various embodiments of the present invention have more illuminated walls to bring the algae to. FIG. 52 shows an example of light zone penetration (131) at ~100% where the microorganism growth density (132) may be minimal. FIG. 53. shows an example of reduced light zone penetration 53 (131) where the microorganism growth density (132) may be more than in FIG. 52. The density of the microorganisms is shown to remain stochastically uniform across the pipe at this station because of the optimal mixing from the various embodiments of the present invention. FIG. 54 shows an example of light zone penetration (131) at 60% where the microorganism growth density (132) may be more than FIG. 53. Again, the density of the microorganisms is ideally shown to remain stochastically uniform across the pipe at this station because of the optimal mixing from the various embodiments of the present invention. FIG. 55 shows an example of light zone penetration (131) that extends just minimally into the mixture, where the microorganism growth density (132) may be more than FIG. 54. Notably, because the optimal mixing brings the microorganisms to the light at the pipe walls (possibly both the outside and inside walls of the annulus), and then moves the microorganisms into the interior of the annulus, again the density of the microorganisms is shown to remain stochastically uniform across the annulus of the pipe. Remarkably, as the microorganism growth density (132) increases, it can remain stochastically uniform with optimal mixing.

Figure 56:
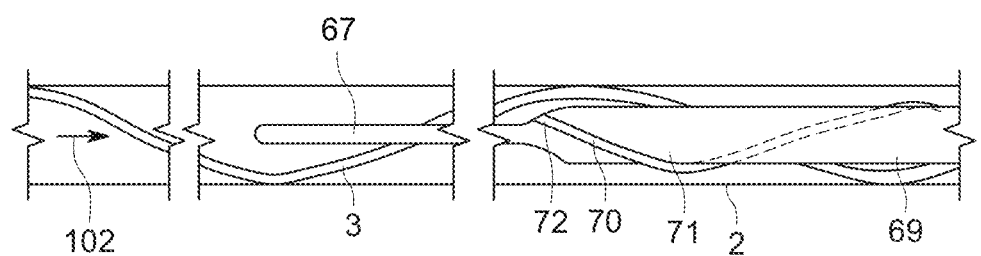
FIG. 56 shows an example of an inside tubing with an outwardly protruding helical spine in a tubing component in accordance with some embodiments of the present invention.
Figure 57:
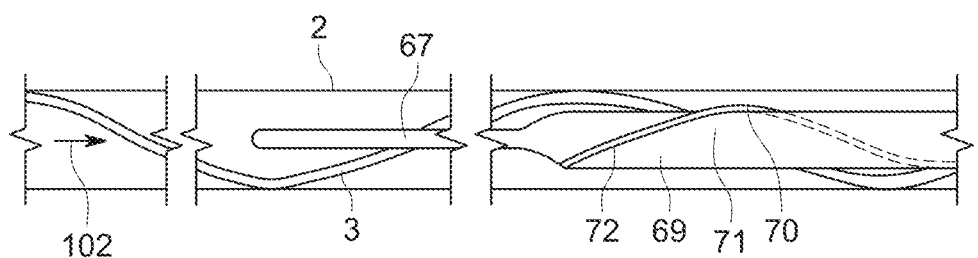
FIG. 57 shows an example of an inside tubing with an outwardly protruding helical spine in a tubing component in accordance with some embodiments of the present invention.
Figure 58:
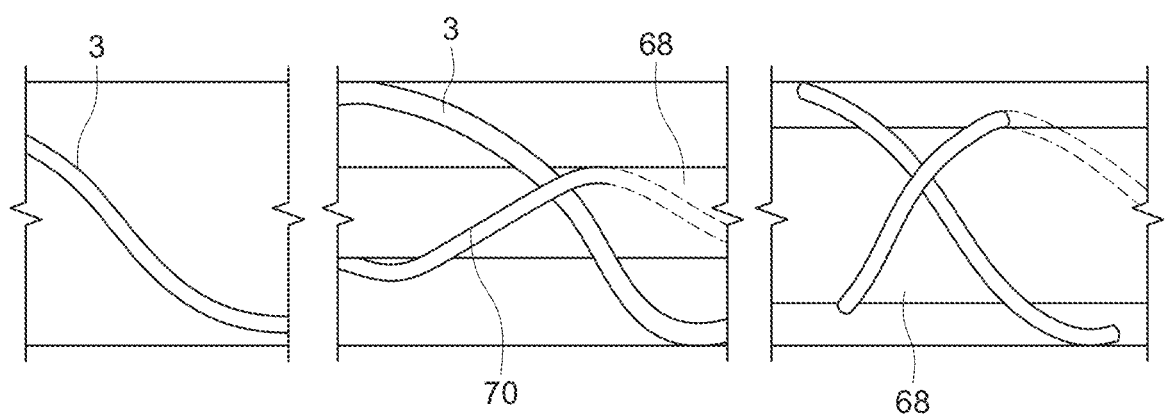
FIG. 58 shows an example of an inside tubing with an outwardly protruding helical spine in a tubing component in accordance with some embodiments of the present invention.

FIGS. 56 and 57 provide two example configurations which may further shorten an optical path that algae may have to convect through perhaps to get to a photic zone which may be emanating from any of the walls of a tubing component. In some embodiments, the present invention may introduce light into a mixture perhaps through an inside tubing component (69) which may be a center pipe, a coaxial body tubing, or the like. An inside tubing component may be a contracted tubing (67). This may reduce, or even significantly reduce, the travel length of the microorganisms to photic zones. Mixing of the fluid components may be enhanced with an outwardly protruding helical spine (70) perhaps located on an outside surface (71) of an inside tubing component. An inside tubing component (69) may reduce the cross-sectional area of the tubing component which may result in a fluid mixture flowing faster in this region, and thus, resulting in faster cross-flows. In some embodiments, this may obviate the need to clean this region. In other embodiments, use of an inside tubing component may necessitate a longer run of the tubing component or may even need additional recirculation cycles. FIG. 56 shows a spiral twist (72) of an outwardly protruding helical spine (70) on an outside surface (71) of an inside tubing component (69) which may be winding in an opposite direction as a spiral of an inwardly protruding helical spine (3) on an inside surface of a tubing component (2). FIG. 57 shows a spiral twist (72) of an outwardly protruding helical spine (70) on an outside surface (71) of an inside tubing component (69) which is winding in a same direction as a spiral of an inwardly protruding helical spine (3) on an inside surface of a tubing component (2). The direction of a twist (72) of a helical spine may vary. Furthermore, the pitch and amplitude of the spiral component on the inner tubing component may be the same, or different from the pitch and amplitude of the helical spiral protruding into the flow from the outer tubing component. FIG. 58 shows an example of a tubing component having an inwardly protruding helical spine (3) on an inside surface of a tubing component with an inside tubing component having an outwardly protruding helical spine (70) on an outside surface of an inside tubing component. The tubing component may have multiple area-contractions (68), multiple spiral sizes and multiple spiral pitches, as may be understood from FIG. 58.

Figure 59:
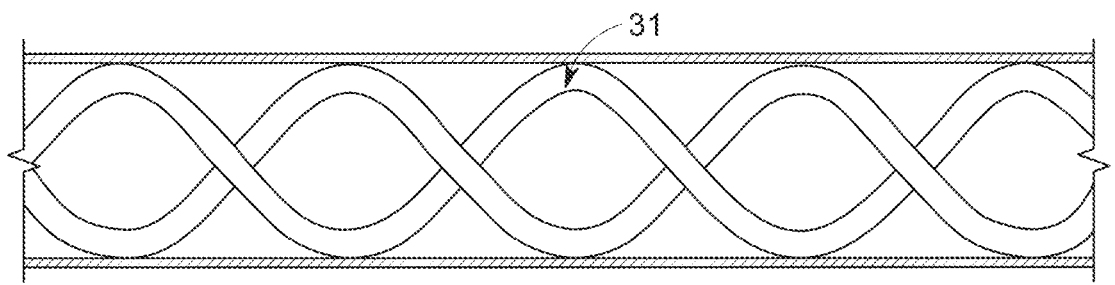
FIG. 59 shows an example of a double helix in accordance with some embodiments of the present invention.
Figure 60:
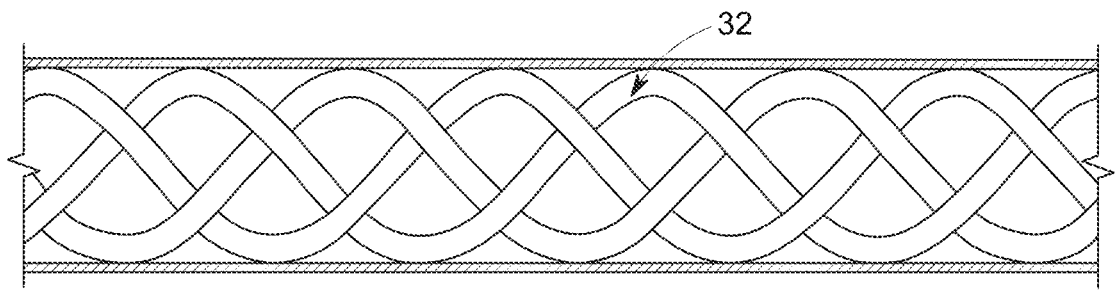
FIG. 60 shows an example of a triple helix in accordance with some embodiments of the present invention.

A protruding helical spine may have any kind of shape including but not limited to rounded contours, circular cylinders, streamlined shapes, airfoil shapes, any combination thereof, or the like. A helical spine may be a multiple helical spine, may be a double helical spine, may be a triple helical spine, or the like. FIGS. 59 and 60 provide examples of multiple helical spines. FIG. 59 provides an example of a double helix (31) which may be used with an inwardly protruding helical spine or outwardly protruding helical spine or the like. A double helix may provide faster cross flows in some embodiments. FIG. 60 provides an example of a triple helix (32) which may be used with an inwardly protruding helical spine or outwardly protruding helical spine or the like. A triple helix may create higher perturbation intensity, and greater mixing in some flows.

Embodiments of the present invention may provide that an outwardly protruding helical spine and perhaps even an inwardly protruding helical spine have a customized depth, customized pitch, customized shape, customized direction of a twist, or the like as discussed herein. Perhaps for each area contraction resulting from a coaxial body placed inside, a spiral depth, pitch, shape and even direction of twist of either or both the inward and the outward protruding helical spines may be adjusted based on a flow speed and even size of a resulting annulus within a tubing. In some embodiments, an inwardly protruding helical spine may be an example of a passive microorganism flow modifier or even a fluid flow coordinator in that some systems may provide passively modifying a flow of fluid in a tubing component with an inwardly protruding helical spine or even a fluid flow coordinator. A fluid flow coordinator may be an example of a passive microorganism flow modifier.

Embodiments of the present invention may provide low shear stress to microorganisms as they may flow in a fluid throughout a tubing component. This may be accomplished with a fluid flow coordinator, a passive microorganism flow modifier, an inwardly protruding helical spine, or the like. Low shear stress may cause minimal damage to microorganisms. A low shear stress may include a shear stress magnitude that may be below a value that could cause destruction of the microorganisms. For example, if we are using an algae like *Spirulina*, which may be an extremely elongated twisting spiral algae, the shear stresses that may be needed to break it up may be quite low, whereas, for micron sized spherical algae, the shear stresses can be significantly higher before damage may be done to the algae. Of course, whether or not an algae has a tough cell wall is also important. Therefore, a desired level of low shear stress may vary depending on the detail of a system.

Figure 61:
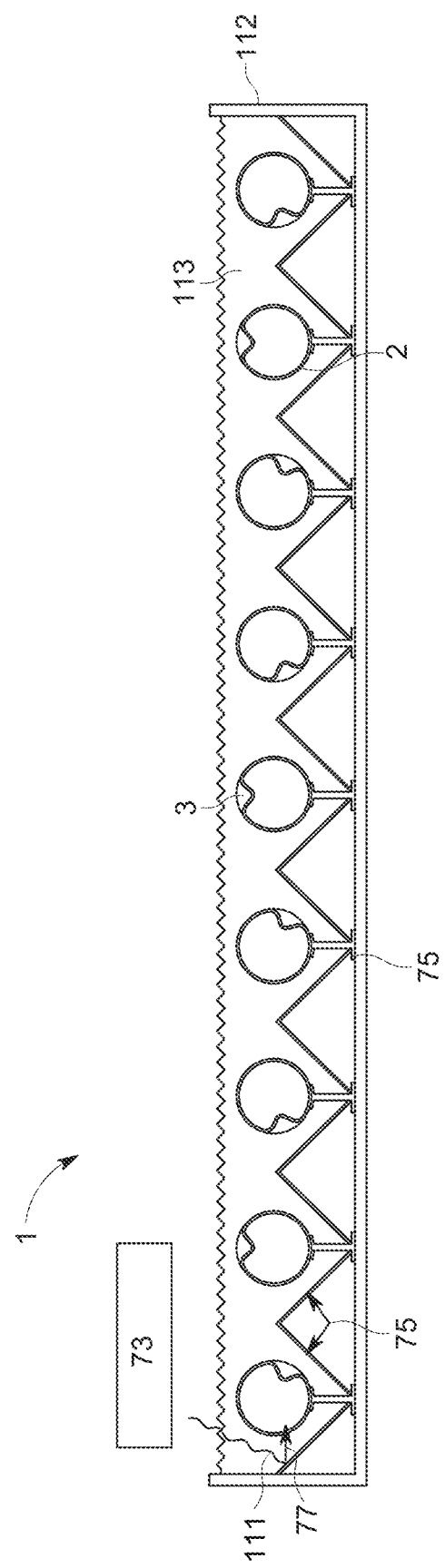
FIG. 61 shows an example layout for a bioreactor system in accordance with some embodiments of the present invention.

FIG. 61 provides an example of a layout for a bioreactor system that can utilize sunlight during the day, and can be artificially illuminated at night. It includes, but is not limited to, tubing components (2) having an inwardly protruding helical spine (3), at least one reflector (75) which may be a mirrored surface, located in a pool (112) filled with water (113), or the like. At least one reflector (75) may be located near a tubing component perhaps so that it may be positioned to reflect light from a lighting element onto a tubing component. A lighting element may be optimized to substantially expose a tubing element the light.

FIG. 61 may be an example of said bioreactor system design to control temperature via a water pool, and control light input via reflectors. The water temperature could, for example, use waste heat from a factory or power plant. This figure shows a cross-section of an example bioreactor system (1) with nine tubing components with reflectors (75) such as mirrored surfaces facing the tubing components. Reflectors (75) may also be provided in the lower rounds of the figure. A lighting element (73), such as the sun, may emit rays (111) of light which may be reflected by the reflectors onto the tubing components so that the microorganisms therein can absorb the light over a large portion of the tubing component's circumference. This system may be placed in a greenhouse. If used outdoors, the addition of artificial lighting (perhaps via LEDs wrapped around each length of tubing component) can enable microalgae growth on cloudy days and at night. Of course, this is a non-limiting example of one embodiment of the present invention, and it may be varied in any way to accommodate a desired need.

Figure 65:
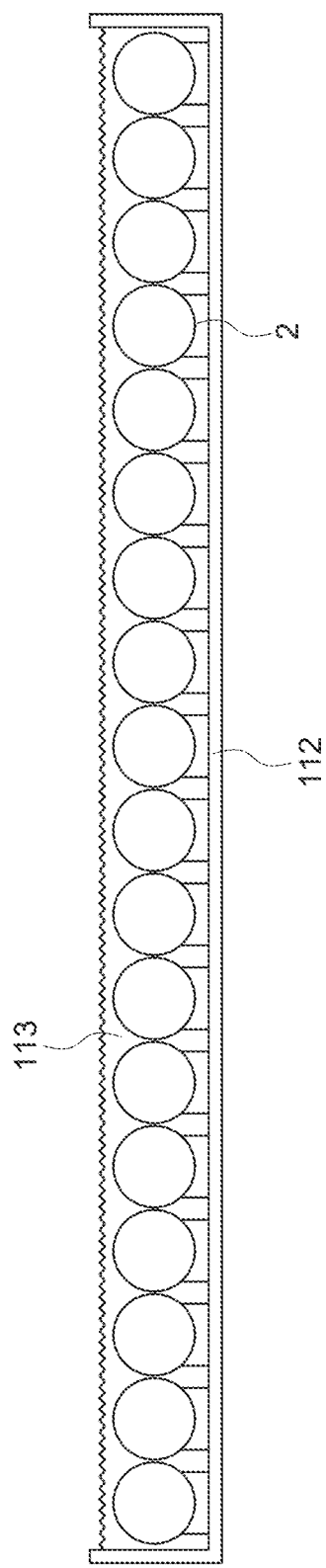
FIG. 65 shows an example layout for a bioreactor system in a pool in accordance with some embodiments of the present invention.

FIG. 65 is an example of a bioreactor system in a pool (112) of water (113) showing a cross section of the tubing components (2). In this example, designed to primarily use artificial lighting, perhaps LED strings wrapped around each tubing component (or perhaps placed at the intersections top and bottom perhaps with reflectors, we can achieve a more dense packing of the tubing components, thus producing more algae per acre. Of course, sunlight can also supplement the lighting, when available. In this example, eighteen tubing components may be utilized which may each be about two feet in diameter by about 135 feet in length. Some systems may use up to four pools or more, arranged as needed. Some non-limiting calculations for a facility may include, but is not limited to about 158 feet less about 1.6 feet=about 156.4 feet of free pond space divided by four ponds=about 39 feet per pond=about 469 inches wide. Each about 24-inch internal diameter pipe with about ¼ inch walls and about 1-inch band at the seams may take up about 25.5 inches. About 469 inches divided by about 25.5 inches=about 18.4 pipes rounded to about 18 pipes per pool. About 18 pipes multiplied by about 135 feet for a length of pool=about 2430 feet of pipe per pool, times about 23.5 gallons per foot=about 57,105 gallons per pool. Four pools times about 57,105 gallons=about 228,420 gallons (864,663 liters) for a facility. This could require about B acre. In one embodiment, smaller groups, of say 2-4 pipes, may be laid in a trench that circumscribes a power plant's boundary, and is temperature controlled by using waste warm water, for example.

FIG. 62 provides another example of a layout for a photobioreactor system where tubing component arrays may be placed facing south and may be adjusted for each location perhaps to maximize sun exposure. A lighting element (73), such as the sun, may emit rays (111) of light which may impinge directly on the tubing components, as well as be reflected by the reflectors onto the tubing components so that the microorganisms therein can be more uniformly illuminated. Reflectors (75) such as angled mirrors may be placed behind the tubing components perhaps to help optimize sunlight exposure on all sides. The arrows indicate the direction of flow when multiple rows of tubing may be required. Microorganisms, such as algae, perhaps located in a low position (114) may be pumped (116) to a top position (115) of an array of tubing components. Arrays such as these may be placed in greenhouses for temperature control, and may also be artificially lighted.

A lighting element (73) may be continuous lighting perhaps so that at least some of tubing component may be continuously exposed to light from a lighting element. A lighting element (73) may provide single wavelength, multiple wavelengths, may be sunlight, artificial light, laser light, constructed sheets of laser light, pulsed sheets of laser light, LED arrays, solid state laser light, solid state laser light distributed perhaps using diffusive fiber optics, sunlight distributed using diffusive fiber optics, light pipes, pulsed lighting element, any combination of thereof, or the like. Some embodiments of the present invention may provide a light adjuster, adjusting the light to a tubing component. This is a non-limiting example of one embodiment of the present invention and it may be varied in any way to accommodate a desired need.

Figure 64:
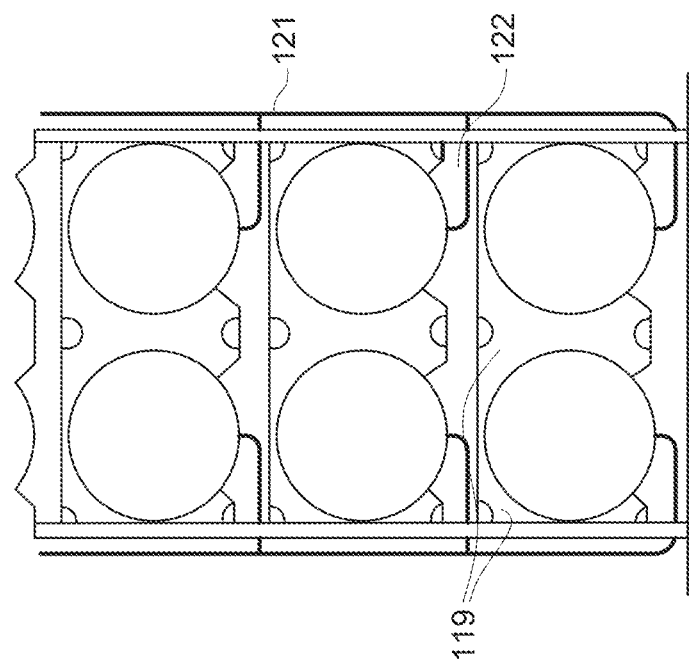
FIG. 64 shows an example layout for a bioreactor system using artificial lighting in accordance with some embodiments of the present invention.
Figure 63:
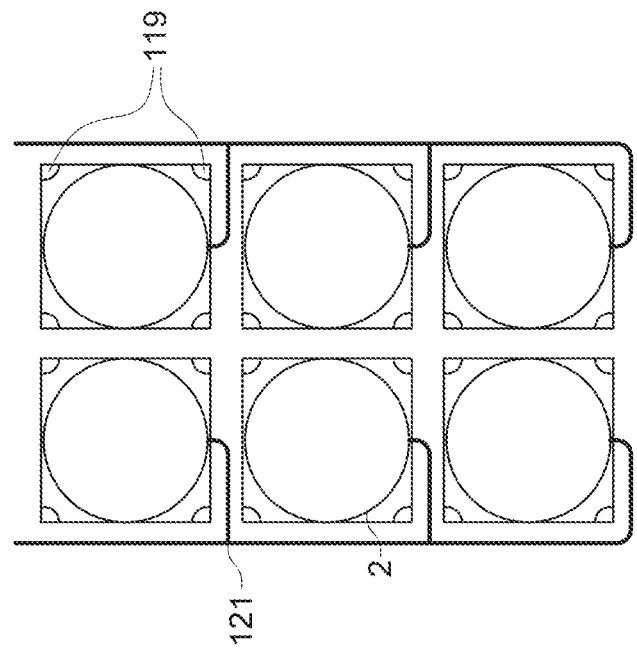
FIG. 63 shows an example layout for a bioreactor system using artificial lighting in accordance with some embodiments of the present invention.

FIG. 63 shows an example of a bioreactor tubing component (2) system that is close-packed, and designed to be in an enclosure. In this non-limiting example, artificial lighting (119) is applied which may consist of linear or area LED arrays perhaps either laid along the axis of the tubing components or perhaps wrapped around the tubing components. It shows piping (121) that may be used to remove or add gases such as carbon dioxide, oxygen, or the like. FIG. 64 is an example of a bioreactor system like FIG. 63 with an example of a support system. (122).

It may be an advantage of the present invention to operate the tubing components essentially full of the perhaps microorganism/water mixtures. This may enable the flow modifiers to have the greatest effect on the flow, because they are in contact with the fluid more of the fluid's flow time. This perhaps means that the flow modifiers can create the cross-flows in a larger volume of the fluid, and it means that there may be more illuminated pipe wall area available to have the cross-flows carry the algae to impart light on the algae. Furthermore, a full tubing component perhaps enables us to have the highest mass flows of microorganisms per tubing component volume. In some embodiments, all of the configurations, and others too numerous to detail, may have the tubing component at a slight grade. The angle of tubing component can be quite small, the order of say about 0.5 to about 3 degrees of slope depending on the overall circumstances, to accomplish this task.

Figure 66:
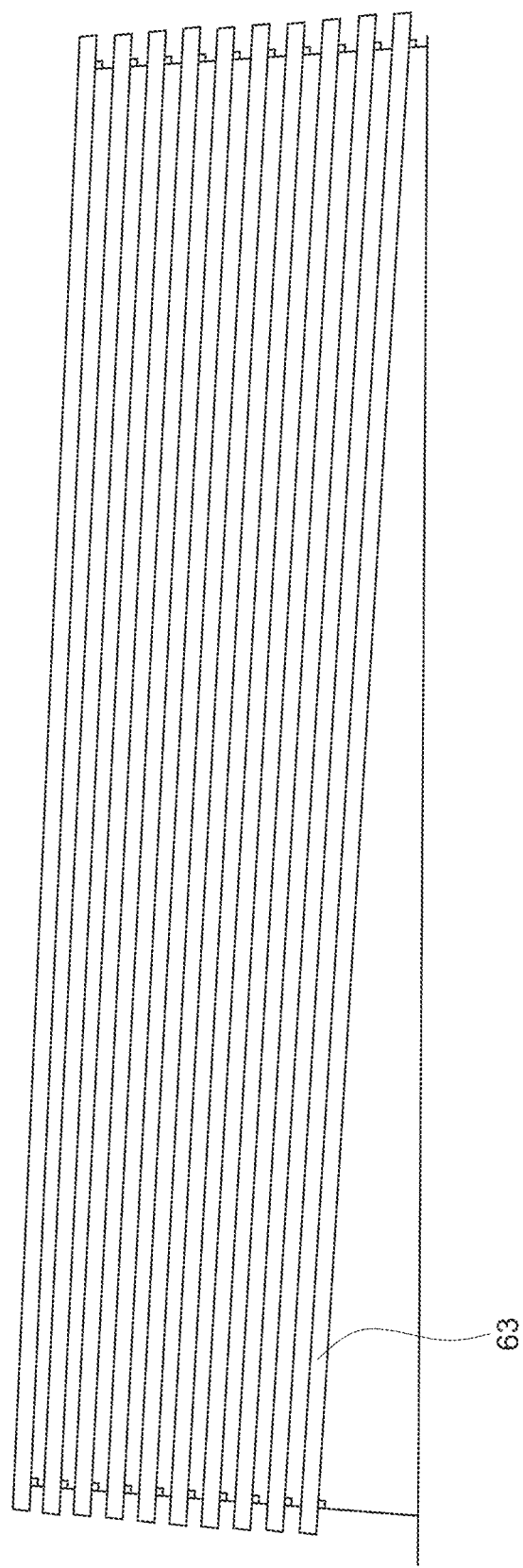
FIG. 66 shows an example of an inclined tubing component in accordance with some embodiments of the present invention.

FIG. 66 shows an example of an inclined tubing component (63) perhaps used in a sample grade layout. This shows a side view of a six inch by 5000 feet system at about 3% grade with 1⅝-inch strut. The gas passageways of FIGS. 44 and 45 (103) can be on the tops of each turn of the spirals of each of these tubes. For the purpose of gas transfer, adsorption and/or removal, the flow in such systems may be from the bottom to the top of the system. Because the mean flow velocity may be very low, perhaps on the order of about 1 to about 4 inches per second, for non-limiting examples, the pipe friction is very low and the pumping needs are low.

Figure 67:
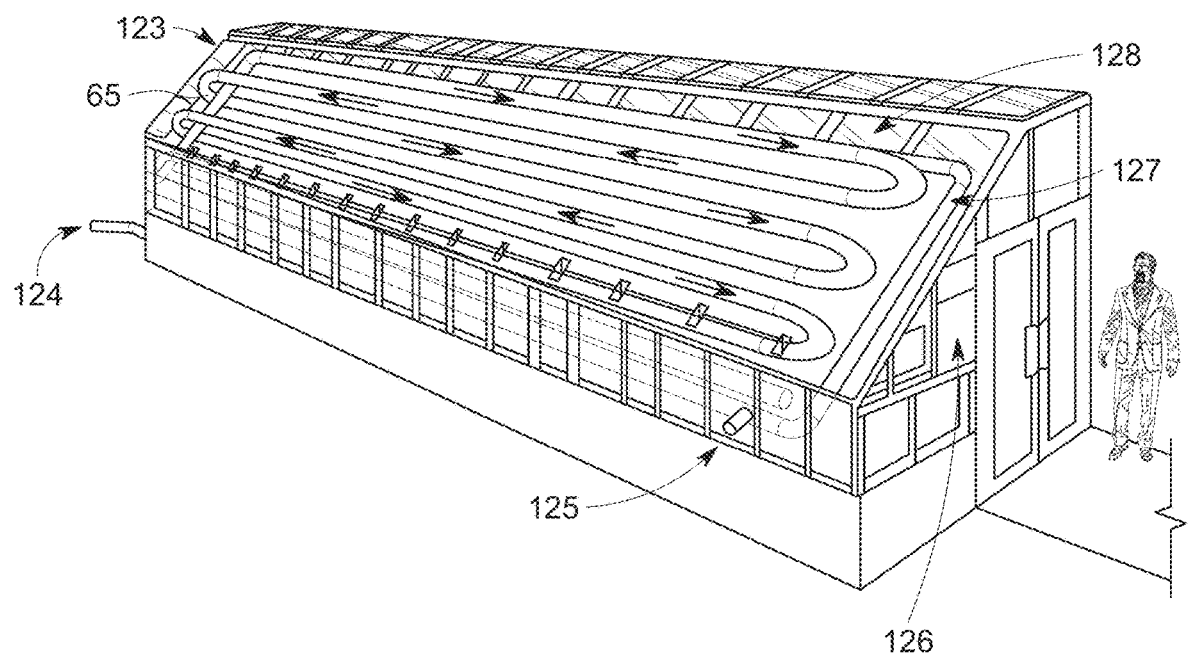
FIG. 67 shows an example of a bioreactor system in a greenhouse in accordance with some embodiments of the present invention.

In some embodiments, perhaps, but not limited to, the purpose of on sight demonstrations, or new biological scaling experiments, or flow engineering experiments, a greenhouse bioreactor system may be about 8 feet by about 28 feet. It may be built with 6" diameter tubing components, and thus may contain about ~1000 liters. It may also include reflectors, flow pumps, electrical components, monitoring equipment, $CO_2$ distribution piping, $O_2$ extraction piping, or the like (all not shown). As may be understood in FIG. 67, a system may include an input (123) where new inoculum may enter a system perhaps at a top valve and may circulate down through tubing components. Flue gas such as containing $CO_2$ may enter here (124) and may be distributed throughout a system perhaps with controlled pressure and valving. Microorganisms such as algae may be removed from tubing components at an exit (125) perhaps as new materials may enter a top. Pumps and monitoring equipment may be located behind (126) the tubing components. Flow recirculation (127) may be provided. It may provide distributed oxygen release valves (128). Lighting may be from the sun or artificial, or both. If from the sun, it can be positioned facing south, for example. Furthermore, it can be mounted on a flatbed trailer, and be transported. Once again sloping the tubing components (see FIG. 66), and the use of gas passageways (103), and may be directing mean flow in the direction of the buoyancy forces on the gases, will be employed. This may be an example of a closed, recirculating photobioreactor system.

Figure 68:
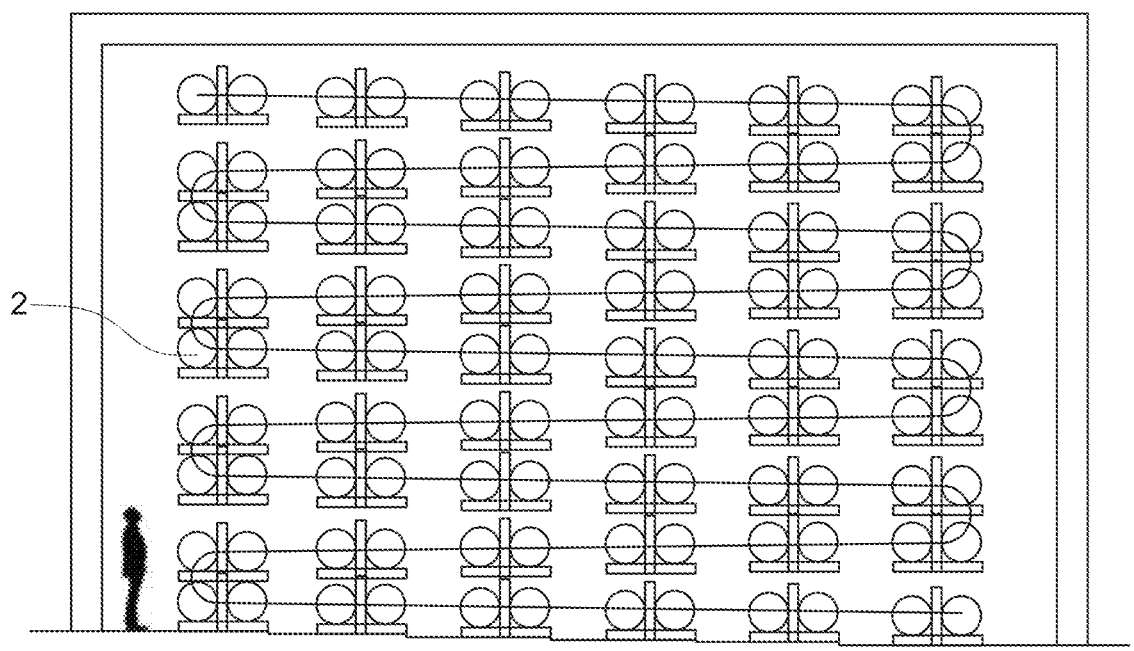
FIG. 68 shows an example of a large-scale bioreactor system in accordance with some embodiments of the present invention.

FIG. 68 shows an example of a large-scale bioreactor system which may utilize a building that may be about 35 feet tall by about 55 feet wide by about 85 feet long, as a non-limiting example. There may be about 108 tubing components (2) perhaps that are about 24 inches in diameter by about 75 feet long, e.g., about 8,100 feet of tubing. These may also embody a slope along the long axis of the tubing components (which is not shown in the drawing for sake of clarity), and the gas passageways. The continual overall slope is illustrated. The flow may be going upward, or may be going downward, depending on the overall needs of the system.

Figure 69:
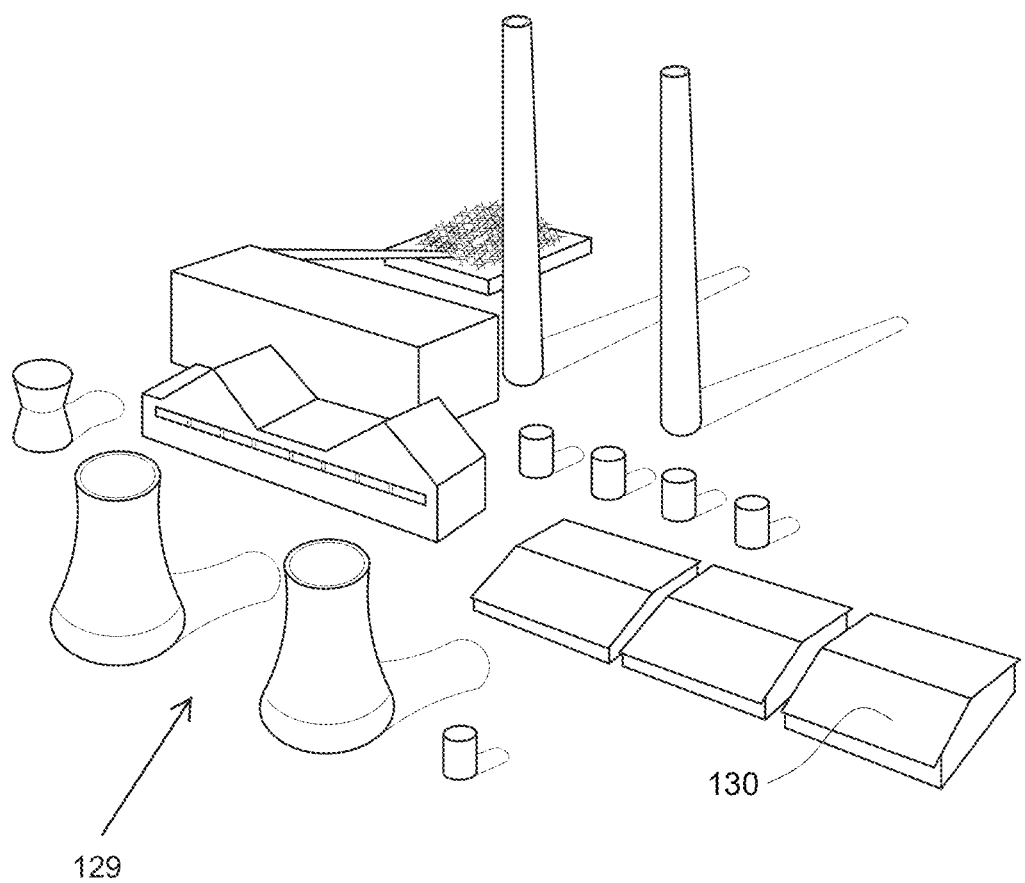
FIG. 69 shows an example of a bioreactor system with a power plant in accordance with some embodiments of the present invention.

FIG. 69 shows an example of a bioreactor system (130) used near a power plant (129). This system can perhaps be designed to be modular. Three buildings are represented, which together can under ideal conditions use probably use a few percent of the CO2 in the effluent of a supercritical several hundred MW plant. A possible course of development may embody the installation of one building of the size described above, have it pay back, enabling a fund to be built to add additional modules as indicated. In some cases, it may be desirable or possible to install many more modules depending on economic payback and regulations.

Embodiments of the present invention may provide a self-cleaning bioreactor system perhaps because of the scouring of the helical spine's induced cross-flows. Perhaps because of strong crossflows that may be created in embodiments of the present invention, cleaning of the walls of a tubing component of possible biofilm deposits may be done with little effort. The walls of a tubing component may be scoured every time algae may be taken away from the tubing component's wall by the crossflows, perhaps so that the total buildup of biofilms on the walls of these pipes may be significantly reduced. Because embodiments of the present invention may bring algae to the light perhaps by convecting the cells across the pipe to its walls, systems may use somewhat dirty or even cloudy water that may be the output of a wastewater treatment plant at different stages of treatment. Hence, we may successfully use available wastewater which may serve to supply nutrients, like nitrogen and phosphorus that algae require to grow (which are in the wastewater) and the algal growth may even provide a way to clean up the wastewater itself to varying degrees. Thus, a system may not have to incur an added expense of supplying nutrients like nitrogen and phosphorus into the water to grow the algae since it may already be present in the wastewater and this may as well reduce the expense of full wastewater treatment. If indicated, the flow mean flow speed can be temporarily increased, which will perhaps proportionally increase the tubing components cross-flow velocities, to enhance the scowering effect to the needed amount. A self-cleaning bioreactor system may provide that predators may be washed downstream (79). Embodiments of the present invention may provide a low maintenance system perhaps because a bioreactor system may be self-cleaning or may need minimal cleaning.

In embodiments of the present invention, they may provide a cleaner to clean a bioreactor system. A cleaner may be capable of flushing a tubing component with a cleaner fluid. A cleaner fluid may include but is not limited to water, hot water, steam, acidic fluid, basic fluid, any combination thereof, or the like. A cleaner may be a specially designed cleaner perhaps guided by an inwardly protruding helical spine and even pushed through a tubing component by mean downstream motions. This may be a pig element or other device that may be a sponge, that may be put into a fluid flow and may move downstream with a fluid flow, perhaps scouring the walls of the pipe to remove any biofilm that might develop on the pipe walls.

Embodiments of the present invention may provide treating a bioreactor system with an anti-fouling treatment. An anti-fouling treatment may include a polymerization of dopamine hydrochloride perhaps at an alkaline pH (e.g., H8502) which may to form a thin (perhaps up to about 50 nm) adherent polydopamine coating on an inside surface of a tubing component. Embodiments of the present invention may provide a low-cost construction system and may even provide a low energy input perhaps because it may operate at low speeds.

Embodiments of the present invention may produce GEMS perhaps by installing a spiraling impression of a specified amplitude, specified width, specific overall cross-section shape, and perhaps even a specified pitch into the walls of a pipe-type bioreactor that may be filled with the water/algae, or other water microorganism mixture. A spiral impression, a spiraling intrusion, a spiral perturbation, helical disturbance, or the like may be an inwardly protruding helical spine. An amplitude of the spiraling impression scales with the main pipe diameter, the width and cross-sectional shape may be a more complicated function of the type of algae, the flow speed, and perhaps even a shear the algae can withstand. A pitch of the spiral that scales on the main pipe diameter and flow velocity may be function of the amplitude of the spiral impression. Specified properly, a spiral impression may produce reoccurring, unsteady (perhaps in time and space) flow separations perhaps all along its length, and since the spiral impression may be made throughout the length of the pipe-type bioreactor, this type of flow may be created all along the length of the main pipe. Although the flow separations and the resulting cross-flows may all be different in magnitude and even direction from instant to instant, the geometry on the spiral impression may be responsible for the cross-flow energy at all length scales under region "A" of the spectrum in FIG. 5, perhaps as well as producing energy under the rest of the spectrum (region "B" as the net flow of energy may be to smaller scales). The generated large-scale motions may not individually spread out as indicated by the spectrum, but because of the cascade of energy perhaps both to smaller and to larger scales than those generated, the spectrum may be produced. An oncoming flow may locally see an inclined 'cylindrical bluff body' that it may have to flow around. A bluff body may be a body that has a strong adverse pressure gradient on its upstream side, perhaps so strong that the shear stress on its wall goes to zero, and the flow may be peeled away from its surface. A point of zero shear stress may define a separation point. This may be a three-dimensional separation. Thus, separation lines (perhaps not just points) and the separation criteria may be far more complicated than a two-dimensional case, but it may still involve very low or even zero shear stress at or even along the length of the separation lines. Because, locally, this spiral may be a cylindrical bluff body on the wall, at an inclination to the axis of the main flow in a bioreactor, a fluid may not follow the contours of the shape. As it attempts to navigate the obstacle, the fluid may detach from the obstacle, or as we say may separate from it. It may however, flow along an axis of the obstruction for some time, perhaps creating a separation bubble which may have a winding flow within it. This separation bubble may form along an axis of the obstruction, may be unstable, may itself break down, and may even add to the cross-flows. A spiraling shape, which may have constantly changing chord-wise inflow conditions, could lead to the cross-section of the bubble, and hence the position of the separation line, perhaps constantly changing, adding to its instability and even more frequent bursting.

A lift coefficient may go down to zero as a gap between a cylinder and a wall may go to zero. As the authors Lei et al 1999 explain, vortex shedding behind the cylinders may have stopped, and the flow may no longer follow a contour of the cylinder around to 120 degrees. It may separate earlier from the cylinders—hence they may exhibit very low lift. Separated flows may leave the cylinder at a large angle. In embodiments of the present invention, exact conditions leading to the separations can vary from instant to instant perhaps because a flow coming towards the spiraling intrusion may be itself unsteady, perhaps both in magnitude and in direction, that may have resulted from similar separations further upstream in the bioreactor. A consequence of a continuous spiraling protrusion may be to produce continual unsteady three-dimensional separations, perhaps occurring randomly in size. The separations may create local separation bubbles, that may grow at a random rate all along the length of the spiraling perturbation. These separation bubbles may be unstable, and may breakdown or burst, perhaps resulting in additional strong cross-flows in a bioreactor. Each local shear layer separation that may occur along a spiral perturbation may result in a cross-flow jet of fluid that may be directed towards the center of a tubing component, and can extend across the diameter of the duct. Perhaps because of the continuity of fluid motions, this may result in the fluid in the center moving away from the center as may be understood in FIGS. 18 and 19. Thus, perhaps all portions of a bioreactor's walls may be disturbed by separated flows perhaps created by the spiraling protrusion. A flow may separate as it tries to go over the helical spine, and thus may dramatically change the flow field. This may also happen when stall occurs on an airplane wing, which will be discussed below. The nature of these separated flows may be that they are not governed by viscosity, as they may now be away from the walls of the apparatus. Flows of this type may be inviscid flows and they may dissipate slowly. Thus, these separated flows can influence the transport of algae or any microorganism for times that are related to the main time scale of the flow, i.e., to d/U, (where d is the diameter of the pipe and U is the mean flow).

We have performed various experiments related to various embodiments of the present invention. A proximity of a wall may influence the non-linear stage of the transition process in a separated shear layer. For example, it may be well known to those familiar with the state of the art that in a certain Reynolds number range, a laminar separation bubble (LSB) may form on the upper surface of a wing, and that the flow oscillations observed may be due to the separation bubble flapping, and perhaps that abrupt stalling of the airfoil may be due to the bubble bursting. The LSB may form when a laminar airstream flows over the wing and may be subjected to a strong adverse pressure gradient, which causes the laminar boundary layer to separate and the stream to travel away from the surface of the airfoil. A deflected stream may be very susceptible to disturbances, and that transition to turbulence in the deflected stream first may be accompanied by the Kelvin-Helmholtz instability. This is described by AlMutairi et al (2017), who studied the dynamics of the phenomena over a wing. But the picture may not seem to qualitatively change in the presence of high free stream turbulence (Hosseinverdi and Fasel 2015), or if the cylinder is skewed to the oncoming flow (Hetsch and Rist 2009). In the case of high free stream turbulence, a separation bubble could be turbulent, and a separated shear layer could be turbulent at the location of separation.

The conditions for the separation of a flow may be known to be essentially Reynolds number independent. Thus, once a correct spiral may be achieving a needed separation at a test speed, one can reduce the speed of the flow until the desired separation effect stops. But, because separation may be Reynolds number independent, it may possible to run the flow in these photobioreactors at lower Reynolds numbers. These lower Reynolds numbers, perhaps for a given size pipe-type BR/PBR, may be achieved by reducing the flow speed. The flow speeds may be reduced to remarkably slow speeds and may still achieve the GEMS, perhaps with its associated cross-flows that bring algae across the PBR from the walls to the center and back to the walls again and again. Being able to lower a flow speed perhaps while maintaining the GEMS may be desirable. This may mean that very little energy expenditure may be required to drive a flow and that very low shear stresses may be applied on the algae cells.

The GEMS also may be insensitive to an increase in Reynolds number. This may allow scalability of a bioreactor system which may open up many industrial applications. One may increase the diameter of the pipe perhaps while keeping a low velocity. As noted herein, a helical disturbance may be scaled up in proportion to a diameter of the pipe. Reynolds number insensitivity may be in support here, where it may be expected to have a similar flow field, thus the cross-flows may continue to move algae across a pipe.

A GEMS device may be very different from classical heat transfer augmentation devices used in pipes, perhaps in its geometry, periodic scale, and even the purpose may be entirely different, perhaps because a GEMS device may exist to create large scale, inviscid cross-flows, whereas heat transfer augmentation devices may be designed to primarily interact with a viscous wall layer flow.

Embodiments of the present invention may drastically change a flow in a bioreactor pipe. Flow separation may be created on a large scale. As can be understood in FIGS. 18-22, this flow separation may create large-scale cross-flows that may traverse the pipe and may bring the algal cells to the light entering the pipe walls and perhaps at the same time take algae away from the walls, so that the resulting motions may enable the algae to grow most effectively (e.g., this may be what characterizes the GEMS). Without these motions, a bioreactor may not be made large enough to satisfy commercial needs perhaps because of a self-shading caused by the faster growth of the algae that are near the walls. As the algae grow, they may darken, and if they stay near the walls, they could block the light from the algae that are further inside the pipe (see FIGS. 6-10). This may be important as algal cell density increases, as the blockage of light may become more severe, and if no explicit mechanism may exist to move the algae away from the walls, and move algae in the middle of a tubing component towards the walls, then a very uneven growth can occur. This can include photobleaching of the algae near the walls and even slow growth of the algae in the middle of the tubing component. This change in the range of, and even intensity of energy in different scales of motion, e.g., a change in the flow spectrum of the algal bioreactor from the natural turbulence spectrum to the GEMS, may be important to the growth of the algae. (An analog is the change in an airplane's lift with and without the flaps extended on take-off and landing, which may result in the survival, or destruction, of an airplane.) It may enable a much larger diameter pipe-type bioreactor to be used (e.g., an area of a bioreactor may increase as the square of the tubing diameter), and hence larger volumes of algae to be produced.

FIGS. 28-31 shows some experimental results using a 6" diameter and an 8" diameter pipe with different inwardly protruding helical spines. A polymer was put into a red vegetable dye, in dilute solution, so that a trail of the dyed particles could be followed before the dye brakes up. The dye was put into the pipe using a centerline injection system. It is showing the results of effects on the flow that several wavelengths of the spiral upstream of the photos can produce. As shown, the dye traverses the pipe going from wall to wall in a random fashion. The large excursions may be carried across the pipe perhaps because of the creation and existence of new large-scale motions (which perhaps are reflected in the existence of the area A, as sketched in the enhanced spectrum of FIG. 5 for a GEMS). These large excursions may at times have a long wavelength, as in FIG. 28, which may appear to be similar to that of a spiral forcing function, but 180° out of phase, and at other times may have a much smaller wavelength then the forcing function as seen in FIG. 29, and seem to appear to have no relation to a forcing function. These images show dye that emanated from a point upstream that has traced these paths at two different times. Fluid particles at all other positions across a cross-section of the pipes may be taking different paths over the times these pictures where taken.

Other benefits of a GEMS device may include that it may not need to move (perhaps like airplane flaps once correctly set for take-off, for example, do not move) perhaps to achieve the desired GEMS. A device's geometry may induce flows that may then produce desired outcomes. This may mean that no direct energy expenditure may be required as could be the case with a moving device. Also, because there may not be any no moving parts, minimum maintenance may be required.

By the nature of a GEMS device, e.g., perhaps since it may be producing energy in largest scales that a pipe-type bioreactor requires for the needed cross-flows, these scales may essentially not be influenced by viscosity, perhaps so that motions that are created at any location within the pipe type bioreactor of essentially cross-stream dimension can persist. This may enable bioreactor devices that produce the GEMS to be themselves of scales much greater than typical laboratory scale devices, and may be implemented on large industrial scales.

There are many passive geometries that can achieve large scale cross-flows through separation of flow over them. All of them are meant to be included in the scope of this patent. Although the discussion may include favorable embodiments, less favorable geometries can result in the needed mixing. Some of the geometries discussed herein may result in the lowest shear stresses on the microorganisms, may result in the lowest energy losses, may be easiest to clean, may result in the least biofilm accumulation, may result in the least light lost coming into a bioreactor, may be easiest to manufacture, and may even put a lowest mechanical stress on the bioreactor system.

Some embodiments of the present invention may provide a set of mechanically stationary devices engineered in a closed BR/PBR that may use fluid dynamic principles to optimize algae growth in a closed BR/PBR by generating large scale cross-flows while continuously providing optimum mixing of nutrients, and gases like CO2, etc., and optimum light dark cycling, if appropriate. It may include one or more cylindrical ducts perhaps with continuous shaped inviscid-scaled helical indents that act as passive mixing elements. These helical indents may be of depth, width and pitch proportional to the main bounding duct scale (diameter if pipe, channel width—if a channel, co-axial gap if coaxial pipe), and proportional to the velocity of the mean flow in said ducts. They may be called inviscid-scaled helical indents. Helical protrusions that may be inserted, or extruded, or even molded into the given cylindrical duct. Spiral protrusions (which can be multiple spiral intrusions, forming, for example a helix, double helix, or triple helix, etc.) may extend into the main duct flow a distance from the duct walls that put the perturbations beyond the dominantly viscosity governed flow field. This may be a desired condition in a co-axial duct flow. A system can be part of an opened or closed bioreactor. A system can use the passive mixing devices with distributed light sources. A system may use a lowest energy to produce cross-flow motions that result in sufficient mixing and create the necessary light/dark cycles. A system may have no moving mechanical parts that are producing cross-flow mixing and light/dark cycling. A system may produce unsteady separation of the flow, and deflection of the flow, which approaches it. A system may produce unsteady separation of the flow that approaches it, which has this separation occur over curved surfaces that produce strong adverse pressure gradients. A system may produce unsteady separation of the flow that approaches it, in which the strong adverse pressure gradients lead to wholesale local separation with the minimum shear stress applied to the fluid. A system may produce unsteady separation of a flow that approaches it, in which the strong adverse pressure gradients lead to regions of local separation with minimum shear stress applied to the fluid. These regions may occur as unsteady, short lived bubbles unevenly distributed over the apparatus. These separations may result in strong cross-flows. A system may contain, within a spiraling locus, finite length protrusions that are generally making up portions of a spiral that has a boundary contained within the spiraling locus of the path. A system may result in very low shear on the algae or other microorganisms, perhaps because the unsteady separation is a result of pressure gradients—not shear. A system may have cross-sectional profiles that result in unsteady separation of the flow moving over them. These could have generally rounded contours, that can range from circular cylinders to airfoil shapes, so as to have the separation points move from moment to moment creating the unsteady three-dimensional flow. A system may avoid sharp corners so as not to force the separations to fixed locations, and so as not in produce high shear. A system may form a continuous array along the ducts, that continuously mixes the algae and the nutrients and the CO2, and/or O2 and or sugar. A system may produce specified light/dark cycling for all algae across the cross-section of the main pipe or channel. By the large-scale nature of the separated flow, a significant proportion of the energy in these cross flow mixing motions may be in flow scales that move the algae over the cross-section of the ducts to continuously create the appropriate light/dark cycles by moving in and out of the distributed light sources photic zones, all created by the fluid dynamic instabilities—not by mechanical motions. A system may provide a mean flow speed needed to put energy into these optimum cross-flow mixing scales, that is much lower than needed to induce energy in equivalent scales of a turbulent flow in empty ducts of equivalent dimensions. These mean flow speeds can be as low as 0.5 in/sec, because separation from the mixing apparatus is essentially Reynolds number independent. A system may be engineered to produce the optimum light/dark cycles, and both the mixing and the light/dark cycles can be tailored to a particular algae's needs. The L/D cycles can be tailored by tailoring the passive mixing device's height, width and pitch, and perhaps even by the number of unsteady separation producing helixes used, and their position within the ducts. A system may be tailored to provide optimum nutrient feeding for a particular microorganism. A system may be tailored to provide optimum $CO_2$ introduction for a particular alga. A system may be tailored to provide optimum $O_2$ removal from the photobioreactor. A system may provide that lighting can be provided by sunlight onto transparent duct walls. A system may provide lighting used that can be discrete LED arrays or solid-state laser light distributed using diffusive fiber optics like, for example, like Corning Fibrance fibers. Concentrated sunlight may be sent into the diffusive fibers. The lighting can emanate into the interior of the main ducts from the spiraling mixing apparatus. This is in general the same spiral ducts/airfoils that may be responsible for the mixing. The lighting emanating in the interior of the main ducts from the spiraling mixing apparatus can be distributed so that the distance the algae must travel may be optimized for their light/dark cycling or even the mixing of $CO_2$ and nutrients. A system may switch between using sunlight and laser light as appropriate, or may use both simultaneously. Appropriate reasons may be because of day/night cycling, wavelength desirability, cloudiness, rain, power needs considerations, or the like. A system may sequentially batch feed the growing algae, and continuously introduce both nutrients, $CO_2$ and light, (or O2, nutrients and sugars) as the algae grows. A system may be constructed to be a single-pass photobioreactor, in which the length of the ducts may be determined by the time required for the alga to grow to the end of their logarithmic phase, or beyond. A system may be a recirculating system which may be constructed, in which case a pump, and bi-pass valves would necessarily be needed. The pump(s) used may be peristaltic pumps if the algae are very shear stress sensitive (like spirulina). A system may be scalable to any size by either increasing the overall dimensions through affine transformation, and or, by adding units of similar dimensions in modular fashion to meet growing needs. A system may have significant scaling up, as may be required for the addition of additional spiraling mixing and lighting devices inside the main duct. A system may provide a continuously flowing, one pass system, and naturally self-cleans, as all predators are washed downstream. A system may be cleaned periodically via simply flushing the duct with water, hot water, or acidic or basic fluids as materials will be, for example, glass, stainless, polycarbonate, and PVC or ABS or new tubing materials.

The above discussion includes both information known to the art prior to the filing date and information forming part of the present inventive disclosure. Inclusion of any statement in this application, whether as a characterization of a published reference or in a discussion of technical problems and their solutions, is not to be taken as an admission that such statement is prior art.

As can be easily understood from the foregoing, the basic concepts of the present invention may be embodied in a variety of ways. It involves both fluid mixing techniques as well as devices to accomplish the appropriate fluid mixing. In this application, the fluid mixing techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. For example, if used as a bioreactor for the growth of livestock cells that must form muscle, fat and connective tissue, we could seek a higher shear version of the inwardly protruding helical spine that may be an example of a passive microorganism flow modifier or even a fluid flow coordinator in that some systems may provide passively modifications a flow of fluid in a tubing component with an inwardly protruding helical spine or even a fluid flow coordinator that results in stretching and contracting of the muscle cells, for example. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. As one example, terms of degree, terms of approximation, and/or relative terms may be used. These may include terms such as the words: substantially, about, only, and the like. These words and types of words are to be understood in a dictionary sense as terms that encompass an ample or considerable amount, quantity, size, etc. as well as terms that encompass largely but not wholly that which is specified. Further, for this application if or when used, terms of degree, terms of approximation, and/or relative terms should be understood as also encompassing more precise and even quantitative values that include various levels of precision and the possibility of claims that address a number of quantitative options and alternatives. For example, to the extent ultimately used, the existence or non-existence of a substance or condition in a particular input, output, or at a particular stage can be specified as substantially only x or substantially free of x, as a value of about x, or such other similar language. Using percentage values as one example, these types of terms should be understood as encompassing the options of percentage values that include 99.5%, 99%, 97%, 95%, 92% or even 90% of the specified value or relative condition; correspondingly for values at the other end of the spectrum (e.g., substantially free of x, these should be understood as encompassing the options of percentage values that include not more than 0.5%, 1%, 3%, 5%, 8% or even 10% of the specified value or relative condition, all whether by volume or by weight as either may be specified. For example, using percentage values as one example, for a tubing component to be substantially filled, it should be understood that embodiments of the invention may encompass the option of percentage values that include 99.5%, 99%, 97%, 95%, 92% or even 90% of a maximum amount of fluid that may completely fill a tubing component. In context, these should be understood by a person of ordinary skill as being disclosed and included whether in an absolute value sense or in valuing one set of or substance as compared to the value of a second set of or substance. Again, these are implicitly included in this disclosure and should (and, it is believed, would) be understood to a person of ordinary skill in this field. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "modifier" should be understood to encompass disclosure of the act of "modifying"—whether explicitly discussed or not—and, conversely, were there effectively disclosure of the act of "modifying", such a disclosure should be understood to encompass disclosure of a "modifier" and even a "means for modifying." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed the information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the fluid mixing devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such processes, methods, systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

In addition and as to computer aspects and each aspect amenable to programming or other electronic automation, it should be understood that in characterizing these and all other aspects of the invention—whether characterized as a device, a capability, an element, or otherwise, because all of these can be implemented via software, hardware, or even firmware structures as set up for a general purpose computer, a programmed chip or chipset, an ASIC, application specific controller, subroutine, or other known programmable or circuit specific structure—it should be understood that all such aspects are at least defined by structures including, as person of ordinary skill in the art would well recognize: hardware circuitry, firmware, programmed application specific components, and even a general purpose computer programmed to accomplish the identified aspect. For such items implemented by programmable features, the applicant(s) should be understood to have support to claim and make a statement of invention to at least: xv) processes performed with the aid of or on a computer, machine, or computing machine as described throughout the above discussion, xvi) a programmable apparatus as described throughout the above discussion, xvii) a computer readable memory encoded with data to direct a computer comprising means or elements which function as described throughout the above discussion, xviii) a computer, machine, or computing machine configured as herein disclosed and described, xix) individual or combined subroutines and programs as herein disclosed and described, xx) a carrier medium carrying computer readable code for control of a computer to carry out separately each and every individual and combined method described herein or in any claim, xxi) a computer program to perform separately each and every individual and combined method disclosed, xxii) a computer program containing all and each combination of means for performing each and every individual and combined step disclosed, xxiii) a storage medium storing each computer program disclosed, xxiv) a signal carrying a computer program disclosed, xxv) a processor executing instructions that act to achieve the steps and activities detailed, xxvi) circuitry configurations (including configurations of transistors, gates, and the like) that act to sequence and/or cause actions as detailed, xxvii) computer readable medium(s) storing instructions to execute the steps and cause activities detailed, xxviii) the related methods disclosed and described, xxix) similar, equivalent, and even implicit variations of each of these systems and methods, xxx) those alternative designs which accomplish each of the functions shown as are disclosed and described, xxxi) those alternative designs and methods which accomplish each of the functions shown as are implicit to accomplish that which is disclosed and described, xxxii) each feature, component, and step shown as separate and independent inventions, and xxxiii) the various combinations of each of the above and of any aspect, all without limiting other aspects in addition.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC,* 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A bioreactor system comprising:
    a tubing component comprising a passive microorganism flow modifier;
    wherein said passive microorganism flow modifier comprises an inwardly protruding helical spine along an inside surface of at least part of said tubing component;
    a plurality of gaps in said inwardly protruding helical spine located along a top inside of said tubing component forming a gas passageway from said gaps along said top inside of said tubing component, wherein said gas passageway is configured to provide gas transport along said top inside of said tubing component;
    fluid in said tubing component introduced by a fluid input;
    an initial inoculum of microorganisms in said fluid in said tubing component introduced by an inoculate input;
    nutrients in said fluid in said tubing component introduced by a nutrient input;
    a fluid flow of said fluid comprising said initial inoculum of microorganisms, and said nutrients through said tubing component; and
    wherein said inwardly protruding helical spine protrudes from said inside surface of said tubing component to a distance beyond a viscous governed flow field region and into an inviscid flow region of said tubing component; and
    wherein said inwardly protruding helical spine is configured to generate cross flows in said fluid flow that convect said microorganisms from a wall of said tubing component toward at least a center of said tubing component resulting in convecting said microorganisms from said center of said tubing component toward said wall of said tubing component when said microorganisms are in said fluid flow in said tubing component.

2. The bioreactor system as described in claim 1 wherein said microorganisms are chosen from algae, bacteria, archaea, protozoa, fungi, viruses, phototrophic microorganisms, heterotrophic microorganisms, mixotrophic microorganisms, and cyanobacteria.

3. The bioreactor system as described in claim 1 further comprising at least one gas release.

4. The bioreactor system as described in claim 1 wherein said inwardly protruding helical spine comprises a scaled inwardly protruding helical spine.

5. The bioreactor system as described in claim 4 wherein said scaled inwardly protruding helical spine comprises a customized pitch, customized width, and customized depth.

6. The bioreactor system as described in claim 4 wherein said scaled inwardly protruding helical spine is configured to disperse said microorganisms across a mean flow in said tubing component.

7. The bioreactor system as described in claim 1 wherein said inwardly protruding helical spine is configured to separate flows and combined with an unsteady magnitude and direction of an approach flow, to prevent fluid flow reattachment of said separated flows in an immediate region downstream of said inwardly protruding helical spine.

8. The bioreactor system as described in claim 1 wherein said tubing component is transparent.

9. The bioreactor system as described in claim 1 and further comprising a light source to which said tubing component has exposure.

10. The bioreactor system as described in claim 9 and further comprising at least one reflector.

11. The bioreactor system as described in claim 1 wherein said inwardly protruding helical spine is configured to produce unsteady separation of said fluid containing said microorganisms from said inwardly protruding helical spine in said fluid flow all along said tubing component.

12. The bioreactor system as described in claim 1 wherein said microorganisms comprises microalgae; and further comprising a light source; and wherein said inwardly protruding helical spine is configured to disperse microalgae all over an inside of said tubing element.

13. The bioreactor system as described in claim 9 wherein said light source is chosen from sunlight, artificial light, laser light, constructed sheets of laser light, pulsed sheets of laser light, LED arrays, solid state laser light, solid state laser light distributed using diffusive fiber optics, sunlight distributed using diffusive fiber optics, and any combination of thereof.

14. The bioreactor system as described in claim 1 wherein said cross flows comprise unsteady multiscale cross flows to disperse said microorganisms within a tubing component.

15. The bioreactor system as described in claim 1 wherein said inwardly protruding helical spine is chosen from an inserted inwardly protruding helical spine in said tubing component; an extruded inwardly protruding helical spine in said tubing component; and a molded inwardly protruding helical spine into said tubing component.

16. The bioreactor system as described in claim 1 wherein said tubing component is formed of flexible tubing or rigid tubing.

\* \* \* \* \*